(12) United States Patent
Widenhouse et al.

(10) Patent No.: US 8,734,478 B2
(45) Date of Patent: May 27, 2014

(54) RECTAL MANIPULATION DEVICES

(75) Inventors: Tamara Widenhouse, Clarksville, OH (US); Frederick E. Shelton, IV, Hillsboro, OH (US); Andrew Yoo, Cincinnati, OH (US); Chester O. Baxter, III, Loveland, OH (US); Barry C. Worrell, Centerville, OH (US); James R. Janszen, Cleves, OH (US); Andrew T. Beckman, Cincinnati, OH (US); Michael J. Vendely, Lebanon, OH (US); Joseph E. Young, Loveland, OH (US); Christopher J. Schall, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 163 days.

(21) Appl. No.: 13/181,842

(22) Filed: Jul. 13, 2011

(65) Prior Publication Data

US 2012/0239075 A1  Sep. 20, 2012

Related U.S. Application Data

(60) Provisional application No. 61/452,432, filed on Mar. 14, 2011.

(51) Int. Cl.
*A61M 29/00* (2006.01)
(52) U.S. Cl.
USPC ............................................. 606/197
(58) Field of Classification Search
USPC ......... 600/184, 201, 202, 203, 204, 205, 206; 604/104, 105, 106, 109; 606/159, 191, 606/197, 198
See application file for complete search history.

(56) References Cited

U.S. PATENT DOCUMENTS

| | | | |
|---|---|---|---|
| 3,166,072 | A | 1/1965 | Sullivan, Jr. |
| 3,266,494 | A | 8/1966 | Brownrigg et al. |
| 3,746,002 | A | 7/1973 | Haller |
| 3,863,639 | A | 2/1975 | Kleaveland |

(Continued)

FOREIGN PATENT DOCUMENTS

| | | |
|---|---|---|
| AU | 2012200178 B2 | 7/2013 |
| CA | 2458946 A1 | 3/2003 |

(Continued)

OTHER PUBLICATIONS

The Free Dictionary definition of "align" as accessed on Sep. 10, 2013; http://www.thefreedictionary.com/align.*

(Continued)

*Primary Examiner* — Ryan Severson
*Assistant Examiner* — Jonathan W Miles

(57) ABSTRACT

Tissue manipulation devices are disclosed. In various forms, the devices include tissue manipulation arms that are arranged in a position suitable to enable the device to be inserted into the colon then, upon application of at least one actuation motion thereto, at least some of the tissue manipulation arms are moved to deployed positions wherein they contact corresponding portions of the colon to thereby expand the colon. Various devices are actuatable by various forms of actuation forces. In various embodiments, the tissue manipulation arms may be movable along corresponding axes that are transverse to an insertion axis and may also be rotated about the insertion axis as well as be moved in directions that are substantially parallel to the insertion axis.

28 Claims, 18 Drawing Sheets

(56) References Cited

U.S. PATENT DOCUMENTS

| | | |
|---|---|---|
| 4,190,042 A | 2/1980 | Sinnreich |
| 4,274,398 A | 6/1981 | Scott, Jr. |
| 4,505,272 A | 3/1985 | Utyamyshev et al. |
| 4,654,028 A | 3/1987 | Suma |
| 4,744,363 A | 5/1988 | Hasson |
| 4,893,622 A | 1/1990 | Green et al. |
| 4,903,697 A | 2/1990 | Resnick et al. |
| 4,909,789 A | 3/1990 | Taguchi et al. |
| 4,984,564 A | 1/1991 | Yuen |
| 5,002,553 A | 3/1991 | Shiber |
| 5,071,430 A | 12/1991 | de Salis et al. |
| 5,104,025 A | 4/1992 | Main et al. |
| 5,108,368 A | 4/1992 | Hammerslag et al. |
| 5,122,156 A | 6/1992 | Granger et al. |
| 5,139,513 A | 8/1992 | Segato |
| 5,158,567 A | 10/1992 | Green |
| 5,195,505 A | 3/1993 | Josefsen |
| 5,205,459 A | 4/1993 | Brinkerhoff et al. |
| 5,222,963 A | 6/1993 | Brinkerhoff et al. |
| 5,222,975 A | 6/1993 | Crainich |
| 5,234,447 A | 8/1993 | Kaster et al. |
| 5,236,440 A | 8/1993 | Hlavacek |
| 5,258,009 A | 11/1993 | Conners |
| 5,282,829 A | 2/1994 | Hermes |
| 5,285,945 A | 2/1994 | Brinkerhoff et al. |
| 5,304,204 A | 4/1994 | Bregen |
| 5,309,927 A | 5/1994 | Welch |
| 5,314,445 A | 5/1994 | Heidmueller née Degwitz et al. |
| 5,330,502 A | 7/1994 | Hassler et al. |
| 5,336,232 A | 8/1994 | Green et al. |
| 5,342,395 A | 8/1994 | Jarrett et al. |
| 5,342,396 A | 8/1994 | Cook |
| 5,350,400 A | 9/1994 | Esposito et al. |
| 5,354,250 A * | 10/1994 | Christensen .................... 482/91 |
| 5,354,303 A | 10/1994 | Spaeth et al. |
| 5,366,479 A | 11/1994 | McGarry et al. |
| 5,374,277 A | 12/1994 | Hassler |
| 5,383,888 A | 1/1995 | Zvenyatsky et al. |
| 5,383,895 A | 1/1995 | Holmes et al. |
| 5,391,180 A | 2/1995 | Tovey et al. |
| 5,404,870 A | 4/1995 | Brinkerhoff et al. |
| 5,405,344 A | 4/1995 | Williamson et al. |
| 5,411,508 A | 5/1995 | Bessler et al. |
| 5,425,745 A | 6/1995 | Green et al. |
| 5,441,494 A | 8/1995 | Ortiz |
| 5,445,644 A | 8/1995 | Pietrafitta et al. |
| 5,474,057 A | 12/1995 | Makower et al. |
| 5,476,479 A | 12/1995 | Green et al. |
| 5,478,354 A | 12/1995 | Tovey et al. |
| 5,480,409 A | 1/1996 | Riza |
| 5,490,819 A | 2/1996 | Nicholas et al. |
| 5,503,635 A | 4/1996 | Sauer et al. |
| 5,514,157 A | 5/1996 | Nicholas et al. |
| 5,520,609 A | 5/1996 | Moll et al. |
| 5,520,678 A | 5/1996 | Heckele et al. |
| 5,527,264 A | 6/1996 | Moll et al. |
| 5,549,621 A | 8/1996 | Bessler et al. |
| 5,549,637 A | 8/1996 | Crainich |
| 5,554,169 A | 9/1996 | Green et al. |
| 5,556,416 A | 9/1996 | Clark et al. |
| 5,558,665 A | 9/1996 | Kieturakis |
| 5,562,690 A | 10/1996 | Green et al. |
| 5,562,701 A | 10/1996 | Huitema et al. |
| 5,562,702 A | 10/1996 | Huitema et al. |
| 5,571,285 A | 11/1996 | Chow et al. |
| 5,575,803 A | 11/1996 | Cooper et al. |
| 5,575,805 A | 11/1996 | Li |
| 5,607,450 A | 3/1997 | Zvenyatsky et al. |
| 5,613,937 A | 3/1997 | Garrison et al. |
| 5,618,303 A | 4/1997 | Marlow et al. |
| 5,618,307 A | 4/1997 | Donlon et al. |
| 5,620,452 A | 4/1997 | Yoon |
| 5,628,743 A | 5/1997 | Cimino |
| 5,651,762 A | 7/1997 | Bridges |
| 5,653,721 A | 8/1997 | Knodel et al. |
| 5,667,517 A | 9/1997 | Hooven |
| 5,667,526 A | 9/1997 | Levin |
| 5,667,527 A | 9/1997 | Cook |
| 5,681,341 A | 10/1997 | Lunsford et al. |
| 5,683,349 A | 11/1997 | Makower et al. |
| 5,695,504 A | 12/1997 | Gifford, III et al. |
| 5,695,524 A | 12/1997 | Kelley et al. |
| 5,697,943 A | 12/1997 | Sauer et al. |
| 5,702,409 A | 12/1997 | Rayburn et al. |
| 5,707,392 A | 1/1998 | Kortenbach |
| 5,725,554 A | 3/1998 | Simon et al. |
| 5,728,121 A | 3/1998 | Bimbo et al. |
| 5,730,758 A | 3/1998 | Allgeyer |
| 5,735,874 A | 4/1998 | Measamer et al. |
| 5,738,629 A | 4/1998 | Moll et al. |
| 5,741,271 A | 4/1998 | Nakao et al. |
| 5,749,889 A | 5/1998 | Bacich et al. |
| 5,749,893 A | 5/1998 | Vidal et al. |
| 5,752,965 A | 5/1998 | Francis et al. |
| 5,766,188 A | 6/1998 | Igaki |
| 5,766,205 A | 6/1998 | Zvenyatsky et al. |
| 5,769,892 A | 6/1998 | Kingwell |
| 5,782,859 A | 7/1998 | Nicholas et al. |
| 5,785,647 A | 7/1998 | Tompkins et al. |
| 5,792,135 A | 8/1998 | Madhani et al. |
| 5,797,959 A | 8/1998 | Castro et al. |
| 5,807,376 A | 9/1998 | Viola et al. |
| 5,807,378 A | 9/1998 | Jensen et al. |
| 5,810,721 A | 9/1998 | Mueller et al. |
| 5,810,855 A | 9/1998 | Rayburn et al. |
| 5,814,057 A | 9/1998 | Oi et al. |
| 5,817,084 A | 10/1998 | Jensen |
| 5,839,639 A | 11/1998 | Sauer et al. |
| 5,843,096 A | 12/1998 | Igaki et al. |
| 5,860,581 A | 1/1999 | Robertson et al. |
| 5,931,853 A | 8/1999 | McEwen et al. |
| 5,964,774 A | 10/1999 | McKean et al. |
| 5,997,528 A | 12/1999 | Bisch et al. |
| 6,024,748 A | 2/2000 | Manzo et al. |
| RE36,720 E | 5/2000 | Green et al. |
| 6,056,735 A | 5/2000 | Okada et al. |
| 6,063,097 A | 5/2000 | Oi et al. |
| 6,083,234 A | 7/2000 | Nicholas et al. |
| 6,083,242 A | 7/2000 | Cook |
| 6,099,551 A | 8/2000 | Gabbay |
| 6,117,158 A | 9/2000 | Measamer et al. |
| 6,142,933 A | 11/2000 | Longo et al. |
| 6,159,200 A | 12/2000 | Verdura et al. |
| 6,162,208 A | 12/2000 | Hipps |
| 6,165,188 A | 12/2000 | Saadat et al. |
| 6,171,330 B1 | 1/2001 | Benchetrit |
| 6,174,318 B1 | 1/2001 | Bates et al. |
| 6,214,028 B1 | 4/2001 | Yoon et al. |
| 6,231,565 B1 | 5/2001 | Tovey et al. |
| 6,248,117 B1 | 6/2001 | Blatter |
| 6,258,107 B1 | 7/2001 | Balázs et al. |
| 6,309,403 B1 | 10/2001 | Minor et al. |
| 6,325,810 B1 | 12/2001 | Hamilton et al. |
| 6,338,737 B1 | 1/2002 | Toledano |
| 6,346,077 B1 | 2/2002 | Taylor et al. |
| 6,387,113 B1 | 5/2002 | Hawkins et al. |
| 6,391,038 B2 | 5/2002 | Vargas et al. |
| 6,398,797 B2 | 6/2002 | Bombard et al. |
| 6,402,766 B2 | 6/2002 | Bowman et al. |
| RE37,814 E | 8/2002 | Allgeyer |
| 6,436,110 B2 | 8/2002 | Bowman et al. |
| 6,436,122 B1 | 8/2002 | Frank et al. |
| 6,440,146 B2 | 8/2002 | Nicholas et al. |
| 6,443,973 B1 | 9/2002 | Whitman |
| 6,494,885 B1 | 12/2002 | Dhindsa |
| 6,503,257 B2 | 1/2003 | Grant et al. |
| 6,503,259 B2 | 1/2003 | Huxel et al. |
| 6,517,565 B1 | 2/2003 | Whitman et al. |
| 6,517,566 B1 | 2/2003 | Hovland et al. |
| 6,551,333 B2 | 4/2003 | Kuhns et al. |
| 6,582,364 B2 | 6/2003 | Butler et al. |
| 6,592,597 B2 | 7/2003 | Grant et al. |
| 6,605,078 B2 | 8/2003 | Adams |
| 6,616,686 B2 | 9/2003 | Coleman et al. |

(56) References Cited

U.S. PATENT DOCUMENTS

| | | |
|---|---|---|
| 6,629,988 B2 | 10/2003 | Weadock |
| 6,638,285 B2 | 10/2003 | Gabbay |
| 6,638,297 B1 | 10/2003 | Huitema |
| 6,645,201 B1 | 11/2003 | Utley et al. |
| 6,656,193 B2 | 12/2003 | Grant et al. |
| 6,692,507 B2 | 2/2004 | Pugsley et al. |
| 6,699,235 B2 | 3/2004 | Wallace et al. |
| 6,716,232 B1 | 4/2004 | Vidal et al. |
| 6,716,233 B1 | 4/2004 | Whitman |
| 6,723,087 B2 | 4/2004 | O'Neill et al. |
| 6,726,697 B2 | 4/2004 | Nicholas et al. |
| 6,736,825 B2 | 5/2004 | Blatter et al. |
| 6,769,590 B2 | 8/2004 | Vresh et al. |
| 6,786,896 B1 | 9/2004 | Madani et al. |
| 6,793,652 B1 | 9/2004 | Whitman et al. |
| 6,821,284 B2 | 11/2004 | Sturtz et al. |
| 6,827,712 B2 | 12/2004 | Tovey et al. |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,872,214 B2 | 3/2005 | Sonnenschein et al. |
| 6,913,608 B2 | 7/2005 | Liddicoat et al. |
| 6,913,613 B2 | 7/2005 | Schwarz et al. |
| 6,936,042 B2 | 8/2005 | Wallace et al. |
| 6,939,358 B2 | 9/2005 | Palacios et al. |
| 6,960,220 B2 | 11/2005 | Marino et al. |
| 6,981,978 B2 | 1/2006 | Gannoe |
| 7,001,408 B2 | 2/2006 | Knodel et al. |
| 7,052,454 B2 | 5/2006 | Taylor |
| 7,056,330 B2 | 6/2006 | Gayton |
| 7,063,712 B2 | 6/2006 | Vargas et al. |
| 7,066,944 B2 | 6/2006 | Laufer et al. |
| 7,077,856 B2 | 7/2006 | Whitman |
| 7,087,071 B2 | 8/2006 | Nicholas et al. |
| 7,094,247 B2 | 8/2006 | Monassevitch et al. |
| 7,108,701 B2 | 9/2006 | Evens et al. |
| 7,108,709 B2 | 9/2006 | Cummins |
| 7,122,028 B2 | 10/2006 | Looper et al. |
| 7,128,748 B2 | 10/2006 | Mooradian et al. |
| 7,147,650 B2 | 12/2006 | Lee |
| 7,156,863 B2 | 1/2007 | Sonnenschein et al. |
| 7,179,267 B2 | 2/2007 | Nolan et al. |
| 7,208,005 B2 | 4/2007 | Frecker et al. |
| 7,220,272 B2 | 5/2007 | Weadock |
| 7,229,408 B2 | 6/2007 | Douglas et al. |
| 7,238,195 B2 | 7/2007 | Viola |
| 7,241,288 B2 | 7/2007 | Braun |
| 7,252,660 B2 | 8/2007 | Kunz |
| 7,267,679 B2 | 9/2007 | McGuckin, Jr. et al. |
| 7,300,450 B2 | 11/2007 | Vleugels et al. |
| 7,328,828 B2 | 2/2008 | Ortiz et al. |
| 7,338,505 B2 | 3/2008 | Belson |
| 7,338,513 B2 | 3/2008 | Lee et al. |
| 7,354,447 B2 | 4/2008 | Shelton, IV et al. |
| 7,377,928 B2 | 5/2008 | Zubik et al. |
| 7,407,078 B2 | 8/2008 | Shelton, IV et al. |
| 7,416,101 B2 | 8/2008 | Shelton, IV et al. |
| 7,422,139 B2 | 9/2008 | Shelton, IV et al. |
| 7,431,189 B2 | 10/2008 | Shelton, IV et al. |
| 7,431,730 B2 | 10/2008 | Viola |
| 7,434,717 B2 | 10/2008 | Shelton, IV et al. |
| 7,438,209 B1 | 10/2008 | Hess et al. |
| 7,441,684 B2 | 10/2008 | Shelton, IV et al. |
| 7,441,685 B1 | 10/2008 | Boudreaux |
| 7,448,525 B2 | 11/2008 | Shelton, IV et al. |
| 7,455,682 B2 | 11/2008 | Viola |
| 7,464,846 B2 | 12/2008 | Shelton, IV et al. |
| 7,464,849 B2 | 12/2008 | Shelton, IV et al. |
| 7,467,740 B2 | 12/2008 | Shelton, IV et al. |
| 7,472,815 B2 | 1/2009 | Shelton, IV et al. |
| 7,473,221 B2 | 1/2009 | Ewers et al. |
| 7,481,824 B2 | 1/2009 | Boudreaux et al. |
| 7,490,749 B2 | 2/2009 | Schall et al. |
| 7,491,232 B2 | 2/2009 | Bolduc et al. |
| 7,494,499 B2 | 2/2009 | Nagase et al. |
| 7,500,979 B2 | 3/2009 | Hueil et al. |
| 7,506,791 B2 | 3/2009 | Omaits et al. |
| 7,510,107 B2 | 3/2009 | Timm et al. |
| 7,517,356 B2 | 4/2009 | Heinrich |
| 7,547,312 B2 | 6/2009 | Bauman et al. |
| 7,549,564 B2 | 6/2009 | Boudreaux |
| 7,549,998 B2 | 6/2009 | Braun |
| 7,568,603 B2 | 8/2009 | Shelton, IV et al. |
| 7,588,175 B2 | 9/2009 | Timm et al. |
| 7,588,176 B2 | 9/2009 | Timm et al. |
| 7,597,229 B2 | 10/2009 | Boudreaux et al. |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,644,848 B2 | 1/2010 | Swayze et al. |
| 7,648,519 B2 | 1/2010 | Lee et al. |
| 7,658,311 B2 | 2/2010 | Boudreaux |
| 7,665,647 B2 | 2/2010 | Shelton, IV et al. |
| 7,669,746 B2 | 3/2010 | Shelton, IV |
| 7,669,747 B2 | 3/2010 | Weisenburgh, II et al. |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,674,255 B2 | 3/2010 | Braun |
| 7,686,201 B2 | 3/2010 | Csiky |
| 7,686,826 B2 | 3/2010 | Lee et al. |
| 7,691,098 B2 | 4/2010 | Wallace et al. |
| 7,699,844 B2 | 4/2010 | Utley et al. |
| 7,699,859 B2 | 4/2010 | Bombard et al. |
| 7,708,758 B2 | 5/2010 | Lee et al. |
| 7,721,931 B2 | 5/2010 | Shelton, IV et al. |
| 7,721,934 B2 | 5/2010 | Shelton, IV et al. |
| 7,721,936 B2 | 5/2010 | Shalton, IV et al. |
| 7,731,072 B2 | 6/2010 | Timm et al. |
| 7,735,703 B2 | 6/2010 | Morgan et al. |
| 7,736,306 B2 | 6/2010 | Brustad et al. |
| 7,738,971 B2 | 6/2010 | Swayze et al. |
| 7,740,159 B2 | 6/2010 | Shelton, IV et al. |
| 7,753,245 B2 | 7/2010 | Boudreaux et al. |
| 7,753,904 B2 | 7/2010 | Shelton, IV et al. |
| 7,766,209 B2 | 8/2010 | Baxter, III et al. |
| 7,766,210 B2 | 8/2010 | Shelton, IV et al. |
| 7,770,775 B2 | 8/2010 | Shelton, IV et al. |
| 7,776,060 B2 | 8/2010 | Mooradian et al. |
| 7,780,685 B2 | 8/2010 | Hunt et al. |
| 7,789,889 B2 | 9/2010 | Zubik et al. |
| 7,793,812 B2 | 9/2010 | Moore et al. |
| 7,794,475 B2 | 9/2010 | Hess et al. |
| 7,798,386 B2 | 9/2010 | Schall et al. |
| 7,799,039 B2 | 9/2010 | Shelton, IV et al. |
| 7,803,151 B2 | 9/2010 | Whitman |
| 7,806,891 B2 | 10/2010 | Nowlin et al. |
| 7,810,692 B2 | 10/2010 | Hall et al. |
| 7,810,693 B2 | 10/2010 | Broehl et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,828,808 B2 | 11/2010 | Hinman et al. |
| 7,832,408 B2 | 11/2010 | Shelton, IV et al. |
| 7,832,612 B2 | 11/2010 | Baxter, III et al. |
| 7,837,080 B2 | 11/2010 | Schwemberger |
| 7,845,537 B2 | 12/2010 | Shelton, IV et al. |
| 7,846,149 B2 | 12/2010 | Jankowski |
| 7,857,185 B2 | 12/2010 | Swayze et al. |
| 7,857,186 B2 | 12/2010 | Baxter, III et al. |
| 7,861,906 B2 | 1/2011 | Doll et al. |
| 7,866,527 B2 | 1/2011 | Hall et al. |
| 7,871,418 B2 | 1/2011 | Thompson et al. |
| 7,883,461 B2 | 2/2011 | Albrecht et al. |
| 7,900,805 B2 | 3/2011 | Shelton, IV et al. |
| 7,905,380 B2 | 3/2011 | Shelton, IV et al. |
| 7,905,381 B2 | 3/2011 | Baxter, III et al. |
| 7,913,891 B2 | 3/2011 | Doll et al. |
| 7,914,543 B2 | 3/2011 | Roth et al. |
| 7,918,377 B2 | 4/2011 | Measamer et al. |

(56) References Cited

U.S. PATENT DOCUMENTS

| | | |
|---|---|---|
| 7,922,061 B2 | 4/2011 | Shelton, IV et al. |
| 7,934,630 B2 | 5/2011 | Shelton, IV et al. |
| 7,942,890 B2 | 5/2011 | D'Agostino et al. |
| 7,954,682 B2 | 6/2011 | Giordano et al. |
| 7,954,684 B2 | 6/2011 | Boudreaux |
| 7,954,686 B2 | 6/2011 | Baxter, III et al. |
| 7,955,253 B2 | 6/2011 | Ewers et al. |
| 7,955,257 B2 | 6/2011 | Frasier et al. |
| 7,959,051 B2 | 6/2011 | Smith et al. |
| 7,966,799 B2 | 6/2011 | Morgan et al. |
| 7,980,443 B2 | 7/2011 | Scheib et al. |
| 8,002,696 B2 | 8/2011 | Suzuki |
| 8,002,795 B2 | 8/2011 | Beetel |
| 8,020,743 B2 | 9/2011 | Shelton, IV |
| 8,034,077 B2 | 10/2011 | Smith et al. |
| 8,056,787 B2 | 11/2011 | Boudreaux et al. |
| 8,066,167 B2 | 11/2011 | Measamer et al. |
| D650,074 S | 12/2011 | Hunt et al. |
| 8,083,120 B2 | 12/2011 | Shelton, IV et al. |
| 8,097,017 B2 | 1/2012 | Viola |
| 8,113,410 B2 | 2/2012 | Hall et al. |
| 8,123,767 B2 | 2/2012 | Bauman et al. |
| 8,128,645 B2 | 3/2012 | Sonnenschein et al. |
| 8,136,712 B2 | 3/2012 | Zingman |
| 8,141,762 B2 | 3/2012 | Bedi et al. |
| 8,157,145 B2 | 4/2012 | Shelton, IV et al. |
| 8,157,153 B2 | 4/2012 | Shelton, IV et al. |
| 8,161,977 B2 | 4/2012 | Shelton, IV et al. |
| 8,167,185 B2 | 5/2012 | Shelton, IV et al. |
| 8,172,124 B2 | 5/2012 | Shelton, IV et al. |
| 8,186,555 B2 | 5/2012 | Shelton, IV et al. |
| 8,186,560 B2 | 5/2012 | Hess et al. |
| 8,196,795 B2 | 6/2012 | Moore et al. |
| 8,196,796 B2 | 6/2012 | Shelton, IV et al. |
| 8,205,781 B2 | 6/2012 | Baxter, III et al. |
| 8,210,411 B2 | 7/2012 | Yates et al. |
| 8,211,125 B2 | 7/2012 | Spivey |
| 8,215,531 B2 | 7/2012 | Shelton, IV et al. |
| 8,220,688 B2 | 7/2012 | Laurent et al. |
| 8,220,690 B2 | 7/2012 | Hess et al. |
| 8,226,553 B2 | 7/2012 | Shelton, IV et al. |
| 8,241,271 B2 | 8/2012 | Millman et al. |
| 8,267,300 B2 | 9/2012 | Boudreaux |
| 8,292,155 B2 | 10/2012 | Shelton, IV et al. |
| 8,308,040 B2 | 11/2012 | Huang et al. |
| 8,317,070 B2 | 11/2012 | Hueil et al. |
| 8,322,455 B2 | 12/2012 | Shelton, IV et al. |
| 8,322,589 B2 | 12/2012 | Boudreaux |
| 8,333,313 B2 | 12/2012 | Boudreaux et al. |
| 8,348,129 B2 | 1/2013 | Bedi et al. |
| 8,348,131 B2 | 1/2013 | Omaits et al. |
| 8,348,837 B2 | 1/2013 | Wenchell |
| 8,348,972 B2 | 1/2013 | Soltz et al. |
| 8,353,437 B2 | 1/2013 | Boudreaux |
| 8,353,438 B2 | 1/2013 | Baxter, III et al. |
| 8,353,439 B2 | 1/2013 | Baxter, III et al. |
| 8,360,296 B2 | 1/2013 | Zingman |
| 8,360,297 B2 | 1/2013 | Shelton, IV et al. |
| 8,365,976 B2 | 2/2013 | Hess et al. |
| 8,371,491 B2 | 2/2013 | Huitema et al. |
| 8,372,094 B2 | 2/2013 | Bettuchi et al. |
| 8,393,514 B2 | 3/2013 | Shelton, IV et al. |
| 8,397,971 B2 | 3/2013 | Yates et al. |
| 8,398,669 B2 | 3/2013 | Kim |
| 8,408,439 B2 | 4/2013 | Huang et al. |
| 8,414,577 B2 | 4/2013 | Boudreaux et al. |
| 8,424,740 B2 | 4/2013 | Shelton, IV et al. |
| 8,444,036 B2 | 5/2013 | Shelton, IV |
| 8,453,907 B2 | 6/2013 | Laurent et al. |
| 8,453,908 B2 | 6/2013 | Bedi et al. |
| 8,453,914 B2 | 6/2013 | Laurent et al. |
| 8,459,520 B2 | 6/2013 | Giordano et al. |
| 8,459,525 B2 | 6/2013 | Yates et al. |
| 8,464,923 B2 | 6/2013 | Shelton, IV |
| 8,474,677 B2 | 7/2013 | Woodard, Jr. et al. |
| 8,479,969 B2 | 7/2013 | Shelton, IV |
| 8,485,412 B2 | 7/2013 | Shelton, IV et al. |
| 8,485,413 B2 | 7/2013 | Scheib et al. |
| 8,485,970 B2 | 7/2013 | Widenhouse et al. |
| 8,517,239 B2 | 8/2013 | Scheib et al. |
| 8,517,243 B2 | 8/2013 | Giordano et al. |
| 8,517,244 B2 | 8/2013 | Shelton, IV et al. |
| 8,529,600 B2 | 9/2013 | Woodard, Jr. et al. |
| 8,540,128 B2 | 9/2013 | Shelton, IV et al. |
| 8,540,129 B2 | 9/2013 | Baxter, III et al. |
| 8,540,130 B2 | 9/2013 | Moore et al. |
| 8,540,131 B2 | 9/2013 | Swayze |
| 8,540,133 B2 | 9/2013 | Bedi et al. |
| 8,561,870 B2 | 10/2013 | Baxter, III et al. |
| 8,567,656 B2 | 10/2013 | Shelton, IV et al. |
| 8,573,461 B2 | 11/2013 | Shelton, IV et al. |
| 8,573,465 B2 | 11/2013 | Shelton, IV et al. |
| 2002/0095175 A1 | 7/2002 | Brock et al. |
| 2003/0220660 A1 | 11/2003 | Kortenbach et al. |
| 2004/0006372 A1 | 1/2004 | Racenet et al. |
| 2004/0097987 A1 | 5/2004 | Pugsley et al. |
| 2004/0098040 A1 | 5/2004 | Taniguchi et al. |
| 2004/0111081 A1 | 6/2004 | Whitman et al. |
| 2004/0147909 A1 | 7/2004 | Johnston et al. |
| 2004/0167572 A1 | 8/2004 | Roth et al. |
| 2004/0193177 A1 | 9/2004 | Houghton et al. |
| 2004/0193189 A1 | 9/2004 | Kortenbach et al. |
| 2004/0243176 A1 | 12/2004 | Hahnen et al. |
| 2004/0254566 A1 | 12/2004 | Plicchi et al. |
| 2004/0254608 A1 | 12/2004 | Huitema et al. |
| 2004/0260315 A1 | 12/2004 | Dell et al. |
| 2004/0267310 A1 | 12/2004 | Racenet et al. |
| 2005/0033357 A1 | 2/2005 | Braun |
| 2005/0059997 A1 | 3/2005 | Bauman et al. |
| 2005/0070929 A1 | 3/2005 | Dalessandro et al. |
| 2005/0085693 A1 | 4/2005 | Belson et al. |
| 2005/0107824 A1 | 5/2005 | Hillstead et al. |
| 2005/0131390 A1 | 6/2005 | Heinrich et al. |
| 2005/0131457 A1 | 6/2005 | Douglas et al. |
| 2005/0177181 A1 | 8/2005 | Kagan et al. |
| 2005/0182298 A1 | 8/2005 | Ikeda et al. |
| 2005/0187576 A1 | 8/2005 | Whitman et al. |
| 2005/0192628 A1 | 9/2005 | Viola |
| 2005/0203550 A1 | 9/2005 | Laufer et al. |
| 2005/0216055 A1 | 9/2005 | Scirica et al. |
| 2005/0240222 A1 | 10/2005 | Shipp |
| 2005/0256452 A1 | 11/2005 | DeMarchi et al. |
| 2006/0020258 A1 | 1/2006 | Strauss et al. |
| 2006/0025811 A1 | 2/2006 | Shelton et al. |
| 2006/0025812 A1 | 2/2006 | Shelton et al. |
| 2006/0025813 A1 | 2/2006 | Shelton et al. |
| 2006/0041188 A1 | 2/2006 | Dirusso et al. |
| 2006/0047303 A1 | 3/2006 | Ortiz et al. |
| 2006/0047307 A1 | 3/2006 | Ortiz et al. |
| 2006/0052825 A1 | 3/2006 | Ransick et al. |
| 2006/0085033 A1 | 4/2006 | Criscuolo et al. |
| 2006/0161185 A1 | 7/2006 | Saadat et al. |
| 2006/0173470 A1 | 8/2006 | Oray et al. |
| 2006/0201989 A1 | 9/2006 | Ojeda |
| 2006/0212069 A1 | 9/2006 | Shelton et al. |
| 2006/0235469 A1 | 10/2006 | Viola |
| 2006/0241692 A1 | 10/2006 | McGuckin, Jr. et al. |
| 2006/0252993 A1 | 11/2006 | Freed et al. |
| 2006/0258904 A1 | 11/2006 | Stefanchik et al. |
| 2006/0259073 A1 | 11/2006 | Miyamoto et al. |
| 2006/0271102 A1 | 11/2006 | Bosshard et al. |
| 2007/0027468 A1 | 2/2007 | Wales et al. |
| 2007/0027469 A1 | 2/2007 | Smith et al. |
| 2007/0055219 A1 | 3/2007 | Whitman et al. |
| 2007/0073341 A1 | 3/2007 | Smith |
| 2007/0078484 A1 | 4/2007 | Talarico et al. |
| 2007/0102472 A1 | 5/2007 | Shelton, IV |
| 2007/0106317 A1 | 5/2007 | Shelton, IV et al. |
| 2007/0118175 A1 | 5/2007 | Butler et al. |
| 2007/0129605 A1 | 6/2007 | Schaaf |
| 2007/0135803 A1 | 6/2007 | Belson |
| 2007/0170225 A1 | 7/2007 | Shelton, IV et al. |
| 2007/0175949 A1 | 8/2007 | Shelton, IV et al. |
| 2007/0175950 A1 | 8/2007 | Shelton, IV et al. |

(56) References Cited

U.S. PATENT DOCUMENTS

| | | |
|---|---|---|
| 2007/0175951 A1 | 8/2007 | Shelton, IV et al. |
| 2007/0175955 A1 | 8/2007 | Shelton, IV et al. |
| 2007/0194079 A1 | 8/2007 | Hueil et al. |
| 2007/0194082 A1 | 8/2007 | Morgan et al. |
| 2007/0203510 A1 | 8/2007 | Bettuchi |
| 2007/0225562 A1 | 9/2007 | Spivey et al. |
| 2007/0239028 A1 | 10/2007 | Houser et al. |
| 2007/0244471 A1 | 10/2007 | Malackowski |
| 2007/0270784 A1 | 11/2007 | Smith et al. |
| 2007/0276189 A1 | 11/2007 | Abel et al. |
| 2007/0299427 A1 | 12/2007 | Yeung et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0078800 A1 | 4/2008 | Hess et al. |
| 2008/0078802 A1 | 4/2008 | Hess et al. |
| 2008/0082114 A1 | 4/2008 | McKenna et al. |
| 2008/0082125 A1 | 4/2008 | Murray et al. |
| 2008/0140115 A1 | 6/2008 | Stopek |
| 2008/0154299 A1 | 6/2008 | Livneh |
| 2008/0167522 A1 | 7/2008 | Giordano et al. |
| 2008/0169328 A1 | 7/2008 | Shelton |
| 2008/0169329 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0172088 A1 | 7/2008 | Smith et al. |
| 2008/0242939 A1 | 10/2008 | Johnston |
| 2008/0255413 A1 | 10/2008 | Zemlok et al. |
| 2008/0296346 A1 | 12/2008 | Shelton, IV et al. |
| 2008/0308602 A1 | 12/2008 | Timm et al. |
| 2008/0308603 A1 | 12/2008 | Shelton et al. |
| 2009/0001121 A1 | 1/2009 | Hess et al. |
| 2009/0001124 A1 | 1/2009 | Hess et al. |
| 2009/0001130 A1 | 1/2009 | Hess et al. |
| 2009/0005807 A1 | 1/2009 | Hess et al. |
| 2009/0005808 A1 | 1/2009 | Hess et al. |
| 2009/0005809 A1 | 1/2009 | Hess et al. |
| 2009/0012556 A1 | 1/2009 | Boudreaux et al. |
| 2009/0149871 A9 | 6/2009 | Kagan et al. |
| 2009/0198272 A1 | 8/2009 | Kerver et al. |
| 2009/0206125 A1 | 8/2009 | Huitema et al. |
| 2009/0206126 A1 | 8/2009 | Huitema et al. |
| 2009/0206131 A1 | 8/2009 | Weisenburgh, II et al. |
| 2009/0206132 A1 | 8/2009 | Hueil et al. |
| 2009/0206133 A1 | 8/2009 | Morgan et al. |
| 2009/0206137 A1 | 8/2009 | Hall et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0209946 A1 | 8/2009 | Swayze et al. |
| 2009/0209979 A1 | 8/2009 | Yates et al. |
| 2009/0209990 A1 | 8/2009 | Yates et al. |
| 2009/0242610 A1 | 10/2009 | Shelton, Iv et al. |
| 2009/0292176 A1 | 11/2009 | Bonadio et al. |
| 2010/0069942 A1 | 3/2010 | Shelton, Iv |
| 2010/0076475 A1 | 3/2010 | Yates et al. |
| 2010/0087840 A1 | 4/2010 | Ebersole et al. |
| 2010/0089970 A1 | 4/2010 | Smith et al. |
| 2010/0133317 A1 | 6/2010 | Shelton, IV et al. |
| 2010/0179382 A1 | 7/2010 | Shelton, IV et al. |
| 2010/0193566 A1 | 8/2010 | Scheib et al. |
| 2010/0222901 A1 | 9/2010 | Swayze et al. |
| 2010/0224669 A1 | 9/2010 | Shelton, IV et al. |
| 2010/0228091 A1 | 9/2010 | Widenhouse et al. |
| 2010/0243709 A1 | 9/2010 | Hess et al. |
| 2010/0292540 A1 | 11/2010 | Hess et al. |
| 2010/0294829 A1 | 11/2010 | Giordano et al. |
| 2010/0301095 A1 | 12/2010 | Shelton, IV et al. |
| 2010/0305552 A1 | 12/2010 | Shelton, IV et al. |
| 2010/0312261 A1 | 12/2010 | Suzuki et al. |
| 2010/0331880 A1 | 12/2010 | Stopek |
| 2011/0006099 A1 | 1/2011 | Hall et al. |
| 2011/0006101 A1 | 1/2011 | Hall et al. |
| 2011/0022032 A1 | 1/2011 | Zemlok et al. |
| 2011/0024477 A1 | 2/2011 | Hall et al. |
| 2011/0024478 A1 | 2/2011 | Shelton, IV |
| 2011/0024479 A1 | 2/2011 | Swensgard et al. |
| 2011/0060363 A1 | 3/2011 | Hess et al. |
| 2011/0068148 A1 | 3/2011 | Hall et al. |
| 2011/0087276 A1 | 4/2011 | Bedi et al. |
| 2011/0087279 A1 | 4/2011 | Shah et al. |
| 2011/0114697 A1 | 5/2011 | Baxter, III et al. |
| 2011/0114700 A1 | 5/2011 | Baxter, III et al. |
| 2011/0118761 A1 | 5/2011 | Baxter, III et al. |
| 2011/0125176 A1 | 5/2011 | Yates et al. |
| 2011/0125177 A1 | 5/2011 | Yates et al. |
| 2011/0132964 A1 | 6/2011 | Weisenburgh, II et al. |
| 2011/0144430 A1 | 6/2011 | Spivey et al. |
| 2011/0147433 A1 | 6/2011 | Shelton, IV et al. |
| 2011/0147434 A1 | 6/2011 | Hueil et al. |
| 2011/0155781 A1 | 6/2011 | Swensgard et al. |
| 2011/0155784 A1 | 6/2011 | Shelton, IV et al. |
| 2011/0155786 A1 | 6/2011 | Shelton, IV |
| 2011/0155787 A1 | 6/2011 | Baxter, III et al. |
| 2011/0163147 A1 | 7/2011 | Laurent et al. |
| 2011/0174861 A1 | 7/2011 | Shelton, IV et al. |
| 2011/0174862 A1 | 7/2011 | Shelton, IV et al. |
| 2011/0192882 A1 | 8/2011 | Hess et al. |
| 2011/0275901 A1 | 11/2011 | Shelton, IV |
| 2011/0276083 A1 | 11/2011 | Shelton, IV et al. |
| 2011/0288573 A1 | 11/2011 | Yates et al. |
| 2011/0290851 A1 | 12/2011 | Shelton, IV |
| 2011/0290853 A1 | 12/2011 | Shelton, IV et al. |
| 2011/0290854 A1 | 12/2011 | Timm et al. |
| 2011/0290855 A1 | 12/2011 | Moore et al. |
| 2011/0290856 A1 | 12/2011 | Shelton, IV et al. |
| 2011/0295242 A1 | 12/2011 | Spivey et al. |
| 2011/0295269 A1 | 12/2011 | Swensgard et al. |
| 2011/0295270 A1 | 12/2011 | Giordano et al. |
| 2011/0295295 A1 | 12/2011 | Shelton, IV et al. |
| 2012/0024934 A1 | 2/2012 | Shelton, IV et al. |
| 2012/0024935 A1 | 2/2012 | Shelton, IV et al. |
| 2012/0024936 A1 | 2/2012 | Baxter, III et al. |
| 2012/0029272 A1 | 2/2012 | Shelton, IV et al. |
| 2012/0029544 A1 | 2/2012 | Shelton, IV et al. |
| 2012/0029547 A1 | 2/2012 | Shelton, IV et al. |
| 2012/0046692 A1 | 2/2012 | Smith et al. |
| 2012/0071711 A1 | 3/2012 | Shelton, IV et al. |
| 2012/0071866 A1 | 3/2012 | Kerr et al. |
| 2012/0074196 A1 | 3/2012 | Shelton, IV et al. |
| 2012/0074198 A1 | 3/2012 | Huitema et al. |
| 2012/0074200 A1 | 3/2012 | Schmid et al. |
| 2012/0074201 A1 | 3/2012 | Baxter, III et al. |
| 2012/0080332 A1 | 4/2012 | Shelton, IV et al. |
| 2012/0080335 A1 | 4/2012 | Shelton, IV et al. |
| 2012/0080336 A1 | 4/2012 | Shelton, IV et al. |
| 2012/0080337 A1 | 4/2012 | Shelton, IV et al. |
| 2012/0080338 A1 | 4/2012 | Shelton, IV et al. |
| 2012/0080339 A1 | 4/2012 | Shelton, IV et al. |
| 2012/0080340 A1 | 4/2012 | Shelton, IV et al. |
| 2012/0080344 A1 | 4/2012 | Shelton, IV |
| 2012/0080345 A1 | 4/2012 | Morgan et al. |
| 2012/0080477 A1 | 4/2012 | Leimbach et al. |
| 2012/0080478 A1 | 4/2012 | Morgan et al. |
| 2012/0080479 A1 | 4/2012 | Shelton, IV |
| 2012/0080480 A1 | 4/2012 | Woodard, Jr. et al. |
| 2012/0080481 A1 | 4/2012 | Widenhouse et al. |
| 2012/0080482 A1 | 4/2012 | Schall et al. |
| 2012/0080483 A1 | 4/2012 | Riestenberg et al. |
| 2012/0080484 A1 | 4/2012 | Morgan et al. |
| 2012/0080485 A1 | 4/2012 | Woodard, Jr. et al. |
| 2012/0080486 A1 | 4/2012 | Woodard, Jr. et al. |
| 2012/0080488 A1 | 4/2012 | Shelton, IV et al. |
| 2012/0080489 A1 | 4/2012 | Shelton, IV et al. |
| 2012/0080490 A1 | 4/2012 | Shelton, IV et al. |
| 2012/0080491 A1 | 4/2012 | Shelton, IV et al. |
| 2012/0080493 A1 | 4/2012 | Shelton, IV et al. |
| 2012/0080496 A1 | 4/2012 | Schall et al. |
| 2012/0080498 A1 | 4/2012 | Shelton, IV et al. |
| 2012/0080499 A1 | 4/2012 | Schall et al. |
| 2012/0080500 A1 | 4/2012 | Morgan et al. |
| 2012/0080501 A1 | 4/2012 | Morgan et al. |

(56) References Cited

U.S. PATENT DOCUMENTS

| | | |
|---|---|---|
| 2012/0080502 A1 | 4/2012 | Morgan et al. |
| 2012/0080503 A1 | 4/2012 | Woodard, Jr. et al. |
| 2012/0083833 A1 | 4/2012 | Shelton, IV et al. |
| 2012/0083834 A1 | 4/2012 | Shelton, IV et al. |
| 2012/0083835 A1 | 4/2012 | Shelton, IV et al. |
| 2012/0083836 A1 | 4/2012 | Shelton, IV et al. |
| 2012/0132450 A1 | 5/2012 | Timm et al. |
| 2012/0138660 A1 | 6/2012 | Shelton, IV |
| 2012/0160721 A1 | 6/2012 | Shelton, IV et al. |
| 2012/0175399 A1 | 7/2012 | Shelton et al. |
| 2012/0199630 A1 | 8/2012 | Shelton, IV |
| 2012/0199631 A1 | 8/2012 | Shelton, IV et al. |
| 2012/0199632 A1 | 8/2012 | Spivey et al. |
| 2012/0203247 A1 | 8/2012 | Shelton, IV et al. |
| 2012/0234890 A1 | 9/2012 | Aronhalt et al. |
| 2012/0234891 A1 | 9/2012 | Aronhalt et al. |
| 2012/0234892 A1 | 9/2012 | Aronhalt et al. |
| 2012/0234893 A1 | 9/2012 | Schuckmann et al. |
| 2012/0234895 A1 | 9/2012 | O'Connor et al. |
| 2012/0234896 A1 | 9/2012 | Ellerhorst et al. |
| 2012/0234897 A1 | 9/2012 | Shelton, IV et al. |
| 2012/0234898 A1 | 9/2012 | Shelton, IV et al. |
| 2012/0234899 A1 | 9/2012 | Scheib et al. |
| 2012/0238823 A1 | 9/2012 | Hagerty et al. |
| 2012/0238824 A1 | 9/2012 | Widenhouse et al. |
| 2012/0238826 A1 | 9/2012 | Yoo et al. |
| 2012/0238829 A1 | 9/2012 | Shelton, IV et al. |
| 2012/0239009 A1 | 9/2012 | Mollere et al. |
| 2012/0239010 A1 | 9/2012 | Shelton, IV et al. |
| 2012/0239082 A1 | 9/2012 | Shelton, IV et al. |
| 2012/0241491 A1 | 9/2012 | Aldridge et al. |
| 2012/0241492 A1 | 9/2012 | Shelton, IV et al. |
| 2012/0241493 A1 | 9/2012 | Baxter, III et al. |
| 2012/0241496 A1 | 9/2012 | Mandakolathur Vasudevan et al. |
| 2012/0241497 A1 | 9/2012 | Mandakolathur Vasudevan et al. |
| 2012/0241498 A1 | 9/2012 | Gonzalez et al. |
| 2012/0241499 A1 | 9/2012 | Baxter, III et al. |
| 2012/0241500 A1 | 9/2012 | Timmer et al. |
| 2012/0241501 A1 | 9/2012 | Swayze et al. |
| 2012/0241502 A1 | 9/2012 | Aldridge et al. |
| 2012/0241503 A1 | 9/2012 | Baxter, III et al. |
| 2012/0241505 A1 | 9/2012 | Alexander, III et al. |
| 2012/0248169 A1 | 10/2012 | Widenhouse et al. |
| 2012/0253298 A1 | 10/2012 | Henderson et al. |
| 2012/0265230 A1 | 10/2012 | Yates et al. |
| 2012/0283707 A1 | 11/2012 | Giordano et al. |
| 2012/0283748 A1 | 11/2012 | Ortiz et al. |
| 2012/0286019 A1 | 11/2012 | Hueil et al. |
| 2012/0292367 A1 | 11/2012 | Morgan et al. |
| 2012/0292370 A1 | 11/2012 | Hess et al. |
| 2012/0298719 A1 | 11/2012 | Shelton, IV et al. |
| 2012/0298722 A1 | 11/2012 | Hess et al. |
| 2012/0312860 A1 | 12/2012 | Ming et al. |
| 2012/0318842 A1 | 12/2012 | Anim et al. |
| 2012/0318843 A1 | 12/2012 | Henderson et al. |
| 2012/0318844 A1 | 12/2012 | Shelton, IV et al. |
| 2013/0012931 A1 | 1/2013 | Spivey et al. |
| 2013/0012957 A1 | 1/2013 | Shelton, IV et al. |
| 2013/0018361 A1 | 1/2013 | Bryant |
| 2013/0020375 A1 | 1/2013 | Shelton, IV et al. |
| 2013/0020376 A1 | 1/2013 | Shelton, IV et al. |
| 2013/0023861 A1 | 1/2013 | Shelton, IV et al. |
| 2013/0026208 A1 | 1/2013 | Shelton, IV et al. |
| 2013/0026210 A1 | 1/2013 | Shelton, IV et al. |
| 2013/0056518 A1 | 3/2013 | Swensgard |
| 2013/0056520 A1 | 3/2013 | Swensgard |
| 2013/0056521 A1 | 3/2013 | Swensgard |
| 2013/0056522 A1 | 3/2013 | Swensgard |
| 2013/0075443 A1 | 3/2013 | Giordano et al. |
| 2013/0075448 A1 | 3/2013 | Schmid et al. |
| 2013/0075449 A1 | 3/2013 | Schmid et al. |
| 2013/0075450 A1 | 3/2013 | Schmid et al. |
| 2013/0079814 A1 | 3/2013 | Hess et al. |
| 2013/0087597 A1 | 4/2013 | Shelton, IV et al. |
| 2013/0105551 A1 | 5/2013 | Zingman |
| 2013/0116668 A1 | 5/2013 | Shelton, IV et al. |
| 2013/0116669 A1 | 5/2013 | Shelton, IV et al. |
| 2013/0126581 A1 | 5/2013 | Yates et al. |
| 2013/0126582 A1 | 5/2013 | Shelton, IV et al. |
| 2013/0126583 A1 | 5/2013 | Hueil et al. |
| 2013/0146641 A1 | 6/2013 | Shelton, IV et al. |
| 2013/0146642 A1 | 6/2013 | Shelton, IV et al. |
| 2013/0146643 A1 | 6/2013 | Schmid et al. |
| 2013/0153636 A1 | 6/2013 | Shelton, IV et al. |
| 2013/0153641 A1 | 6/2013 | Shelton, IV et al. |
| 2013/0168435 A1 | 7/2013 | Huang et al. |
| 2013/0172929 A1 | 7/2013 | Hess et al. |
| 2013/0175317 A1 | 7/2013 | Yates et al. |
| 2013/0175321 A1 | 7/2013 | Shelton, IV et al. |
| 2013/0175322 A1 | 7/2013 | Yates et al. |
| 2013/0181030 A1 | 7/2013 | Hess et al. |
| 2013/0181033 A1 | 7/2013 | Shelton, IV et al. |
| 2013/0181034 A1 | 7/2013 | Shelton, IV et al. |
| 2013/0184718 A1 | 7/2013 | Smith et al. |
| 2013/0184719 A1 | 7/2013 | Shelton, IV et al. |
| 2013/0186932 A1 | 7/2013 | Shelton, IV et al. |
| 2013/0186933 A1 | 7/2013 | Shelton, IV et al. |
| 2013/0186934 A1 | 7/2013 | Shelton, IV et al. |
| 2013/0186936 A1 | 7/2013 | Shelton, IV |
| 2013/0190733 A1 | 7/2013 | Giordano et al. |
| 2013/0190757 A1 | 7/2013 | Yates et al. |
| 2013/0193188 A1 | 8/2013 | Shelton, IV et al. |
| 2013/0193189 A1 | 8/2013 | Swensgard et al. |
| 2013/0197556 A1 | 8/2013 | Shelton, IV et al. |
| 2013/0200132 A1 | 8/2013 | Moore et al. |
| 2013/0206814 A1 | 8/2013 | Morgan et al. |
| 2013/0214030 A1 | 8/2013 | Aronhalt et al. |
| 2013/0221063 A1 | 8/2013 | Aronhalt et al. |
| 2013/0221064 A1 | 8/2013 | Aronhalt et al. |
| 2013/0221065 A1 | 8/2013 | Aronhalt et al. |
| 2013/0248576 A1 | 9/2013 | Laurent et al. |
| 2013/0248577 A1 | 9/2013 | Leimbach et al. |
| 2013/0256365 A1 | 10/2013 | Shelton, IV et al. |
| 2013/0256366 A1 | 10/2013 | Shelton, IV et al. |
| 2013/0256367 A1 | 10/2013 | Scheib et al. |
| 2013/0256368 A1 | 10/2013 | Timm et al. |
| 2013/0256369 A1 | 10/2013 | Schmid et al. |
| 2013/0256371 A1 | 10/2013 | Shelton, IV et al. |
| 2013/0256372 A1 | 10/2013 | Baxter, III et al. |
| 2013/0256373 A1 | 10/2013 | Schmid et al. |
| 2013/0256377 A1 | 10/2013 | Schmid et al. |
| 2013/0256378 A1 | 10/2013 | Schmid et al. |
| 2013/0256379 A1 | 10/2013 | Schmid et al. |
| 2013/0256380 A1 | 10/2013 | Schmid et al. |
| 2013/0256382 A1 | 10/2013 | Swayze et al. |
| 2013/0256383 A1 | 10/2013 | Aronhalt et al. |
| 2013/0261648 A1 | 10/2013 | Laurent et al. |

FOREIGN PATENT DOCUMENTS

| | | |
|---|---|---|
| CA | 2512960 A1 | 1/2006 |
| CA | 2514274 A1 | 1/2006 |
| CN | 2488482 Y | 5/2002 |
| CN | 1523725 A | 8/2004 |
| CN | 1634601 A | 7/2005 |
| CN | 1868411 A | 11/2006 |
| CN | 1915180 A | 2/2007 |
| CN | 101011286 A | 8/2007 |
| CN | 101095621 A | 1/2008 |
| CN | 101023879 B | 3/2013 |
| DE | 273689 C | 5/1914 |
| DE | 1775926 A | 1/1972 |
| DE | 3036217 A1 | 4/1982 |
| DE | 3212828 A1 | 11/1982 |
| DE | 3210466 A1 | 9/1983 |
| DE | 3709067 A1 | 9/1988 |
| DE | 9412228 U | 9/1994 |
| DE | 19509116 A1 | 9/1996 |
| DE | 19851291 A1 | 1/2000 |
| DE | 19924311 A1 | 11/2000 |
| DE | 69328576 T2 | 1/2001 |
| DE | 20016423 U1 | 2/2001 |
| DE | 10052679 A1 | 5/2001 |
| DE | 20112837 U1 | 10/2001 |

(56) References Cited

FOREIGN PATENT DOCUMENTS

| | | |
|---|---|---|
| DE | 20121753 U1 | 4/2003 |
| DE | 10314072 A1 | 10/2004 |
| DE | 202007003114 U1 | 6/2007 |
| EP | 0122046 A1 | 10/1984 |
| EP | 0070230 B1 | 10/1985 |
| EP | 0156774 A2 | 10/1985 |
| EP | 0387980 B1 | 10/1985 |
| EP | 0033548 B1 | 5/1986 |
| EP | 0129442 B1 | 11/1987 |
| EP | 0276104 A2 | 7/1988 |
| EP | 0178940 B1 | 1/1991 |
| EP | 0178941 B1 | 1/1991 |
| EP | 0248844 B1 | 1/1993 |
| EP | 0545029 A1 | 6/1993 |
| EP | 0277959 B1 | 10/1993 |
| EP | 0233940 B1 | 11/1993 |
| EP | 0261230 B1 | 11/1993 |
| EP | 0639349 A2 | 2/1994 |
| EP | 0324636 B1 | 3/1994 |
| EP | 0593920 A1 | 4/1994 |
| EP | 0594148 A1 | 4/1994 |
| EP | 0427949 B1 | 6/1994 |
| EP | 0523174 B1 | 6/1994 |
| EP | 0600182 A2 | 6/1994 |
| EP | 0310431 B1 | 11/1994 |
| EP | 0375302 B1 | 11/1994 |
| EP | 0376562 B1 | 11/1994 |
| EP | 0630612 A1 | 12/1994 |
| EP | 0634144 A1 | 1/1995 |
| EP | 0646356 A2 | 4/1995 |
| EP | 0646357 A1 | 4/1995 |
| EP | 0653189 A2 | 5/1995 |
| EP | 0669104 A1 | 8/1995 |
| EP | 0511470 B1 | 10/1995 |
| EP | 0674876 A2 | 10/1995 |
| EP | 0679367 A2 | 11/1995 |
| EP | 0392547 B1 | 12/1995 |
| EP | 0685204 A1 | 12/1995 |
| EP | 0364216 B1 | 1/1996 |
| EP | 0699418 A1 | 3/1996 |
| EP | 0702937 A1 | 3/1996 |
| EP | 0705571 A1 | 4/1996 |
| EP | 0711611 A2 | 5/1996 |
| EP | 0484677 B2 | 6/1996 |
| EP | 0541987 B1 | 7/1996 |
| EP | 0667119 B1 | 7/1996 |
| EP | 0708618 B1 | 3/1997 |
| EP | 0770355 A1 | 5/1997 |
| EP | 0503662 B1 | 6/1997 |
| EP | 0447121 B1 | 7/1997 |
| EP | 0625077 B1 | 7/1997 |
| EP | 0633749 B1 | 8/1997 |
| EP | 0710090 B1 | 8/1997 |
| EP | 0578425 B1 | 9/1997 |
| EP | 0625335 B1 | 11/1997 |
| EP | 0552423 B1 | 1/1998 |
| EP | 0592244 B1 | 1/1998 |
| EP | 0648476 B1 | 1/1998 |
| EP | 0649290 B1 | 3/1998 |
| EP | 0598618 B1 | 9/1998 |
| EP | 0676173 B1 | 9/1998 |
| EP | 0678007 B1 | 9/1998 |
| EP | 0603472 B1 | 11/1998 |
| EP | 0605351 B1 | 11/1998 |
| EP | 0878169 A1 | 11/1998 |
| EP | 0879742 A1 | 11/1998 |
| EP | 0695144 B1 | 12/1998 |
| EP | 0722296 B1 | 12/1998 |
| EP | 0760230 B1 | 2/1999 |
| EP | 0623316 B1 | 3/1999 |
| EP | 0650701 B1 | 3/1999 |
| EP | 0537572 B1 | 6/1999 |
| EP | 0923907 A1 | 6/1999 |
| EP | 0843906 B1 | 3/2000 |
| EP | 0552050 B1 | 5/2000 |
| EP | 0833592 B1 | 5/2000 |
| EP | 0830094 B1 | 9/2000 |
| EP | 1034747 A1 | 9/2000 |
| EP | 1034748 A1 | 9/2000 |
| EP | 0694290 B1 | 11/2000 |
| EP | 1050278 A1 | 11/2000 |
| EP | 1053719 A1 | 11/2000 |
| EP | 1053720 A1 | 11/2000 |
| EP | 1055399 A1 | 11/2000 |
| EP | 1055400 A1 | 11/2000 |
| EP | 1080694 A1 | 3/2001 |
| EP | 1090592 A1 | 4/2001 |
| EP | 1095627 A1 | 5/2001 |
| EP | 1256318 B1 | 5/2001 |
| EP | 0806914 B1 | 9/2001 |
| EP | 0768840 B1 | 12/2001 |
| EP | 0908152 B1 | 1/2002 |
| EP | 0872213 B1 | 5/2002 |
| EP | 0862386 B1 | 6/2002 |
| EP | 0949886 B1 | 9/2002 |
| EP | 1238634 A2 | 9/2002 |
| EP | 0858295 B1 | 12/2002 |
| EP | 0656188 B1 | 1/2003 |
| EP | 0717960 B1 | 2/2003 |
| EP | 1284120 A1 | 2/2003 |
| EP | 1287788 A1 | 3/2003 |
| EP | 0717966 B1 | 4/2003 |
| EP | 0869742 B1 | 5/2003 |
| EP | 0829235 B1 | 6/2003 |
| EP | 0887046 B1 | 7/2003 |
| EP | 0852480 B1 | 8/2003 |
| EP | 0891154 B1 | 9/2003 |
| EP | 0813843 B1 | 10/2003 |
| EP | 0873089 B1 | 10/2003 |
| EP | 0856326 B1 | 11/2003 |
| EP | 1374788 A1 | 1/2004 |
| EP | 0741996 B1 | 2/2004 |
| EP | 0814712 B1 | 2/2004 |
| EP | 1402837 A1 | 3/2004 |
| EP | 0705570 B1 | 4/2004 |
| EP | 0959784 B1 | 4/2004 |
| EP | 1407719 A2 | 4/2004 |
| EP | 1086713 B1 | 5/2004 |
| EP | 0996378 B1 | 6/2004 |
| EP | 1426012 A1 | 6/2004 |
| EP | 0833593 B2 | 7/2004 |
| EP | 1442694 A1 | 8/2004 |
| EP | 0888749 B1 | 9/2004 |
| EP | 0959786 B1 | 9/2004 |
| EP | 1459695 A1 | 9/2004 |
| EP | 1254636 B1 | 10/2004 |
| EP | 1473819 A1 | 11/2004 |
| EP | 1477119 A1 | 11/2004 |
| EP | 1479345 A1 | 11/2004 |
| EP | 1479347 A1 | 11/2004 |
| EP | 1479348 A1 | 11/2004 |
| EP | 0754437 B2 | 12/2004 |
| EP | 1025807 B1 | 12/2004 |
| EP | 1001710 B1 | 1/2005 |
| EP | 1520521 A1 | 4/2005 |
| EP | 1520522 A1 | 4/2005 |
| EP | 1520523 A1 | 4/2005 |
| EP | 1520525 A1 | 4/2005 |
| EP | 1522264 A1 | 4/2005 |
| EP | 1523942 A2 | 4/2005 |
| EP | 1550408 A1 | 7/2005 |
| EP | 1557129 A1 | 7/2005 |
| EP | 1064883 B1 | 8/2005 |
| EP | 1067876 B1 | 8/2005 |
| EP | 0870473 B1 | 9/2005 |
| EP | 1157666 B1 | 9/2005 |
| EP | 0880338 B1 | 10/2005 |
| EP | 1158917 B1 | 11/2005 |
| EP | 1344498 B1 | 11/2005 |
| EP | 0906764 B1 | 12/2005 |
| EP | 1330989 B1 | 12/2005 |
| EP | 0771176 B2 | 1/2006 |
| EP | 1621138 A2 | 2/2006 |
| EP | 1621139 A2 | 2/2006 |

(56) References Cited

FOREIGN PATENT DOCUMENTS

| | | | |
|---|---|---|---|
| EP | 1621141 | A2 | 2/2006 |
| EP | 1621145 | A2 | 2/2006 |
| EP | 1621151 | A2 | 2/2006 |
| EP | 1034746 | B1 | 3/2006 |
| EP | 1201196 | B1 | 3/2006 |
| EP | 1632191 | A2 | 3/2006 |
| EP | 1647231 | A1 | 4/2006 |
| EP | 1065981 | B1 | 5/2006 |
| EP | 1082944 | B1 | 5/2006 |
| EP | 1652481 | A2 | 5/2006 |
| EP | 1382303 | B1 | 6/2006 |
| EP | 1253866 | B1 | 7/2006 |
| EP | 1032318 | B1 | 8/2006 |
| EP | 1045672 | B1 | 8/2006 |
| EP | 1617768 | B1 | 8/2006 |
| EP | 1693015 | A2 | 8/2006 |
| EP | 1400214 | B1 | 9/2006 |
| EP | 1702567 | A2 | 9/2006 |
| EP | 1129665 | B1 | 11/2006 |
| EP | 1400206 | B1 | 11/2006 |
| EP | 1721568 | A1 | 11/2006 |
| EP | 1256317 | B1 | 12/2006 |
| EP | 1285633 | B1 | 12/2006 |
| EP | 1728473 | A1 | 12/2006 |
| EP | 1728475 | A2 | 12/2006 |
| EP | 1479346 | B1 | 1/2007 |
| EP | 1484024 | B1 | 1/2007 |
| EP | 1754445 | A2 | 2/2007 |
| EP | 1759812 | A1 | 3/2007 |
| EP | 1767163 | A1 | 3/2007 |
| EP | 1769756 | A1 | 4/2007 |
| EP | 1769758 | A1 | 4/2007 |
| EP | 1581128 | B1 | 5/2007 |
| EP | 1780825 | A1 | 5/2007 |
| EP | 1785097 | A2 | 5/2007 |
| EP | 1790293 | A2 | 5/2007 |
| EP | 1800610 | A1 | 6/2007 |
| EP | 1300117 | B1 | 8/2007 |
| EP | 1813199 | A1 | 8/2007 |
| EP | 1813200 | A2 | 8/2007 |
| EP | 1813201 | A1 | 8/2007 |
| EP | 1813202 | A1 | 8/2007 |
| EP | 1813203 | A2 | 8/2007 |
| EP | 1813207 | A1 | 8/2007 |
| EP | 1813209 | A1 | 8/2007 |
| EP | 1837041 | A1 | 9/2007 |
| EP | 0922435 | B1 | 10/2007 |
| EP | 1487359 | B1 | 10/2007 |
| EP | 1599146 | B1 | 10/2007 |
| EP | 1839596 | A1 | 10/2007 |
| EP | 2110083 | A2 | 10/2007 |
| EP | 1857057 | A2 | 11/2007 |
| EP | 1402821 | B1 | 12/2007 |
| EP | 1872727 | A1 | 1/2008 |
| EP | 1671593 | B1 | 2/2008 |
| EP | 1897502 | A1 | 3/2008 |
| EP | 1611856 | B1 | 4/2008 |
| EP | 1908417 | A2 | 4/2008 |
| EP | 1330201 | B1 | 6/2008 |
| EP | 1702568 | B1 | 7/2008 |
| EP | 1943955 | A2 | 7/2008 |
| EP | 1943957 | A2 | 7/2008 |
| EP | 1943964 | A1 | 7/2008 |
| EP | 1943976 | A2 | 7/2008 |
| EP | 1593337 | B1 | 8/2008 |
| EP | 1970014 | A1 | 9/2008 |
| EP | 1980213 | A2 | 10/2008 |
| EP | 1759645 | B1 | 11/2008 |
| EP | 1990014 | A2 | 11/2008 |
| EP | 1552795 | B1 | 12/2008 |
| EP | 1693008 | B1 | 12/2008 |
| EP | 1759640 | B1 | 12/2008 |
| EP | 1997439 | A2 | 12/2008 |
| EP | 2000102 | A2 | 12/2008 |
| EP | 2005894 | A2 | 12/2008 |
| EP | 2008595 | A2 | 12/2008 |
| EP | 1736104 | B1 | 3/2009 |
| EP | 1749486 | B1 | 3/2009 |
| EP | 2039302 | A2 | 3/2009 |
| EP | 2039316 | A2 | 3/2009 |
| EP | 1721576 | B1 | 4/2009 |
| EP | 1733686 | B1 | 4/2009 |
| EP | 2044890 | A1 | 4/2009 |
| EP | 1550409 | A1 | 6/2009 |
| EP | 1550413 | B1 | 6/2009 |
| EP | 1719461 | B1 | 6/2009 |
| EP | 1745748 | B1 | 8/2009 |
| EP | 2090237 | A1 | 8/2009 |
| EP | 2090241 | A1 | 8/2009 |
| EP | 2090244 | A2 | 8/2009 |
| EP | 2090245 | A1 | 8/2009 |
| EP | 2090256 | A2 | 8/2009 |
| EP | 2095777 | A2 | 9/2009 |
| EP | 2098170 | A2 | 9/2009 |
| EP | 2110082 | A1 | 10/2009 |
| EP | 2111803 | A2 | 10/2009 |
| EP | 1813208 | B1 | 11/2009 |
| EP | 1908426 | B1 | 11/2009 |
| EP | 2116195 | A1 | 11/2009 |
| EP | 1607050 | B1 | 12/2009 |
| EP | 1815804 | B1 | 12/2009 |
| EP | 1875870 | B1 | 12/2009 |
| EP | 2151204 | A1 | 2/2010 |
| EP | 2165660 | A2 | 3/2010 |
| EP | 1566150 | B1 | 4/2010 |
| EP | 1813206 | B1 | 4/2010 |
| EP | 1769754 | B1 | 6/2010 |
| EP | 1854416 | B1 | 6/2010 |
| EP | 2198787 | A1 | 6/2010 |
| EP | 1647286 | B1 | 9/2010 |
| EP | 1535565 | B1 | 10/2010 |
| EP | 1702570 | B1 | 10/2010 |
| EP | 1785098 | B1 | 10/2010 |
| EP | 2005896 | A2 | 10/2010 |
| EP | 2030578 | B1 | 11/2010 |
| EP | 1627605 | B1 | 12/2010 |
| EP | 1994890 | B1 | 1/2011 |
| EP | 2286738 | A2 | 2/2011 |
| EP | 1690502 | B1 | 3/2011 |
| EP | 2292153 | A1 | 3/2011 |
| EP | 1769755 | B1 | 4/2011 |
| EP | 2090240 | B1 | 4/2011 |
| EP | 2305135 | A1 | 4/2011 |
| EP | 1813205 | B1 | 6/2011 |
| EP | 2090243 | B1 | 6/2011 |
| EP | 2329773 | A1 | 6/2011 |
| EP | 1908414 | B1 | 11/2011 |
| EP | 2153781 | B1 | 11/2011 |
| EP | 1847225 | B1 | 12/2011 |
| EP | 1785102 | B1 | 1/2012 |
| EP | 2090253 | B1 | 3/2012 |
| EP | 2005895 | B1 | 8/2012 |
| EP | 2090248 | B1 | 8/2012 |
| EP | 2090252 | B1 | 10/2012 |
| EP | 2517637 | A1 | 10/2012 |
| EP | 2517645 | A2 | 10/2012 |
| EP | 2517649 | A2 | 10/2012 |
| EP | 2517651 | A2 | 10/2012 |
| EP | 1884206 | B1 | 3/2013 |
| FR | 459743 | A | 11/1913 |
| FR | 999646 | A | 2/1952 |
| FR | 1112936 | A | 3/1956 |
| FR | 2598905 | A1 | 11/1987 |
| FR | 2765794 | A | 1/1999 |
| GB | 939929 | A | 10/1963 |
| GB | 1210522 | A | 10/1970 |
| GB | 1217159 | A | 12/1970 |
| GB | 1339394 | A | 12/1973 |
| GB | 2109241 | A | 6/1983 |
| GB | 2272159 | A | 5/1994 |
| GB | 2284242 | A | 5/1995 |
| GB | 2336214 | A | 10/1999 |
| GB | 2425903 | A | 11/2006 |
| JP | 50-33988 | U | 4/1975 |

(56) References Cited

FOREIGN PATENT DOCUMENTS

| | | |
|---|---|---|
| JP | S 5850053 A | 1/1983 |
| JP | 61-98249 A | 5/1986 |
| JP | S 61502036 A | 9/1986 |
| JP | S 63-59764 | 3/1988 |
| JP | S 63-147449 A | 6/1988 |
| JP | 63-203149 | 8/1988 |
| JP | H 02-279149 A | 11/1990 |
| JP | 3-12126 A | 1/1991 |
| JP | H 05-084242 A | 4/1993 |
| JP | 5-212039 A | 8/1993 |
| JP | 6007357 A | 1/1994 |
| JP | H 6-30945 A | 2/1994 |
| JP | H 06-26812 U | 4/1994 |
| JP | H 6-121798 A | 5/1994 |
| JP | 7051273 A | 2/1995 |
| JP | 7-124166 A | 5/1995 |
| JP | 7-255735 A | 10/1995 |
| JP | 8-33642 A | 2/1996 |
| JP | 8033641 A | 2/1996 |
| JP | 8-164141 A | 6/1996 |
| JP | H 08-182684 A | 7/1996 |
| JP | 8229050 A | 9/1996 |
| JP | H 09-501081 A | 2/1997 |
| JP | 2000-14632 | 1/2000 |
| JP | 2000033071 A | 2/2000 |
| JP | 2000-112002 A | 4/2000 |
| JP | 2000171730 A | 6/2000 |
| JP | 2000287987 A | 10/2000 |
| JP | 2000325303 A | 11/2000 |
| JP | 2001-514541 A | 9/2001 |
| JP | 2001-517473 A | 10/2001 |
| JP | 2001286477 A | 10/2001 |
| JP | 2002143078 A | 5/2002 |
| JP | 2002369820 A | 12/2002 |
| JP | 2003-500153 A | 1/2003 |
| JP | 2003-164066 | 6/2003 |
| JP | 2003-521301 A | 7/2003 |
| JP | 2004-162035 A | 6/2004 |
| JP | 2004-531280 A | 10/2004 |
| JP | 2004-532084 A | 10/2004 |
| JP | 2004-329624 A | 11/2004 |
| JP | 2004-344663 | 12/2004 |
| JP | 2005-028147 A | 2/2005 |
| JP | 2005-28148 A | 2/2005 |
| JP | 2005-028149 A | 2/2005 |
| JP | 2005-505309 A | 2/2005 |
| JP | 2005505322 A | 2/2005 |
| JP | 2005-103280 A | 4/2005 |
| JP | 2005-103281 A | 4/2005 |
| JP | 2005-511131 A | 4/2005 |
| JP | 2005103293 A | 4/2005 |
| JP | 2005131163 A | 5/2005 |
| JP | 2005131164 A | 5/2005 |
| JP | 2005131173 A | 5/2005 |
| JP | 2005131211 A | 5/2005 |
| JP | 2005131212 A | 5/2005 |
| JP | 2005-144183 A | 6/2005 |
| JP | 2005137423 A | 6/2005 |
| JP | 2005152416 A | 6/2005 |
| JP | 2005-523105 A | 8/2005 |
| JP | 2005524474 A | 8/2005 |
| JP | 2006-034975 A | 2/2006 |
| JP | 2006-034980 A | 2/2006 |
| JP | 2006-506106 A | 2/2006 |
| JP | 2006-218297 A | 8/2006 |
| JP | 2006-281405 A | 10/2006 |
| JP | 2006-346445 A | 12/2006 |
| JP | 2007-098130 A | 4/2007 |
| JP | 3906843 B2 | 4/2007 |
| JP | 2007-117725 A | 5/2007 |
| JP | 2007-222615 A | 6/2007 |
| JP | 2007-203051 A | 8/2007 |
| JP | 2007-203057 A | 8/2007 |
| JP | 2007/524435 A | 8/2007 |
| JP | 2007-229448 A | 9/2007 |
| JP | 2007-325922 A | 12/2007 |
| JP | 2008-68073 A | 3/2008 |
| JP | 2008-283459 A | 11/2008 |
| JP | 2009-506799 A | 2/2009 |
| JP | 2010-098844 A | 4/2010 |
| RU | 2008830 C1 | 3/1994 |
| RU | 2141279 C1 | 11/1999 |
| RU | 2187249 C2 | 8/2002 |
| RU | 2189091 C2 | 9/2002 |
| RU | 2225170 C2 | 3/2004 |
| SU | 189517 A | 1/1967 |
| SU | 328636 A | 9/1972 |
| SU | 674747 A1 | 7/1979 |
| SU | 1009439 A | 4/1983 |
| SU | 1022703 A1 | 6/1983 |
| SU | 1333319 A2 | 8/1987 |
| SU | 886900 A1 | 12/1987 |
| SU | 1377053 A1 | 2/1988 |
| SU | 1509051 A1 | 9/1989 |
| SU | 1561964 A1 | 5/1990 |
| SU | 1708312 A1 | 1/1992 |
| SU | 1722476 A1 | 3/1992 |
| SU | 1752361 A1 | 8/1992 |
| SU | 1814161 A1 | 5/1993 |
| WO | WO 82/02824 A1 | 9/1982 |
| WO | WO 91/15157 A1 | 10/1991 |
| WO | WO 92/20295 A1 | 11/1992 |
| WO | WO 92/21300 A1 | 12/1992 |
| WO | WO 93/08755 A1 | 5/1993 |
| WO | WO 93/13718 A1 | 7/1993 |
| WO | WO 93/14690 A1 | 8/1993 |
| WO | WO 93/15648 A1 | 8/1993 |
| WO | WO 93/15850 A1 | 8/1993 |
| WO | WO 93/19681 A1 | 10/1993 |
| WO | WO 94/00060 A1 | 1/1994 |
| WO | WO 94/11057 A1 | 5/1994 |
| WO | WO 94/12108 A1 | 6/1994 |
| WO | WO 94/18893 A1 | 9/1994 |
| WO | WO 94/22378 A1 | 10/1994 |
| WO | WO 94/23659 A1 | 10/1994 |
| WO | WO 94/24943 A1 | 11/1994 |
| WO | WO 94-24947 A1 | 11/1994 |
| WO | WO 95/02369 A1 | 1/1995 |
| WO | WO 95/03743 A1 | 2/1995 |
| WO | WO 95/06817 A1 | 3/1995 |
| WO | WO 95/09576 A1 | 4/1995 |
| WO | WO 95/09577 A1 | 4/1995 |
| WO | WO 95/14436 A1 | 6/1995 |
| WO | WO 95/17855 A1 | 7/1995 |
| WO | WO 95/18383 A1 | 7/1995 |
| WO | WO 95/18572 A1 | 7/1995 |
| WO | WO 95/19739 A1 | 7/1995 |
| WO | WO 95/20360 A1 | 8/1995 |
| WO | WO 95/23557 A1 | 9/1995 |
| WO | WO 95/24865 A1 | 9/1995 |
| WO | WO 95/25471 A3 | 9/1995 |
| WO | WO 95/26562 A1 | 10/1995 |
| WO | WO 95/29639 A1 | 11/1995 |
| WO | WO 96/04858 A1 | 2/1996 |
| WO | WO 96/18344 A2 | 6/1996 |
| WO | WO 96/19151 A1 | 6/1996 |
| WO | WO 96/19152 A1 | 6/1996 |
| WO | WO 96/20652 A1 | 7/1996 |
| WO | WO 96/21119 A1 | 7/1996 |
| WO | WO 96/22055 A1 | 7/1996 |
| WO | WO 96/23448 A1 | 8/1996 |
| WO | WO 96/24301 A1 | 8/1996 |
| WO | WO 96/27337 A1 | 9/1996 |
| WO | WO 96/31155 A1 | 10/1996 |
| WO | WO 96/35464 A1 | 11/1996 |
| WO | WO 96/39085 A1 | 12/1996 |
| WO | WO 96/39086 A1 | 12/1996 |
| WO | WO 96/39087 A1 | 12/1996 |
| WO | WO 96/39088 A1 | 12/1996 |
| WO | WO 96/39089 A1 | 12/1996 |
| WO | WO 97/00646 A1 | 1/1997 |
| WO | WO 97/00647 A1 | 1/1997 |
| WO | WO 97/01989 A1 | 1/1997 |
| WO | WO 97/06582 A1 | 2/1997 |

(56) References Cited

FOREIGN PATENT DOCUMENTS

| | | |
|---|---|---|
| WO | WO 97/10763 A1 | 3/1997 |
| WO | WO 97/10764 A1 | 3/1997 |
| WO | WO 97/11648 A2 | 4/1997 |
| WO | WO 97/11649 A1 | 4/1997 |
| WO | WO 97/15237 A1 | 5/1997 |
| WO | WO 97/24073 A1 | 7/1997 |
| WO | WO 97/24993 A1 | 7/1997 |
| WO | WO 97/30644 A1 | 8/1997 |
| WO | WO 97/34533 A1 | 9/1997 |
| WO | WO 97/37598 A1 | 10/1997 |
| WO | WO 97/39688 A2 | 10/1997 |
| WO | WO 98/17180 A1 | 4/1998 |
| WO | WO 98/27880 A1 | 7/1998 |
| WO | WO 98/30153 A1 | 7/1998 |
| WO | WO 98/47436 A1 | 10/1998 |
| WO | WO 99/03407 A1 | 1/1999 |
| WO | WO 99/03408 A1 | 1/1999 |
| WO | WO 99/03409 A1 | 1/1999 |
| WO | WO 99/12483 A1 | 3/1999 |
| WO | WO 99/12487 A1 | 3/1999 |
| WO | WO 99/12488 A1 | 3/1999 |
| WO | WO 99/15086 A1 | 4/1999 |
| WO | WO 99/15091 A1 | 4/1999 |
| WO | WO 99/23933 A2 | 5/1999 |
| WO | WO 99/23959 A1 | 5/1999 |
| WO | WO 99/25261 A1 | 5/1999 |
| WO | WO 99/29244 A1 | 6/1999 |
| WO | WO 99/34744 A1 | 7/1999 |
| WO | WO 99/45849 A1 | 9/1999 |
| WO | WO 99/48430 A1 | 9/1999 |
| WO | WO 99/51158 A1 | 10/1999 |
| WO | WO 00/24322 A1 | 5/2000 |
| WO | WO 00/24330 A1 | 5/2000 |
| WO | WO 00/41638 A1 | 7/2000 |
| WO | WO 00/48506 A1 | 8/2000 |
| WO | WO 00/53112 A2 | 9/2000 |
| WO | WO 00/54653 A1 | 9/2000 |
| WO | WO 00/57796 A1 | 10/2000 |
| WO | WO 00/64365 A1 | 11/2000 |
| WO | WO 00/72762 A1 | 12/2000 |
| WO | WO 00/72765 A1 | 12/2000 |
| WO | WO 01/03587 A1 | 1/2001 |
| WO | WO 01/05702 A1 | 1/2001 |
| WO | WO 01/10482 A1 | 2/2001 |
| WO | WO 01/35845 A1 | 5/2001 |
| WO | WO 01/54594 A1 | 8/2001 |
| WO | WO 01/58371 A1 | 8/2001 |
| WO | WO 01/62158 A2 | 8/2001 |
| WO | WO 01/62161 A1 | 8/2001 |
| WO | WO 01/62162 A1 | 8/2001 |
| WO | WO 01/62164 A2 | 8/2001 |
| WO | WO 01/62169 A2 | 8/2001 |
| WO | WO 01/78605 A2 | 10/2001 |
| WO | WO 01/91646 A1 | 12/2001 |
| WO | WO 02/00121 A1 | 1/2002 |
| WO | WO 02/07608 A2 | 1/2002 |
| WO | WO 02/07618 A1 | 1/2002 |
| WO | WO 02/17799 A1 | 3/2002 |
| WO | WO 02/19920 A1 | 3/2002 |
| WO | WO 02/19932 A1 | 3/2002 |
| WO | WO 02/30297 A2 | 4/2002 |
| WO | WO 02/32322 A2 | 4/2002 |
| WO | WO 02/36028 A1 | 5/2002 |
| WO | WO 02/43571 A2 | 6/2002 |
| WO | WO 02/058568 A1 | 8/2002 |
| WO | WO 02/060328 A1 | 8/2002 |
| WO | WO 02/067785 A2 | 9/2002 |
| WO | WO 02/098302 A1 | 12/2002 |
| WO | WO 03/000138 A2 | 1/2003 |
| WO | WO 03/001329 A2 | 1/2003 |
| WO | WO 03/013363 A1 | 2/2003 |
| WO | WO 03/013372 A2 | 2/2003 |
| WO | WO 03/015604 A2 | 2/2003 |
| WO | WO 03/020106 A2 | 3/2003 |
| WO | WO 03/020139 A2 | 3/2003 |
| WO | WO 03/024339 A1 | 3/2003 |
| WO | WO 03/079909 A3 | 3/2003 |
| WO | WO 03/030743 A2 | 4/2003 |
| WO | WO 03/037193 A1 | 5/2003 |
| WO | WO 03/047436 A3 | 6/2003 |
| WO | WO 03/055402 A1 | 7/2003 |
| WO | WO 03/057048 A1 | 7/2003 |
| WO | WO 03/057058 A1 | 7/2003 |
| WO | WO 03/063694 A1 | 8/2003 |
| WO | WO 03/077769 A1 | 9/2003 |
| WO | WO 03/079911 A1 | 10/2003 |
| WO | WO 03/082126 A1 | 10/2003 |
| WO | WO 03/086206 A1 | 10/2003 |
| WO | WO 03/088845 A2 | 10/2003 |
| WO | WO 03/090630 A2 | 11/2003 |
| WO | WO 03/094743 A1 | 11/2003 |
| WO | WO 03/094745 A1 | 11/2003 |
| WO | WO 03/094746 A1 | 11/2003 |
| WO | WO 03/094747 A1 | 11/2003 |
| WO | WO 03/101313 A1 | 12/2003 |
| WO | WO 03/105698 A2 | 12/2003 |
| WO | WO 03/105702 A2 | 12/2003 |
| WO | WO 2004/006980 A2 | 1/2004 |
| WO | WO 2004/011037 A2 | 2/2004 |
| WO | WO 2004/019769 A1 | 3/2004 |
| WO | WO 2004/019803 A1 | 3/2004 |
| WO | WO 2004/021868 A2 | 3/2004 |
| WO | WO 2004/028585 A2 | 4/2004 |
| WO | WO 2004/032754 A2 | 4/2004 |
| WO | WO 2004/032760 A2 | 4/2004 |
| WO | WO 2004/032762 A1 | 4/2004 |
| WO | WO 2004/032763 A2 | 4/2004 |
| WO | WO 2004/034875 A2 | 4/2004 |
| WO | WO 2004/047626 A1 | 6/2004 |
| WO | WO 2004/047653 A2 | 6/2004 |
| WO | WO 2004/049956 A2 | 6/2004 |
| WO | WO 2004/052426 A2 | 6/2004 |
| WO | WO 2004/056276 A1 | 7/2004 |
| WO | WO 2004/056277 A1 | 7/2004 |
| WO | WO 2004/062516 A1 | 7/2004 |
| WO | WO 2004/078050 A2 | 9/2004 |
| WO | WO 2004/078051 A2 | 9/2004 |
| WO | WO 2004/078236 A2 | 9/2004 |
| WO | WO 2004/086987 A1 | 10/2004 |
| WO | WO 2004/096015 A2 | 11/2004 |
| WO | WO 2004/096057 A2 | 11/2004 |
| WO | WO 2004/103157 A2 | 12/2004 |
| WO | WO 2004/105593 A1 | 12/2004 |
| WO | WO 2004/105621 A1 | 12/2004 |
| WO | WO 2004/112618 A2 | 12/2004 |
| WO | WO 2004/112652 A2 | 12/2004 |
| WO | WO 2005/027983 A2 | 3/2005 |
| WO | WO 2005/037329 A2 | 4/2005 |
| WO | WO 2005/044078 A2 | 5/2005 |
| WO | WO 2005/055846 A1 | 6/2005 |
| WO | WO 2005/072634 A2 | 8/2005 |
| WO | WO 2005/078892 A1 | 8/2005 |
| WO | WO 2005/079675 A2 | 9/2005 |
| WO | WO 2005/096954 A2 | 10/2005 |
| WO | WO 2005/112806 A2 | 12/2005 |
| WO | WO 2005/112808 A1 | 12/2005 |
| WO | WO 2005/115251 A2 | 12/2005 |
| WO | WO 2005/115253 A2 | 12/2005 |
| WO | WO 2005/117735 A1 | 12/2005 |
| WO | WO 2005/122936 A1 | 12/2005 |
| WO | WO 2006/023486 A1 | 3/2006 |
| WO | WO 2006/023578 A2 | 3/2006 |
| WO | WO 2006/027014 A1 | 3/2006 |
| WO | WO 2006/044490 A2 | 4/2006 |
| WO | WO 2006/044581 A2 | 4/2006 |
| WO | WO 2006/044810 A2 | 4/2006 |
| WO | WO 2006/051252 A1 | 5/2006 |
| WO | WO 2006/059067 A1 | 6/2006 |
| WO | WO 2006/083748 A1 | 8/2006 |
| WO | WO 2006/092563 A1 | 9/2006 |
| WO | WO 2006/092565 A1 | 9/2006 |
| WO | WO 2006/115958 A1 | 11/2006 |
| WO | WO 2006/125940 A1 | 11/2006 |
| WO | WO 2006/132992 A1 | 12/2006 |

(56) References Cited

FOREIGN PATENT DOCUMENTS

| | | |
|---|---|---|
| WO | WO 2007/002180 A2 | 1/2007 |
| WO | WO 2007/016290 A2 | 2/2007 |
| WO | WO 2007/018898 A2 | 2/2007 |
| WO | WO 2007/098220 A2 | 8/2007 |
| WO | WO 2007/121579 A1 | 11/2007 |
| WO | WO 2007/131110 A2 | 11/2007 |
| WO | WO 2007/137304 A2 | 11/2007 |
| WO | WO 2007/139734 A2 | 12/2007 |
| WO | WO 2007/142625 A2 | 12/2007 |
| WO | WO 2007/147439 A1 | 12/2007 |
| WO | WO 2008/021969 A2 | 2/2008 |
| WO | WO 2008/039249 A1 | 4/2008 |
| WO | WO 2008/039270 A1 | 4/2008 |
| WO | WO 2008/045383 A2 | 4/2008 |
| WO | WO 2008/057281 A2 | 5/2008 |
| WO | WO 2008/070763 A1 | 6/2008 |
| WO | WO 2008/089404 A2 | 7/2008 |
| WO | WO 2008/101080 A1 | 8/2008 |
| WO | WO 2008/109125 A1 | 9/2008 |
| WO | WO 2008/124748 A1 | 10/2008 |
| WO | WO 2009/023851 A1 | 2/2009 |
| WO | WO 2009/046394 A1 | 4/2009 |
| WO | WO 2009/137761 A2 | 11/2009 |
| WO | WO 2009/143092 A1 | 11/2009 |
| WO | WO 2010/028332 A2 | 3/2010 |
| WO | WO 2010/030434 A1 | 3/2010 |
| WO | WO 2010/054404 A1 | 5/2010 |
| WO | WO 2010/063795 A1 | 6/2010 |
| WO | WO 2010/098871 A2 | 9/2010 |
| WO | WO 2012/021671 A1 | 2/2012 |
| WO | WO 2012/044820 A1 | 4/2012 |
| WO | WO 2012/044844 A2 | 4/2012 |

OTHER PUBLICATIONS

International Search Report for PCT/US2012/028886, dated Nov. 23, 2012 (6 pages).

Disclosed Anonymously, "Motor-Driven Surgical Stapler Improvements," Research Disclosure Database No. 526041, Published: Feb. 2008.

C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.

B.R. Coolman, DVM , MS et al., "Comparison of Skin Staples With Sutures for Anastomosis of the Small Intestine in Dogs," Abstract; http://www.blackwell-synergy.com/doi/abs/10.1053/jvet.2000. 7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).

The Sodem Aseptic Battery Transfer Kit, Sodem Systems, (2000), 3 pages.

"Biomedical Coatings," Fort Wayne Metals, Research Products Corporation, obtained online at www.fwmetals.com on Jun. 21, 2010 (1 page).

Van Meer et al., "A Disposable Plastic Compact Wrist for Smart Minimally Invasive Surgical Tools," LAAS/CNRS (Aug. 2005).

Breedveld et al., "A New, Easily Miniaturized Sterrable Endoscope," IEEE Engineering in Medicine and Biology Magazine (Nov./Dec. 2005).

D. Tuite, Ed., "Get the Lowdown on Ultracapacitors," Nov. 15, 2007; [online] URL: http://electronicdesign.com/Articles/Print.cfm?ArticleID=17465, accessed Jan. 15, 2008 (5 pages).

Datasheet for Panasonic TK Relays Ultra Low Profile 2 A Polarized Relay, Copyright Matsushita Electric Works, Ltd. (Known of at least as early as Aug. 17, 2010), 5 pages.

ASTM procedure D2240-00, "Standard Test Method for Rubber Property-Durometer Hardness," (Published Aug. 2000).

ASTM procedure D2240-05, "Standard Test Method for Rubber Property-Durometer Hardness," (Published Apr. 2010).

Covidien Brochure, "Endo GIA™ Reloads with Tri-Staple™ Technology," (2010), 1 page.

Covidien Brochure, "Endo GIA™ Reloads with Tri-Staple™ Technology and Endo GIA™ Ultra Universal Staplers," (2010), 2 pages.

Covidien Brochure, "Endo GIA™ Black Reload with Tri-Staple™ Technology," (2012), 2 pages.

Covidien Brochure, "Endo GIA™ Curved Tip Reload with Tri-Staple™ Technology," (2012), 2 pages.

Covidien Brochure, "Endo GIA™ Reloads with Tri-Stapler™ Technology," (2010), 2 pages.

Covidien Brochure, "Endo GIA™ Ultra Universal Stapler," (2010), 2 pages.

Miyata et al., "Biomolecule-Sensitive Hydrogels," Advanced Drug Delivery Reviews, 54 (2002) pp. 79-98.

Jeong et al., "Thermosensitive Sol-Gel Reversible Hydrogels," Advanced Drug Delivery Reviews, 54 (2002) pp. 37-51.

Byrne et al., "Molecular Imprinting Within Hydrogels," Advanced Drug Delivery Reviews, 54 (2002) pp. 149-161.

Qiu et al., "Environment-Sensitive Hydrogels for Drug Delivery," Advanced Drug Delivery Reviews, 53 (2001) pp. 321-339.

Hoffman, "Hydrogels for Biomedical Applications," Advanced Drug Delivery Reviews, 43 (2002) pp. 30-12.

Hoffman, "Hydrogels for Biomedical Applications," Advanced Drug Delivery Reviews, 54 (2002) pp. 30-12.

Peppas, "Physiologically Responsive Hydrogels," Journal of Bioactive and Compatible Polymers, vol. 6 (Jul. 1991) pp. 241-246.

Ebara, "Carbohydrate-Derived Hydrogels and Microgels," Engineered Carbohydrate-Based Materials for Biomedical Applications: Polymers, Surfaes, Dendrimers, Nanoparticles, and Hydrogels, Edited by Ravin Narain, 2011, pp. 337-345.

Peppas, Editor "Hydrogels in Medicine and Pharmacy," vol. I, Fundamentals, CRC Press, 1986.

* cited by examiner

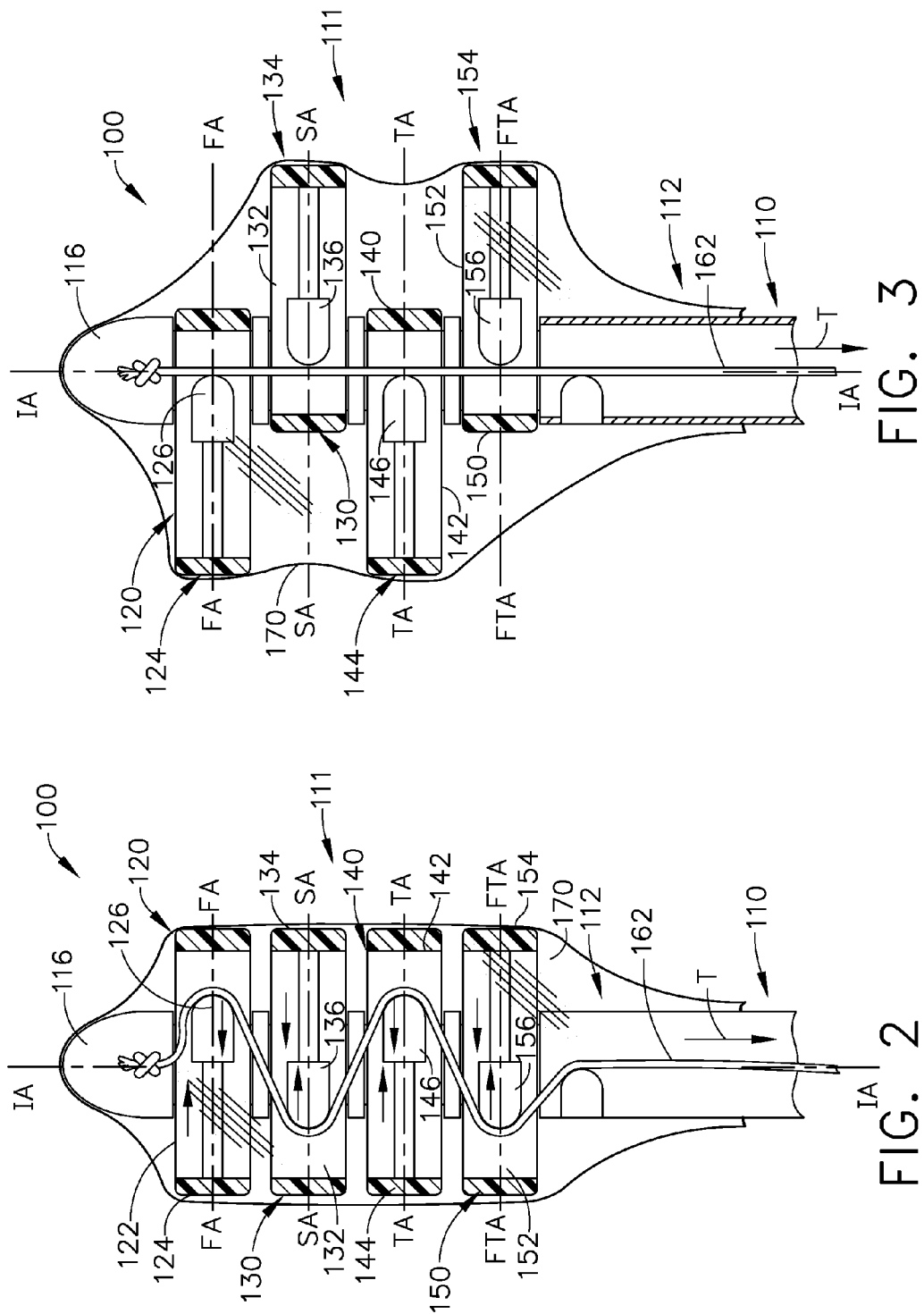

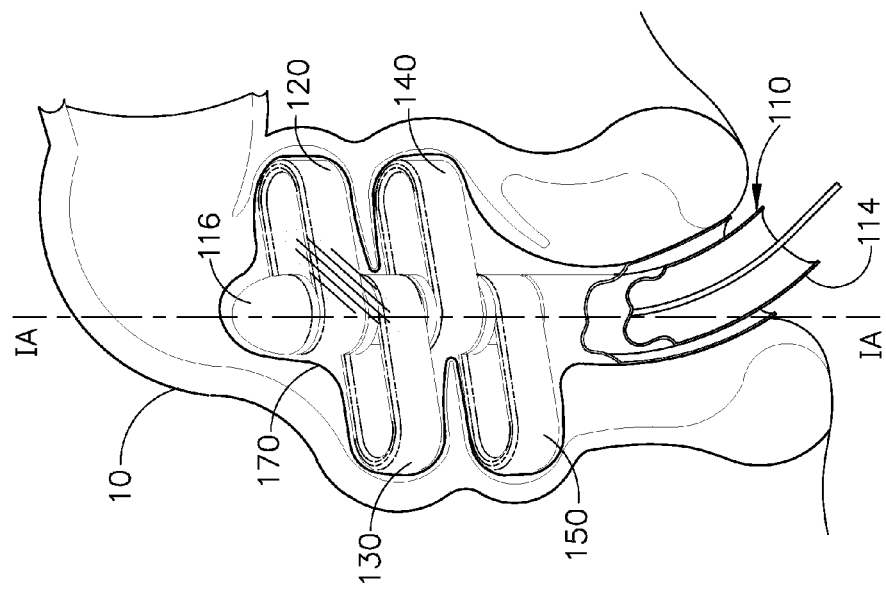
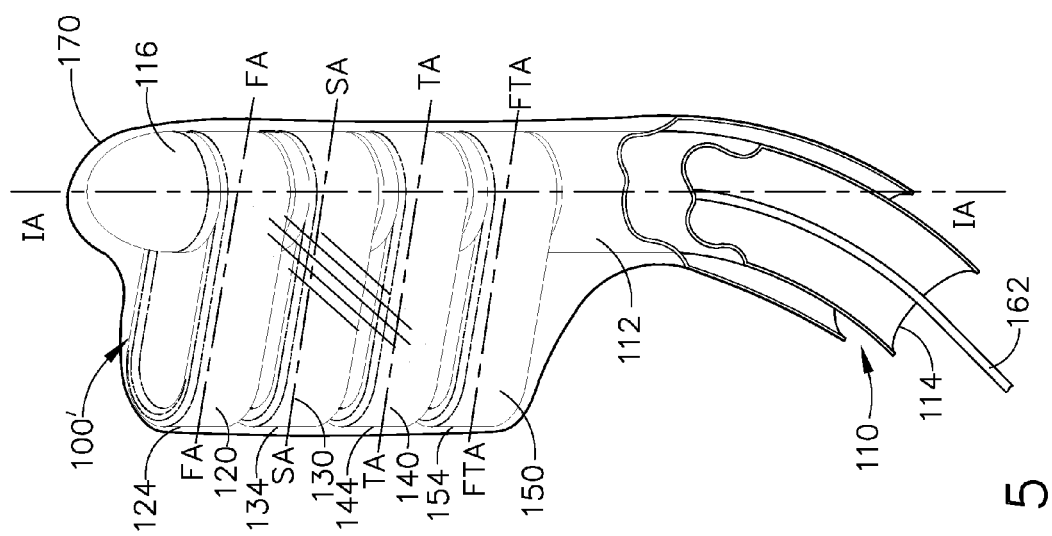
FIG. 6
FIG. 5

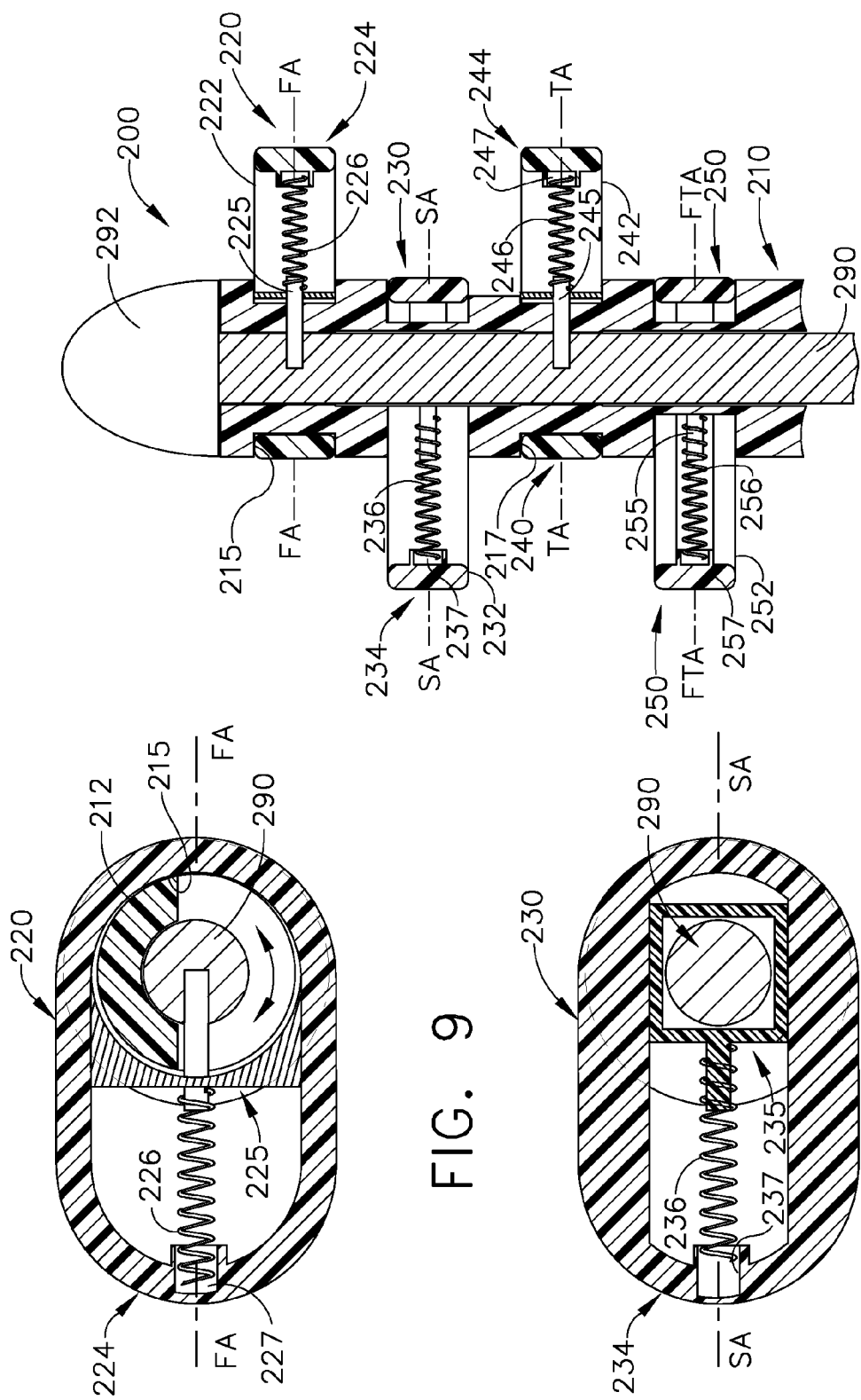

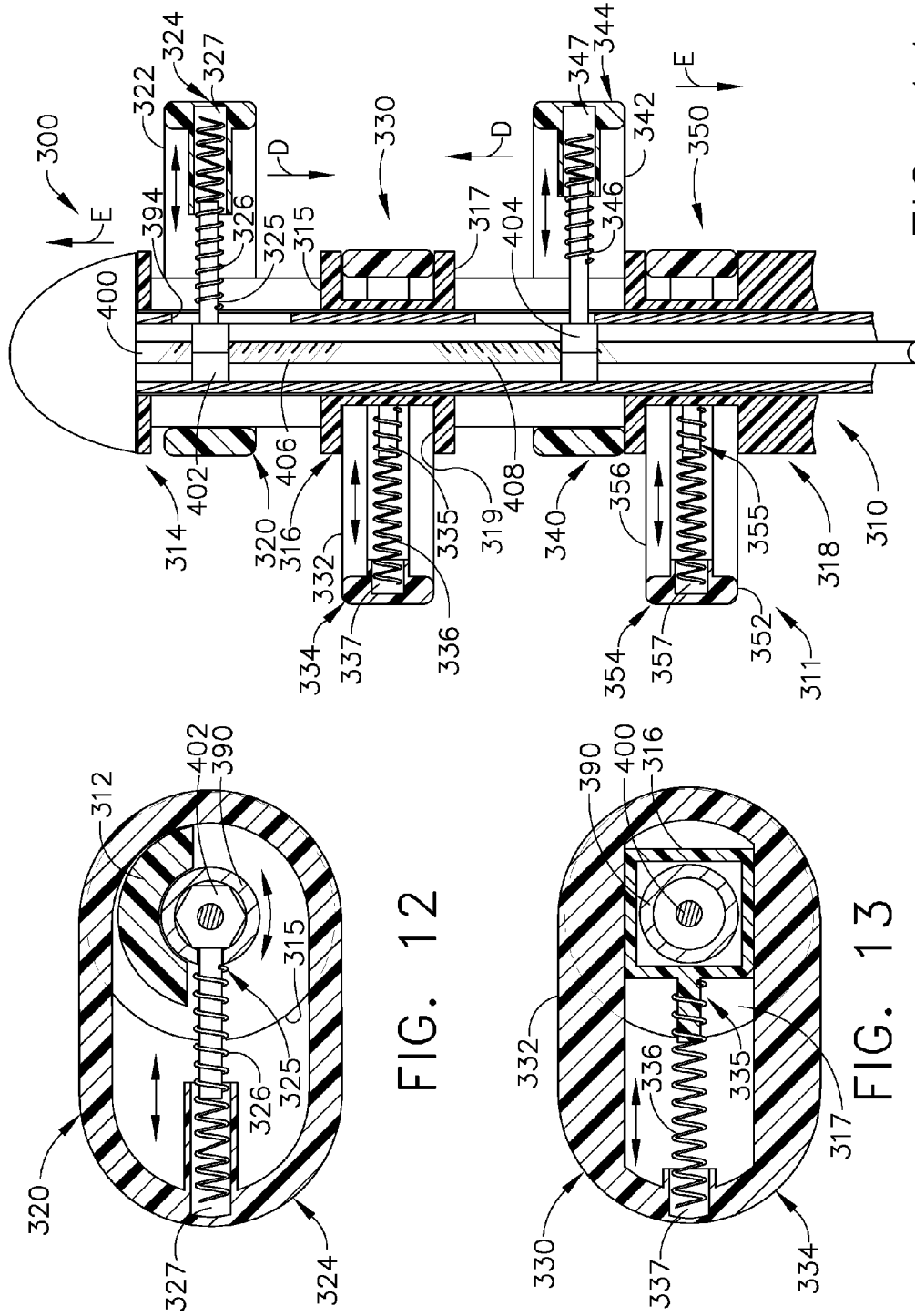

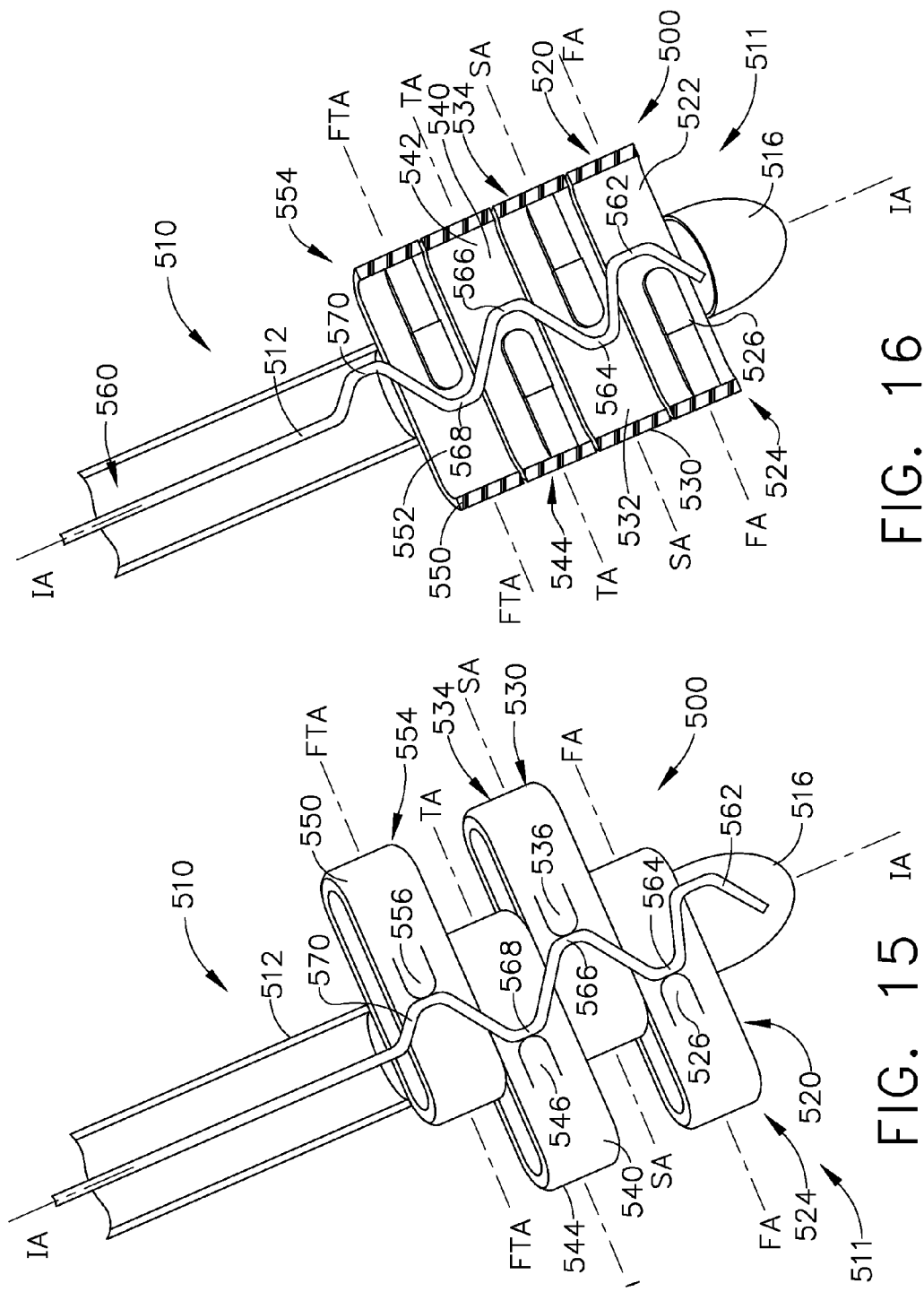

RECTAL MANIPULATION DEVICES

CROSS-REFERENCE TO RELATED APPLICATIONS

This non-provisional patent application claims the benefit of and priority from U.S. Provisional Patent Application Ser. No. 61/452,432, filed Mar. 14, 2011, entitled "Surgical Stapling Instruments", the entire disclosure of which is hereby incorporated by reference.

FIELD OF THE INVENTION

The present invention generally relates to surgical devices for manipulating tissues, and more particularly, to surgical devices for manipulating portions of the colon to improve access to various portions thereof.

BACKGROUND

Single-access laparoscopic surgery was first introduced for colectomy and later adapted for anterior resection. During single access laparoscopic pelvic procedures, such as total mesorectal excision, it is often difficult to obtain an adequate operative field. Often times, such dissections are made deep in the pelvis which makes it difficult to obtain adequate visualization of the area. During such procedures, the lower rectum must be lifted and rotated to gain access to the veins and arteries around both sides of the rectum during mobilization. During such manipulation, it is desirable to prevent the tissue from bunching up while being careful to avoid overstretching the tissue.

Thus, the need exists for a surgical tool that can be used to safely manipulate the colon to provide the surgeon with better visualization and access to the arteries and veins during mobilization.

The foregoing discussion is intended only to illustrate some of the shortcomings present in the field of the invention at the time, and should not be taken as a disavowal of claim scope.

BRIEF SUMMARY

In connection with general aspects of various embodiments of the present invention, there is provided a tissue manipulation device that, in at least one form, includes a shaft assembly that defines an insertion axis. A plurality of tissue manipulation arms that each have a tissue manipulation end are operably supported by the shaft assembly. At least some of the tissue manipulation arms are selectively movable from a first insertion position wherein all of the tissue manipulation ends are substantially aligned relative to each other and, upon application of an actuation motion thereto, the at least some of said tissue manipulation arms are moved to other deployed positions about the insertion axis wherein the ends of the tissue manipulation arms are not all aligned relative to each other.

In connection with yet another general aspect of one form of the present invention, there is provided a tissue manipulation device that comprises a shaft assembly that defines an insertion axis. A first tissue manipulation arm is movably supported on the shaft assembly and is movable relative thereto along a first axis that is substantially transverse to the insertion axis. A second tissue manipulation arm is movably supported on the shaft assembly and is movable relative thereto along a second axis that is substantially transverse to the insertion axis. A third manipulation arm is movably supported on the shaft assembly and is movable relative thereto along a third axis that is substantially transverse to the insertion axis. A fourth manipulation arm is movably supported on the shaft assembly and is movable relative thereto along a fourth axis that is substantially transverse to the insertion axis. An actuation member is configured to apply a deployment motion to at least two of the first, second, third, and fourth manipulation arms upon application of an actuation motion to the actuation member.

In accordance with still another general aspect of one form of the present invention, there is provided a tissue manipulation device that includes a shaft assembly that comprises an outer shaft portion that defines an insertion axis. A first actuator shaft is rotatably supported within the outer shaft portion and a second actuator shaft is rotatably supported within the first actuator shaft. In various forms, the tissue manipulation device further comprises a first tissue manipulation arm that is movably supported on the shaft assembly and operably interfaces with the first and second actuator shafts such that the first tissue manipulation arm is movable along a first axis that is substantially transverse to the insertion axis and is selectively rotatable about the insertion axis upon application of a first rotary actuation motion to the first actuator shaft. The first tissue manipulation arm is further selectively movable in directions that are substantially parallel to the insertion axis upon application of second rotary actuation motions to the second actuator shaft. A second tissue manipulation arm is movably supported on the shaft assembly and is constrained to move relative thereto along a second axis that is substantially transverse to the insertion axis. A third tissue manipulation arm is movably supported on the shaft assembly and operably interfaces with the first and second actuator shafts such that the third tissue manipulation arm is movable along a third axis that is substantially transverse to the insertion axis and is selectively rotatable about the insertion axis upon application of the first rotary actuation motion to the first actuator shaft. The third tissue manipulation arm is further movable in the directions that are substantially parallel to the insertion axis upon application of the second rotary actuation motions to the second actuator shaft. A fourth tissue manipulation arm is movably supported on the shaft assembly and is constrained to move relative thereto along a fourth axis that is substantially transverse to the insertion axis.

BRIEF DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 2 is a front elevational view of a portion of a tissue manipulation device embodiment of the present invention with the tissue manipulation arms thereof in an insertion or un-deployed position;

FIG. 3 is another front elevational view of the tissue manipulation device embodiment of FIG. 2 with some of the tissue manipulation arms thereof moved to deployed positions;

FIG. 5 is a partial perspective view of another tissue manipulation device embodiment of the present invention in an insertion position;

FIG. 6 is another perspective view of the tissue manipulation device embodiment of FIG. 5 with some of the tissue manipulation arms thereof in deployed positions;

FIG. 8 is a cross-sectional view of a tissue manipulation arm of the tissue manipulation device embodiment of FIG. 7 taken along line 8-8 in FIG. 7;

FIG. 9 is a cross-sectional view of another tissue manipulation arm of the tissue manipulation device embodiment of FIG. 7 taken along line 9-9 in FIG. 7;

FIG. 10 is another cross-sectional elevational view of a portion of the tissue manipulation device embodiment of FIG. 7 wherein some of the tissue manipulation arms thereof are in deployed positions;

FIG. 12 is a cross-sectional view of a tissue manipulation arm of the tissue manipulation device embodiment of FIG. 11 taken along line 12-12 in FIG. 11;

FIG. 13 is a cross-sectional view of another tissue manipulation arm of the tissue manipulation device embodiment of FIG. 11 taken along line 13-13 in FIG. 11;

FIG. 14 is another cross-sectional elevational view of a portion of the tissue manipulation device embodiment of FIG. 11 wherein some of the tissue manipulation arms thereof are in deployed positions;

FIG. 15 is a perspective view of a portion of another tissue manipulation device embodiment of the present invention with the tissue manipulation arms in deployed positions;

FIG. 16 is another perspective view of the portion of the tissue manipulation device of FIG. 15 with the tissue manipulation arms shown in cross-section in their respective insertion positions;

DETAILED DESCRIPTION

Figure 1:
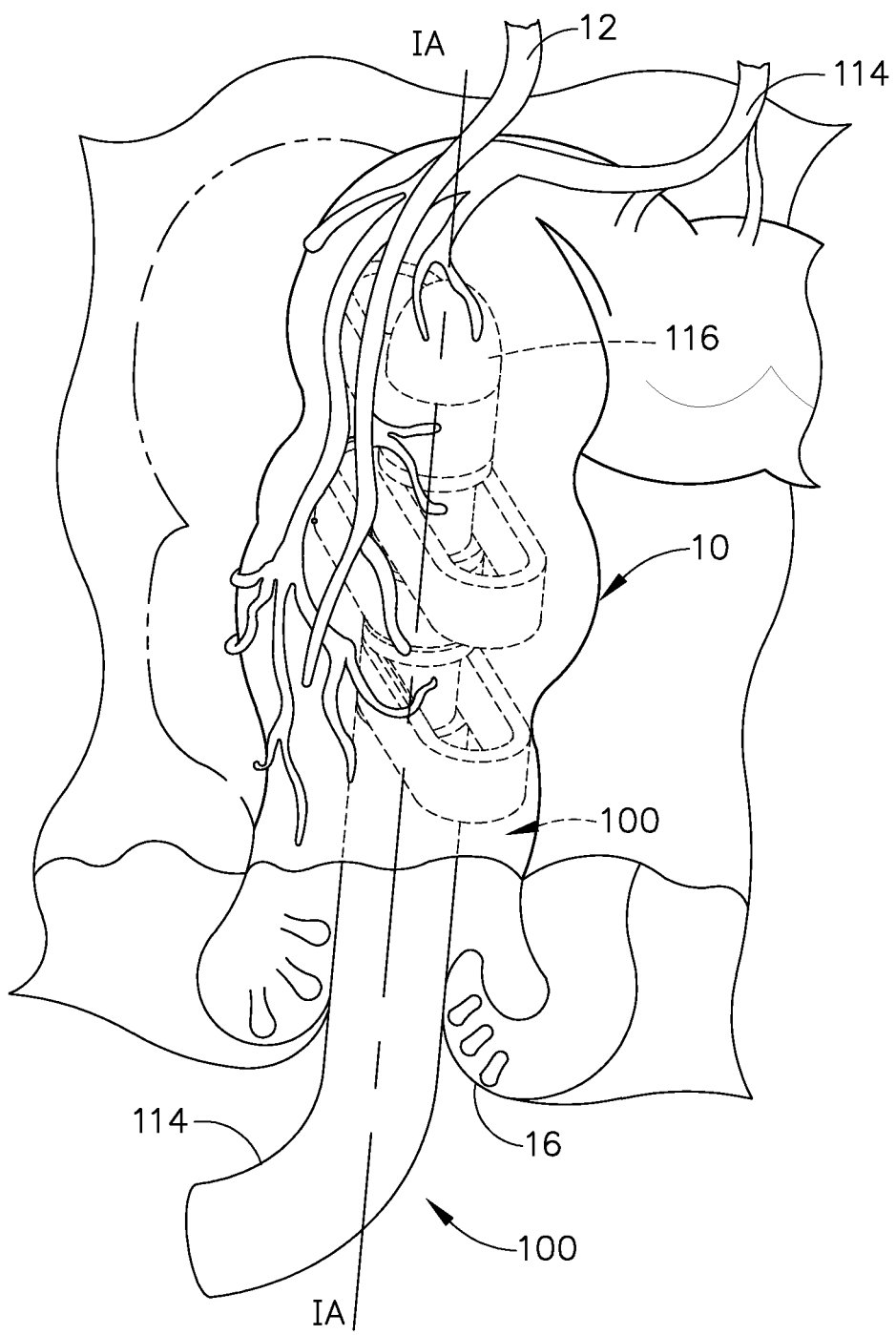
FIG. 1 is a perspective view of a portion of a colon with a tissue manipulation device embodiment of the present invention inserted therein.

The assignee of the present application also owns the following applications which were contemporaneously filed herewith and which are each herein incorporated by reference in their respective entireties:

U.S. patent application Ser. No. 13/181,779, now U.S. Patent Application Publication No. 2012/0234892 A1, filed Jul. 13, 2011, entitled "Multiple Part Anvil Assemblies For Circular Surgical Stapling Devices";

U.S. patent application Ser. No. 13/181,798, now U.S. Patent Application Publication No. 2012/0239010 A1, filed Jul. 13, 2011, entitled "Modular Surgical Tool Systems";

U.S. patent application Ser. No. 13/181,801, now U.S. Pat. No. 8,632,462, filed Jul. 13, 2011, entitled "Trans-Rectum Universal Ports";

U.S. patent application Ser. No. 13/181,807, now U.S. Patent Application Publication No. 2012/0238829 A1, filed Jul. 13, 2011, entitled "Modular Tool Heads For Use With Circular Surgical Instruments";

U.S. patent application Ser. No. 13/181,831, now U.S. Patent Application Publication No. 2012/0239082 A1, filed Jul. 13, 2011, entitled "Tissue Manipulation Devices";

U.S. patent application Ser. No. 13/181,768, now U.S. Patent Application Publication No. 2012/0234890 A1, filed Jul. 13, 2011, entitled "Collapsible Anvil Plate Assemblies For Circular Surgical Stapling Devices";

U.S. patent application Ser. No. 13/181,786, now U.S. Patent Application Publication No. 2012/0234898 A1, filed Jul. 13, 2011, entitled "Circular Stapling Devices With Tissue-Puncturing Anvil Features";

U.S. patent application Ser. No. 13/181,774, now U.S. Patent Application Publication No. US 2012/0234891 A1, filed Jul. 13, 2011, entitled "Anvil Assemblies With Collapsible Frames For Circular Staplers";

U.S. patent application Ser. No. 13/181,836, now U.S. Patent Application Publication No. US 2012/0238823 A1, filed Jul. 13, 2011, entitled "Surgical Access Devices With Anvil Introduction and Specimen Retrieval Structures"; and U.S. patent application Ser. No. 13/181,827, now U.S. Patent Application Publication No. US 2012/0238824 A1, filed Jul. 13, 2011, entitled "Surgical Bowel Retractor Devices".

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the various embodiments of the present invention is defined solely by the claims. The features illustrated or described in connection with one exemplary embodiment may be combined with the features of other embodiments. Such modifications and variations are intended to be included within the scope of the present invention.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment", or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation. Such modifications and variations are intended to be included within the scope of the present invention.

The terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

FIG. 1 is an anterior view of a colon 10 that illustrates the median sacral artery 12 and the superior rectal artery 14. As can also be seen in FIG. 1, a tissue manipulation device 100 according to at least one embodiment of the present invention has been inserted therein through the anus 16. In various embodiments, the tissue manipulation device 100 includes a central shaft assembly 110 that has a substantially straight distal end portion 112 that defines an insertion axis IA-IA. The central shaft assembly 110 may further have a proximal portion 114 that is curved to facilitate ease of control and insertion of the distal end portion 112 and head assembly 111 into the colon 10 through the anus 16. See FIG. 1. The distal end portion of the shaft 112 terminates in a blunt end cap or portion 116.

In at least one form, the tissue manipulation device 100 further comprises a plurality of tissue manipulation arms 120, 130, 140, 150 that are operably supported on the central shaft assembly 110. More specifically, a first tissue manipulation arm 120 comprises a first body portion 122 that has a relatively blunt first tissue manipulation end 124. The first tissue manipulation arm 120 is constrained to move laterally along a first axis FA-FA that is substantially transverse to the installation axis IA-IA between a first insertion position shown in FIG. 2 and at least one deployed position such as the deployed position depicted in FIG. 3. The position shown in FIG. 3 is a fully deployed position. Likewise, a second tissue manipulation arm 130 comprises a second body portion 132 that has a relatively blunt second tissue manipulation end 134. The second tissue manipulation arm 130 is constrained to move laterally along a second axis SA-SA that is substantially transverse to the installation axis IA-IA between a first insertion position shown in FIG. 2 and at least one deployed position such as the deployed position depicted in FIG. 3. A third tissue manipulation arm 140 comprises a third body portion 142 that has a relatively blunt third tissue manipulation end 144. The third tissue manipulation arm 140 is constrained to move laterally along a third axis TA-TA that is substantially transverse to the installation axis IA-IA between a first insertion position shown in FIG. 2 and at least one deployed position such as the deployed position depicted in FIG. 3. A fourth tissue manipulation arm 150 comprises a fourth body portion 152 that has a relatively blunt fourth tissue manipulation end 154. The fourth tissue manipulation arm 150 is constrained to move laterally along a fourth axis FTA-FTA that is substantially transverse to the installation axis IA-IA between a first insertion position shown in FIG. 2 and at least one deployed position such as the deployed position depicted in FIG. 3.

Figure 4:
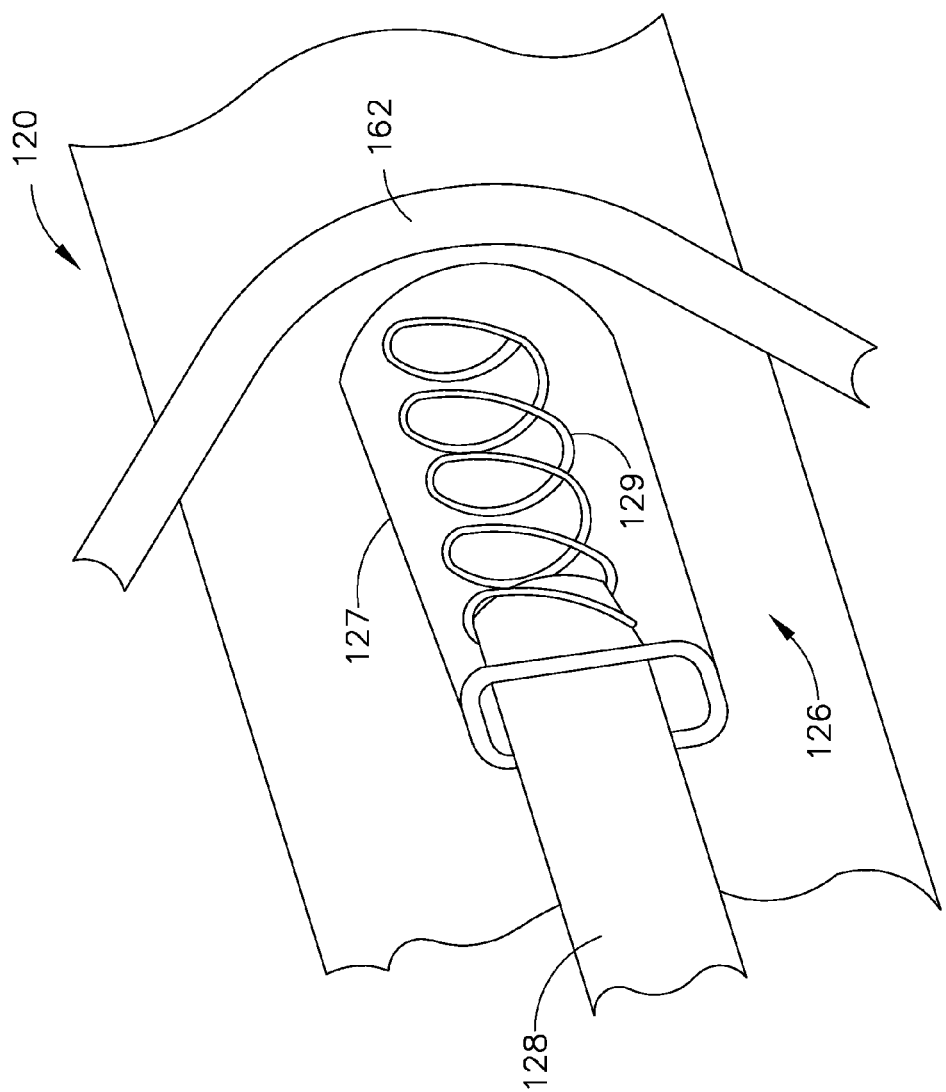
FIG. 4 is a perspective view of a portion of a detent arrangement employed in the tissue manipulation device embodiment of FIGS. 2 and 3.

Various embodiments of the tissue manipulation device 100 further include an actuator 160 for selectively applying deployment motions to the tissue manipulation arms 120, 130, 140, 150. As can be seen in FIGS. 2 and 3, in at least one form, the actuator comprises a tension cable 162 that extends from the blunt end portion 116 through the shaft assembly 110. The tension cable 162 is weaved around spring biased detents located on the inside of the tissue manipulation arms 120, 130, 140, 150. More specifically, as can be seen in FIGS. 2 and 3, the first tissue manipulation arm 120 has a first spring loaded detent 126 therein that comprises a piston head 127 that is movably journaled on a pin 128 as shown in FIG. 4. A spring 129 is provided to apply a biasing force to the piston head 127. The second tissue manipulation arm 130 has a second spring loaded detent 136 therein that is substantially the same as the first spring loaded detent 126. The third tissue manipulation arm 140 has a third spring loaded detent 146 therein that is substantially the same as the first spring loaded detent 126. The fourth tissue manipulation arm 150 has a second spring loaded detent 156 therein that is substantially the same as the first spring loaded detent 126. Also in at least one embodiment, a rigid detent 113 is formed in or attached to the shaft 112 as shown in FIGS. 2 and 3.

In at least one embodiment, the head portion 111 is received with an expandable sheath 170. The expandable sheath 170 is fabricated from an elastic material and may serve to retain the head assembly 111 in an unexpanded configuration as shown in FIG. 2. The tension cable 162 extends out through the proximal portion 114 of the shaft assembly to enable the surgeon to apply tension "T" thereto. When in the unexpanded configuration (insertion position), all of the ends 124, 134, 144, 154 of the tissue manipulation arms 120, 130, 140, 150, respectively are substantially aligned relative to the insertion axis IA-IA. See FIG. 2. When the tissue manipulation arms 120, 130, 140, 150 are laterally deployed, the tissue manipulation ends 124, 144 are not aligned with the ends 134 and 154. See FIG. 3.

The tissue manipulation device 100 may be used by inserting the head assembly 111 with the sheath 170 thereover into the colon 10 through the anus 16 as shown in FIG. 1. When in that position, the proximal end portion 114 of the shaft assembly 110 protrudes out of the anus 16 providing the surgeon with the ability to further manipulate the device as needed and to also apply tension to the cable 162. Once the head assembly 111 has been inserted to the desired position in the unexpanded orientation (FIG. 2), the surgeon applies and actuation force "T" to the cable 162 by pulling on it which ultimately causes the tissue manipulation arms 120, 130, 140, 150 to move laterally to their deployed positions. As the tissue manipulation arms 120, 130, 140, 150 are laterally deployed, the sheath 170 stretches. The tissue manipulation arms 120, 130, 140, 150 contact corresponding portions of the colon and move them outward thereby expanding the colon 10. It will be understood that the extent to which the tissue manipulation arms 120, 130, 140, 150 are deployed depends somewhat upon the amount of tension "T" applied to the cable 162.

FIGS. 5 and 6 illustrate an alternative tissue manipulation device embodiment 100' that operates in substantially the same manner as the tissue manipulation device described above. However, in this embodiment, when the tissue manipulation arms 120, 130, 140, 150 are in the initial insertion position or orientation, all of the all of the ends 124, 134, 144, 154 of the tissue manipulation arms 120, 130, 140, 150, respectively are substantially aligned along one side of the insertion axis IA-IA. Then, when an actuation motion "T" is applied to the cable 162, only the second tissue manipulation arm 130 and the fourth tissue manipulation arm 150 move laterally along their respective axes SA-SA and FTA-FTA. Thus, in this embodiment, the first tissue manipulation arm 120 and the third tissue manipulation arm 130 do not move laterally upon application of a tension force "T" to the cable 162. However, each of the tissue manipulation arms 120, 130, 140, 150 may be spring biased to enable the arms to move laterally during insertion.

FIGS. 7-10 illustrate another tissue manipulation device embodiment 200. In various embodiments, the tissue manipulation device 200 includes a central shaft assembly 210 that has an outer shaft 212 that has a substantially straight distal end portion 213 that defines an insertion axis IA-IA. The central shaft assembly 210 may further have a proximal portion (not shown) that is curved to facilitate ease of control and insertion of the distal end portion 212 and the head assembly generally designated as 211 into the colon 10 through the anus 16 in the manner described above.

In at least one form, the tissue manipulation device 200 further comprises a plurality of tissue manipulation arms 220, 230, 240, 250 that are operably supported on the central shaft assembly 210. More specifically, a first tissue manipulation arm 220 comprises a first body portion 222 that has a relatively blunt first tissue manipulation end 224. The body portion 222 of the first tissue manipulation arm 220 is received within a first slot 215 in the outer shaft portion 212 such that it can be selectively rotated about the installation axis IA-IA. In addition, the first tissue manipulation arm 220 is constrained to move laterally along a first axis FA-FA that is substantially transverse to the installation axis IA-IA in response to forces applied thereto by the colon.

More specifically, the central shaft assembly 210 further includes an actuation shaft 290 that extends through the outer shaft 212 and is rotatably supported therein for selective rotation about the insertion axis IA-IA. The actuation shaft 290 terminates in a blunt end member 292. In at least one embodiment, the first tissue manipulation arm 220 is slidably journaled on a first pin assembly 225 that is attached to the actuation rod 290. A first biasing spring 226 extends over the first pin assembly 225 and is received in a first socket 227 in the first tissue manipulation end 224. Thus, as a rotary actuation force is applied to the actuation shaft 290, the first tissue manipulation arm 220 is rotated about the insertion axis IA-IA.

The second tissue manipulation arm 230 comprises a second body portion 232 that has a relatively blunt second tissue manipulation end 234. The body portion 232 of the second tissue manipulation arm 230 is received within a second slot 216 in the outer shaft portion 212 to enable the second tissue manipulation arm 230 to move laterally relative thereto along a second axis SA-SA that is substantially transverse to the installation axis IA-IA in response to forces applied thereto by the colon. Also, the second tissue manipulation arm 230 is slidably journaled on a second pin 235 that is attached to the outer shaft 212. A second biasing spring 236 extends over the second pin 235 and is received in a second socket 237 in the second tissue manipulation end 234. Thus, the second tissue manipulation arm 220 does not rotate when the actuation shaft 290 is rotated.

The third tissue manipulation arm 240 comprises a third body portion 242 that has a relatively blunt third tissue manipulation end 244. The body portion 242 of the third tissue manipulation arm 240 is received within a third slot 217 in the outer shaft portion 212 such that it can be selectively rotated about the installation axis IA-IA. In addition, the third tissue manipulation arm 240 is constrained to move laterally along a third axis TA-TA that is substantially transverse to the installation axis IA-IA in response to forces applied thereto by the colon. In at least one embodiment, the third tissue manipulation arm 240 is slidably journaled on a third pin assembly 245 that is attached to the actuation rod 290. A third biasing spring 246 extends over the third pin assembly 245 and is received in a third socket 247 in the third tissue manipulation end 24. Thus, as a rotary actuation force is applied to the actuation shaft 290, the third tissue manipulation arm 240 is rotated about the insertion axis IA-IA.

The fourth tissue manipulation arm 250 comprises a fourth body portion 252 that has a relatively blunt fourth tissue manipulation end 254. The body portion 252 of the fourth tissue manipulation arm 250 is received within a fourth slot 218 in the outer shaft portion 212 to enable the fourth tissue manipulation arm 250 to move laterally relative thereto along a fourth axis FTA-FTA that is substantially transverse to the installation axis IA-IA in response to forces applied thereto by the colon. Also, the fourth tissue manipulation arm 250 is slidably journaled on a fourth pin 255 that is attached to the outer shaft 212. A fourth biasing spring 256 extends over the fourth pin 255 and is received in a fourth socket 257 in the fourth tissue manipulation end 254. Thus, the fourth tissue manipulation arm 250 does not rotate when the actuation shaft 290 is rotated.

Figure 7:
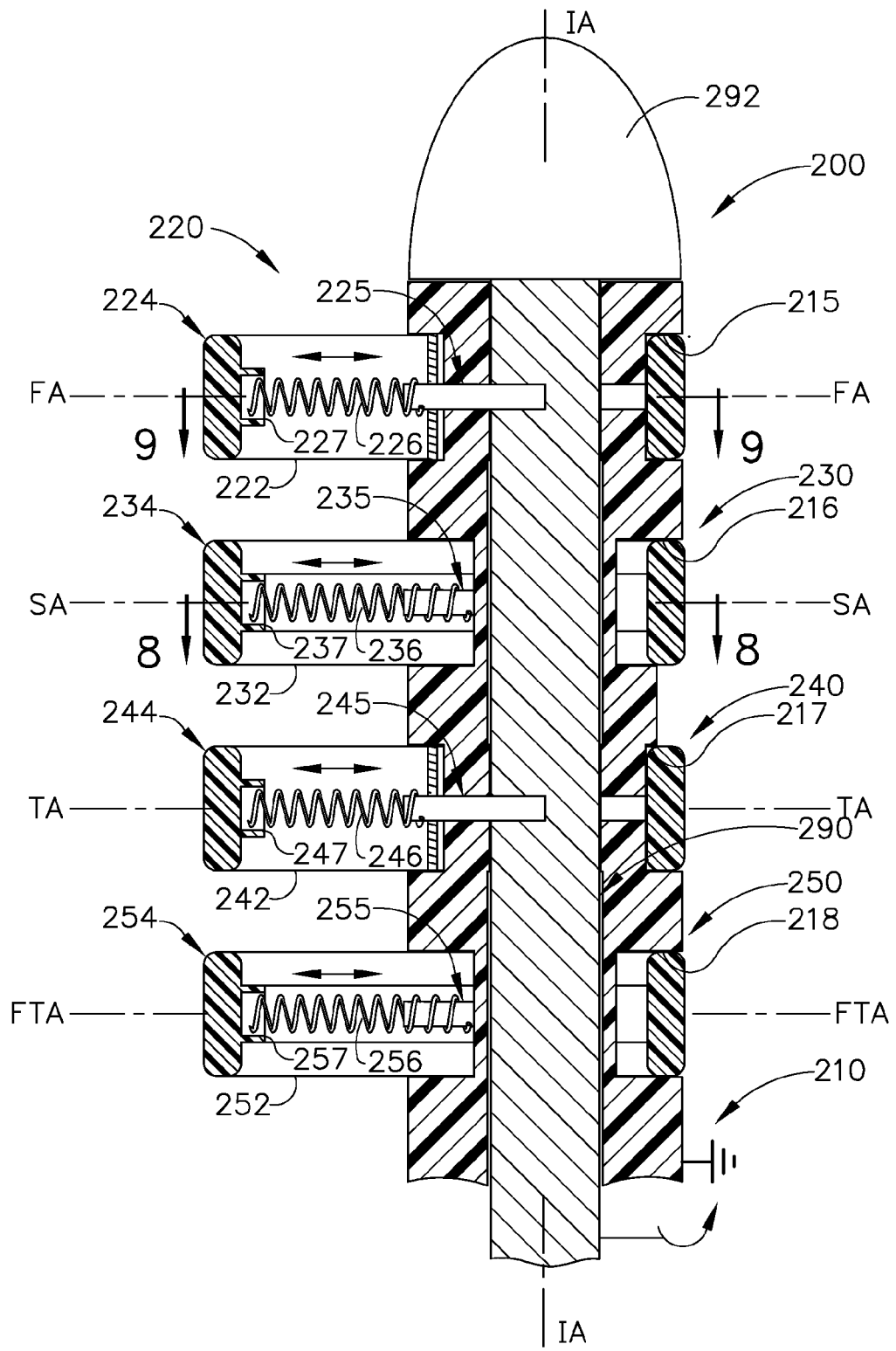
FIG. 7 is a cross-sectional elevational view of a portion of another tissue manipulation device embodiment of the present invention in an insertion position.

To use the tissue manipulation device 200, the surgeon first orients the second and fourth tissue manipulation arms 230, 250 in the insertion position shown in FIG. 7 wherein all of the tissue manipulation ends 224, 234, 244, 254 are all substantially aligned on one side of the insertion axis IA-IA. As with the other embodiments, an expandable sheath may be inserted over the head portion 211 in the manner discussed above. Once the tissue manipulation device 200 has been inserted to the desired position in the colon, the surgeon then applies a rotary actuation motion to the actuation shaft 290 to rotate the first and third tissue manipulation arms 220, 240 about the insertion axis IA-IA to their deployed positions as shown in FIG. 10.

FIGS. 11-14 illustrate another tissue manipulation device embodiment 300. In various embodiments, the tissue manipulation device 300 includes a central shaft assembly 310 that has an outer shaft assembly 312 that defines an insertion axis IA-IA. The outer shaft assembly 312 includes a distal portion 314 that is separated from a central portion 216 by a slot or gap 315, and a proximal portion 318 that is separated from the central portion 316 by a slot or gap 317. The proximal portion 318 may be curved near to its proximal end to facilitate ease of control and insertion of the head assembly generally designated as 311 into the colon 10 through the anus 16 in the manner described above.

In at least one form, the tissue manipulation device 300 further comprises a plurality of tissue manipulation arms 320, 330, 340, 350 that are operably supported on the central shaft assembly 310. More specifically, a first tissue manipulation arm 320 comprises a first body portion 322 that has a relatively blunt first tissue manipulation end 324. The body portion 322 of the first tissue manipulation arm 320 is received within a the slot or gap 315 in the outer shaft portion 312 such that it can be selectively rotated about the installation axis IA-IA and also move axially along the installation shaft IA-IA. In addition, the first tissue manipulation arm 320 is constrained to move laterally along a first axis FA-FA that is substantially transverse to the installation axis IA-IA in response to forces applied thereto by the colon.

In various embodiments, the shaft assembly 310 further includes a first actuation shaft 390 that extends through the outer shaft portions 318, 316 and terminates at outer shaft portion 314. The first actuation shaft 390 is substantially hollow and is rotatably supported within the outer shaft 312 for selective rotation about the insertion axis IA-IA. The first actuation shaft 390 terminates in a blunt end member 392. In at least one embodiment, the first tissue manipulation arm 320 is slidably journaled on a first pin assembly 325 that is attached to a nut member 402 that is threadably coupled to a second actuation shaft 400 that is rotatably received within the hollow first actuation shaft 390. The first pin assembly 325 extends through a first slot 394 in the first actuation shaft 390. A first biasing spring 326 is received on the first pin assembly 325 and is received in a first socket 327 in the first tissue manipulation end 324.

The second tissue manipulation arm 330 comprises a second body portion 332 that has a relatively blunt second tissue manipulation end 334. The body portion 332 of the second tissue manipulation arm 330 is received within a slot 319 in the second outer shaft portion 316 to enable the second tissue manipulation arm 330 to move laterally relative thereto along a second axis SA-SA that is substantially transverse to the installation axis IA-IA in response to forces applied thereto by the colon. Also, the second tissue manipulation arm 330 is slidably journaled on a second pin assembly 335 that is attached to the outer shaft portion 316. A second biasing spring 336 is received on the second pin assembly 335 and is received in a second socket 337 in the second tissue manipulation end 334.

The third tissue manipulation arm 340 comprises a third body portion 342 that has a relatively blunt third tissue manipulation end 344. The body portion 342 of the third tissue manipulation arm 340 is received within a third slot 317 in the outer shaft portion 312 such that it can be selectively rotated about the installation axis IA-IA. In at least one embodiment, the third tissue manipulation arm 340 is slidably journaled on a third pin assembly 345 that is attached to a nut member 404 that is threadably coupled to the second actuation shaft 400 that is rotatably received within the hollow first actuation shaft 390. The third pin assembly 345 extends through a third slot 396 in the first actuation shaft 390. A third biasing spring 346 is received on the third pin assembly 345 and is received in a third socket 347 in the third tissue manipulation end 344.

The fourth tissue manipulation arm 350 comprises a fourth body portion 352 that has a relatively blunt fourth tissue manipulation end 354. The body portion 352 of the fourth tissue manipulation arm 350 is received within a fourth slot 318 in the outer shaft portion 312 to enable the fourth tissue manipulation arm 350 to move laterally relative thereto along a fourth axis FTA-FTA that is substantially transverse to the installation axis IA-IA in response to forces applied thereto by the colon. Also, the fourth tissue manipulation arm 350 is slidably journaled on a fourth pin assembly 355 that is attached to the outer shaft 312. A fourth biasing spring 356 is received on the fourth pin 355 and is received in a fourth socket 357 in the fourth tissue manipulation end 354. Thus, the fourth tissue manipulation arm 350 does not rotate when the first actuation shaft 390 is rotated.

Figure 11:
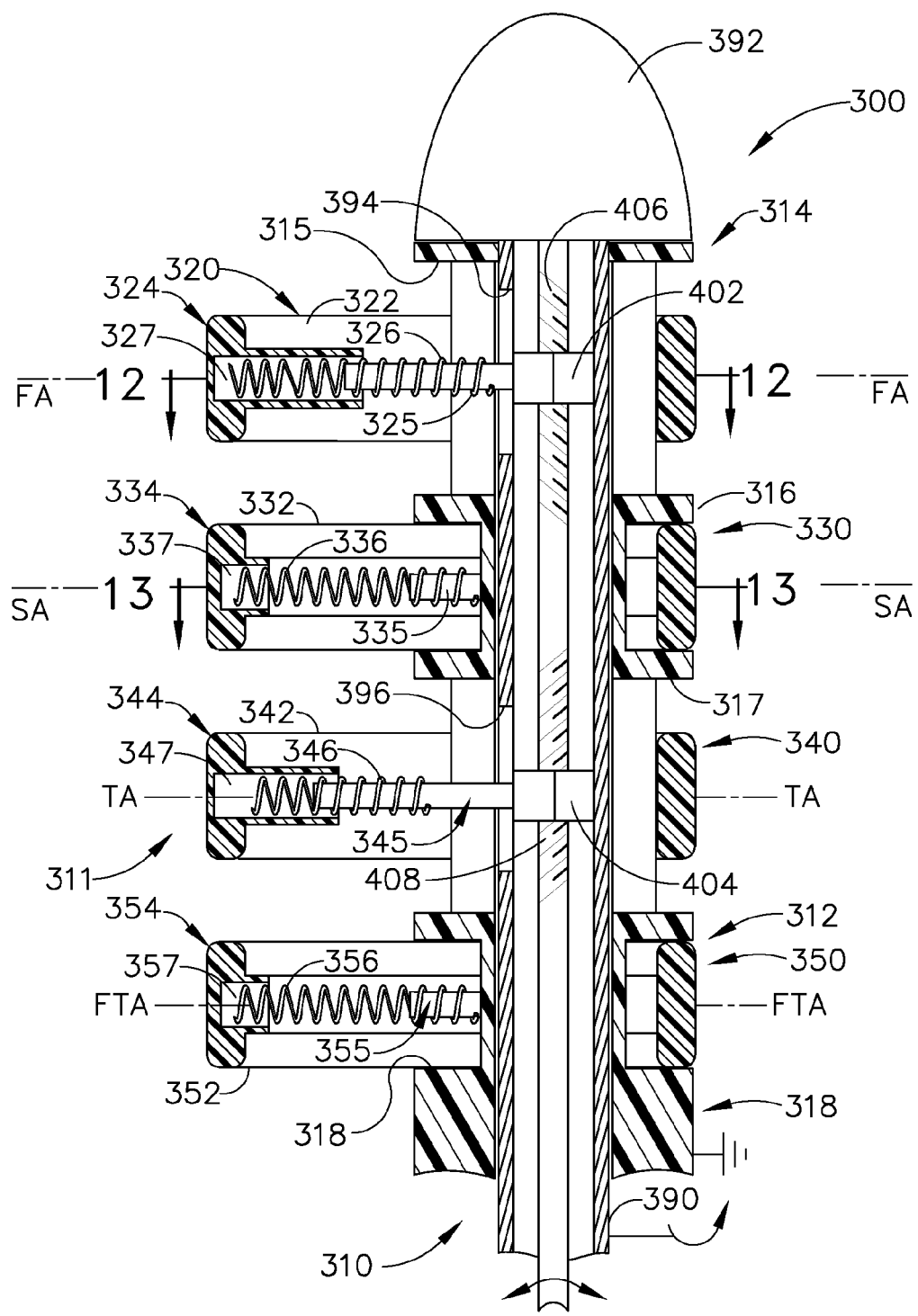
FIG. 11 is a cross-sectional elevational view of a portion of another tissue manipulation device embodiment of the present invention in an insertion position.

As can be seen in FIGS. 11 and 14, the second actuation shaft 400 has two thread segments 406 and 408 thereon. The first nut 402 is in threaded engagement with the first thread segment 406 and the second nut 404 is in threaded engagement with the second thread segment 408. The first and second thread segments 406, 408 are threaded in different directions on the second actuation shaft 400 such that rotation of the second actuation shaft 400 in one direction causes the first tissue manipulation arm 320 and the third tissue manipulation arm 340 to move axially toward each other (arrows "D" in FIG. 14) and rotation of the second actuation shaft 400 in an opposite rotary direction causes the first tissue manipulation arm 320 and the third tissue manipulation arm 340 to move axially away from each other (arrows "E" in FIG. 14).

To use the tissue manipulation device 300, the surgeon first orients the first and third tissue manipulation arms 320, 340 in the insertion position shown in FIG. 11 wherein all of the tissue manipulation ends 324, 334, 344, 354 are all substantially aligned on one side of the insertion axis IA-IA. As with the other embodiments, an expandable sheath may be inserted over the head portion 311 in the manner discussed above. Once the tissue manipulation device 300 has been inserted to the desired position in the colon, the surgeon then applies a first rotary actuation motion to the first actuation shaft 390 to rotate the first and third tissue manipulation arms 320, 340 about the insertion axis IA-IA to their rotary deployed positions as shown in FIG. 14. Thereafter, if the surgeon determines that the first and third tissue manipulation arms 320, 340 need to be moved axially to better manipulate the corresponding portions of the colon, the surgeon may then apply a rotary control motion to the second actuation shaft 400. As indicated above, rotating the second actuation shaft 400 in one direction will cause the first and third tissue manipulation arms 320, 340 to move axially toward each other and rotation of the second actuation shaft in an opposite direction will cause the first and third tissue manipulation arms 320, 340 to move axially away from each other.

Figure 17:
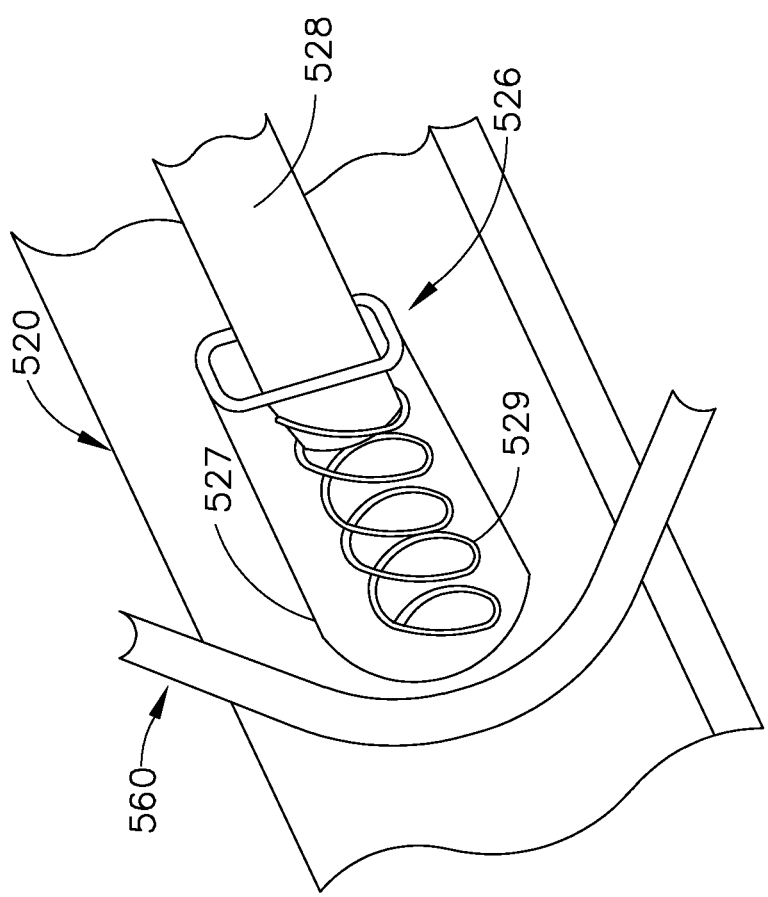
FIG. 17 is a partial perspective view of a detent assembly embodiment employed in the tissue manipulation device of FIGS. 15 and 16.

FIGS. 15-17 disclose another tissue manipulation device 500 includes a central shaft assembly 510 that has a substantially straight distal end portion 512 that defines an insertion axis IA-IA. The central shaft assembly 510 may further have a proximal portion (not shown) that is curved to facilitate ease of control and insertion of the distal end portion 512 and the head assembly 511 thereof into the colon 10 through the anus 16. The distal end portion of the shaft 512 terminates in a substantially hollow blunt end cap 516. In at least one form, the tissue manipulation device 500 further comprises a plurality of tissue manipulation arms 520, 530, 540, 550 that are operably supported on the central shaft assembly 510. More specifically, a first tissue manipulation arm 520 comprises a first body portion 522 that has a relatively blunt first tissue manipulation end 524. The first tissue manipulation arm 520 is constrained to move laterally along a first axis FA-FA that is substantially transverse to the installation axis IA-IA between a first insertion position shown in FIG. 16 and at least one deployed position such as the deployed position depicted in FIG. 15. The position shown in FIG. 15 is a fully deployed position.

Likewise, a second tissue manipulation arm 530 comprises a second body portion 532 that has a relatively blunt second tissue manipulation end 534. The second tissue manipulation arm 530 is constrained to move laterally along a second axis SA-SA that is substantially transverse to the installation axis IA-IA between a first insertion position shown in FIG. 16 and at least one deployed position such as the deployed position depicted in FIG. 15. A third tissue manipulation arm 540 comprises a third body portion 542 that has a relatively blunt third tissue manipulation end 544. The third tissue manipulation arm 540 is constrained to move laterally along a third axis TA-TA that is substantially transverse to the installation axis IA-IA between a first insertion position shown in FIG. 2 and at least one deployed position such as the deployed position depicted in FIG. 15. A fourth tissue manipulation arm 550 comprises a fourth body portion 552 that has a relatively blunt fourth tissue manipulation end 554. The fourth tissue manipulation arm 550 is constrained to move laterally along a fourth axis FTA-FTA that is substantially transverse to the installation axis IA-IA between a first insertion position shown in FIG. 16 and at least one deployed position such as the deployed position depicted in FIG. 15.

Various embodiments of the tissue manipulation device 500 further include an actuator rod 560 for selectively applying deployment motions to the tissue manipulation arms 520, 530, 540, 550. As can be seen in FIGS. 15 and 16, in at least one form, the actuator rod 560 has a plurality of bends 562, 564, 566, 568, 570 therein. The actuator rod 560 is configured for selective axial travel within the shaft assembly 510 and the tissue manipulation arms 520, 530, 540, 550. The bends 562, 564, 566, 568, 570 in actuator rod 560 are configured to selectively engage spring biased detents located on the inside of or otherwise attached to the tissue manipulation arms 520, 530, 540, 550. More specifically, as can be seen in FIG. 16, the first tissue manipulation arm 520 has a first spring loaded detent 526 therein that comprises a piston head 527 that is movably journaled on a pin 528 as shown in FIG. 17. A spring 529 is provided to apply a biasing force to the piston head 527. The second tissue manipulation arm 530 has a second spring loaded detent 536 therein that is substantially the same as the first spring loaded detent 526. The third tissue manipulation arm 540 has a third spring loaded detent 546 therein that is substantially the same as the first spring loaded detent 526. The fourth tissue manipulation arm 550 has a fourth spring loaded detent 556 therein that is substantially the same as the first spring loaded detent 526. In at least one embodiment, the head portion 511 is received with an expandable sheath assembly as was described above.

The tissue manipulation device 500 may be used by inserting the head assembly 511 with the sheath thereover into the colon through the anus. When in that position, the proximal end portion of the shaft assembly 510 protrudes out of the anus providing the surgeon with the ability to further manipulate the device 500 as needed and to also apply actuation motions to the actuator rod 560. Once the head assembly 511 has been inserted to the desired position in the unexpanded orientation (FIG. 16), the surgeon applies and actuation force to the actuation rod 560 to force it within the shaft assembly 510 in the distal direction "DD". As the actuator rod 560 is moved distally, the bend 564 contacts detent 526 and pushes the first tissue manipulation arm 520 laterally along the first axis FA-FA. Likewise, the bend 566 contacts the second detent 536 and pushes the second tissue manipulation arm 530 laterally along the second axis SA-SA. The bend 568 contacts the third detent 546 and biases the third tissue manipulation arm 540 laterally along the third axis TA-TA. The bend 570 contacts the fourth detent 556 and biases the fourth tissue manipulation arm 550 laterally along the fourth axis FTA-FTA. The distal most bend 562 extends into the hollow cap 516 as shown in FIG. 15. When the surgeon applies a pulling motion to the actuator rod 560 in the proximal direction, the bends 562, 564, 566, 568, 570 are moved to the positions shown in FIG. 16 and the detents 526, 536, 546, 556 return the tissue manipulation arms 520, 530, 540, 550, respectively to their insertion or un-deployed positions as shown in FIG. 16.

The various tissue manipulation device embodiments disclosed herein may have a dedicated handle portion that is attached to the proximal end portion of the shaft assembly. The handle arrangements may include actuator knobs and other arrangements for applying actuation motions to the actuation cable or to the actuation shaft(s), whichever the case may be. In still other embodiments, at least some of the tissue manipulation devices disclosed herein may be configured to receive their actuation motions from robotic systems. Other embodiments may be configured to interface with one or more of the modular circular surgical instruments disclosed in one or more of the above-identified patent applications that have been herein incorporated by reference and which are presently commonly owned by the assignee of the subject application. For example, the outer shaft portion of various tissue manipulation devices may be configured to be attached to the distal end of the circular surgical instrument's outer shaft by a "bayonet-type" or other removable coupling arrangement. The actuation shaft(s) of the tissue manipulation device(s) may also be configured to interface with the various actuation shaft arrangements in those modular circular surgical instruments to enable the surgeon to apply the desired rotational actuation motion(s) thereto by actuating the appropriate actuator portion(s) of the circular surgical instrument. Such arrangements are intended to be within the scope of various embodiments of the present invention.

Figure 18:
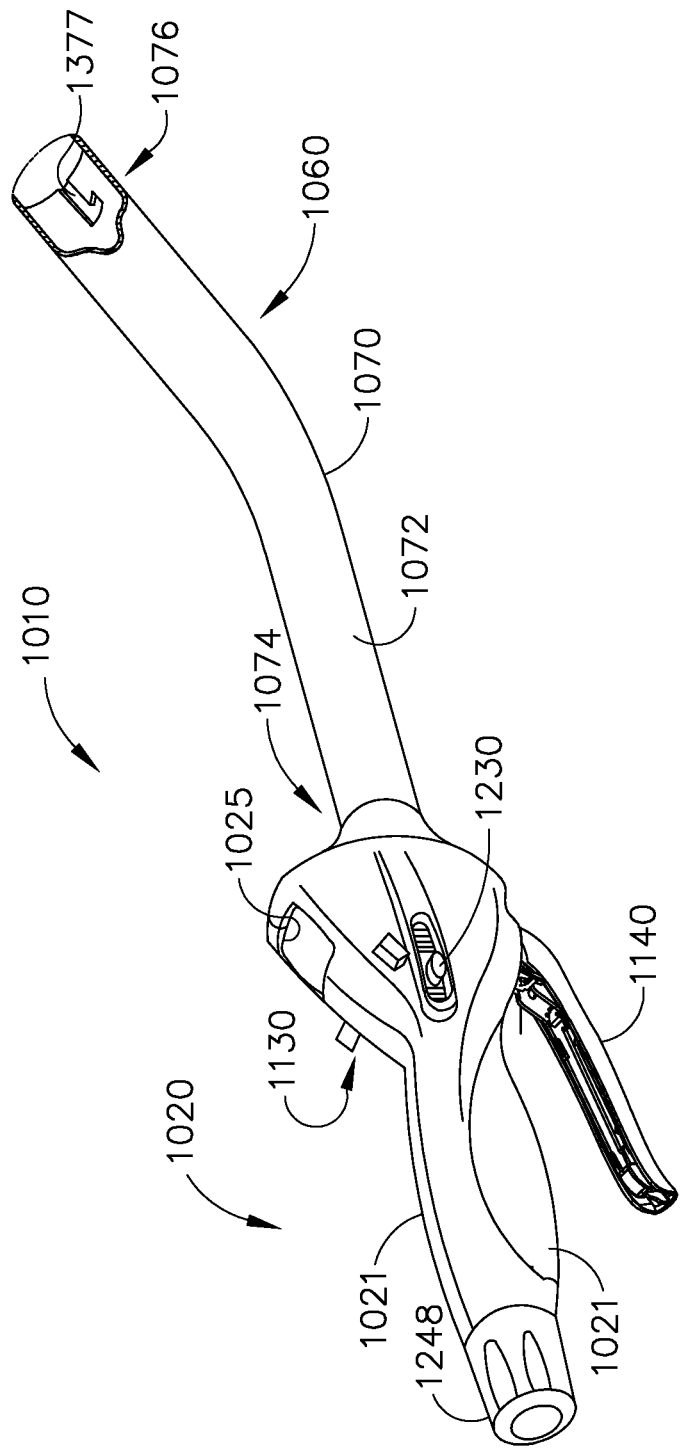
FIG. 18 is an exploded perspective view of one form of a modular surgical instrument.

FIG. 18 illustrates one form of a modular surgical instrument 1010 of an embodiment of the present invention. In at least one embodiment, the modular surgical instrument 1010 includes a universal actuator handle assembly 1020 that is attached to an elongated shaft assembly 1060 that is configured for operable attachment to a variety of different surgical tool heads. In the depicted embodiment, the handle assembly 1020 operably supports an actuation system generally designated as 1100 which is configured to selectively apply various forms of actuation forces to the particular-type of surgical tool head attached thereto. In various embodiments, the handle assembly 1020 includes two handle case segments 1021 that may be interconnected together by suitable fastener arrangements for ease of assembly. The shaft assembly 1060 includes an outer shaft casing 1070 that is substantially hollow and may be fabricated from two casing segments 1072 that are coupled together to form a hollow conduit. The outer shaft casing 1070 has a proximal end 1074 that is coupled to the handle assembly 1020 and an open distal end 1076.

Figure 19:
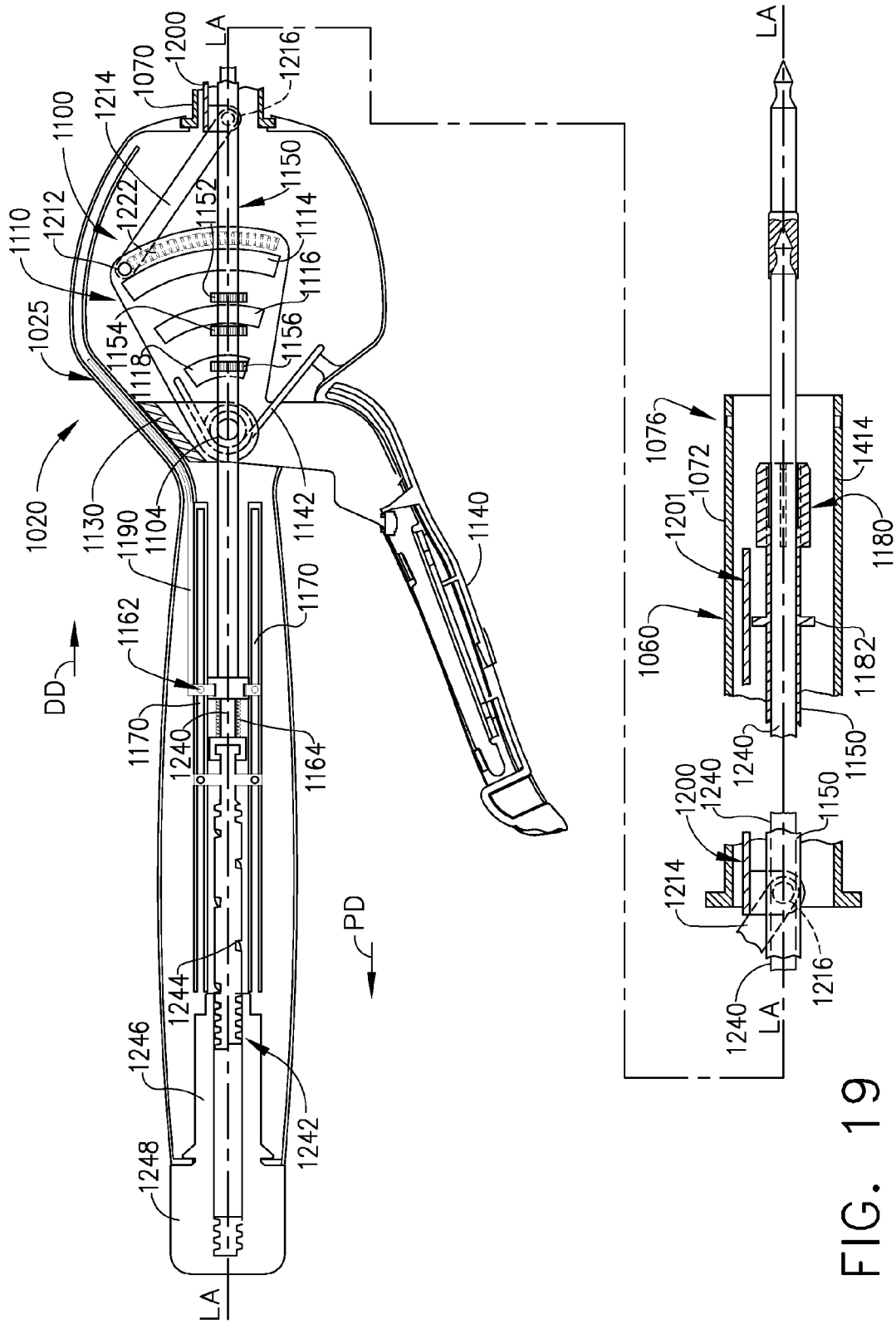
FIG. 19 is a cross-sectional view of one form of a modular surgical instrument.
Figure 20:
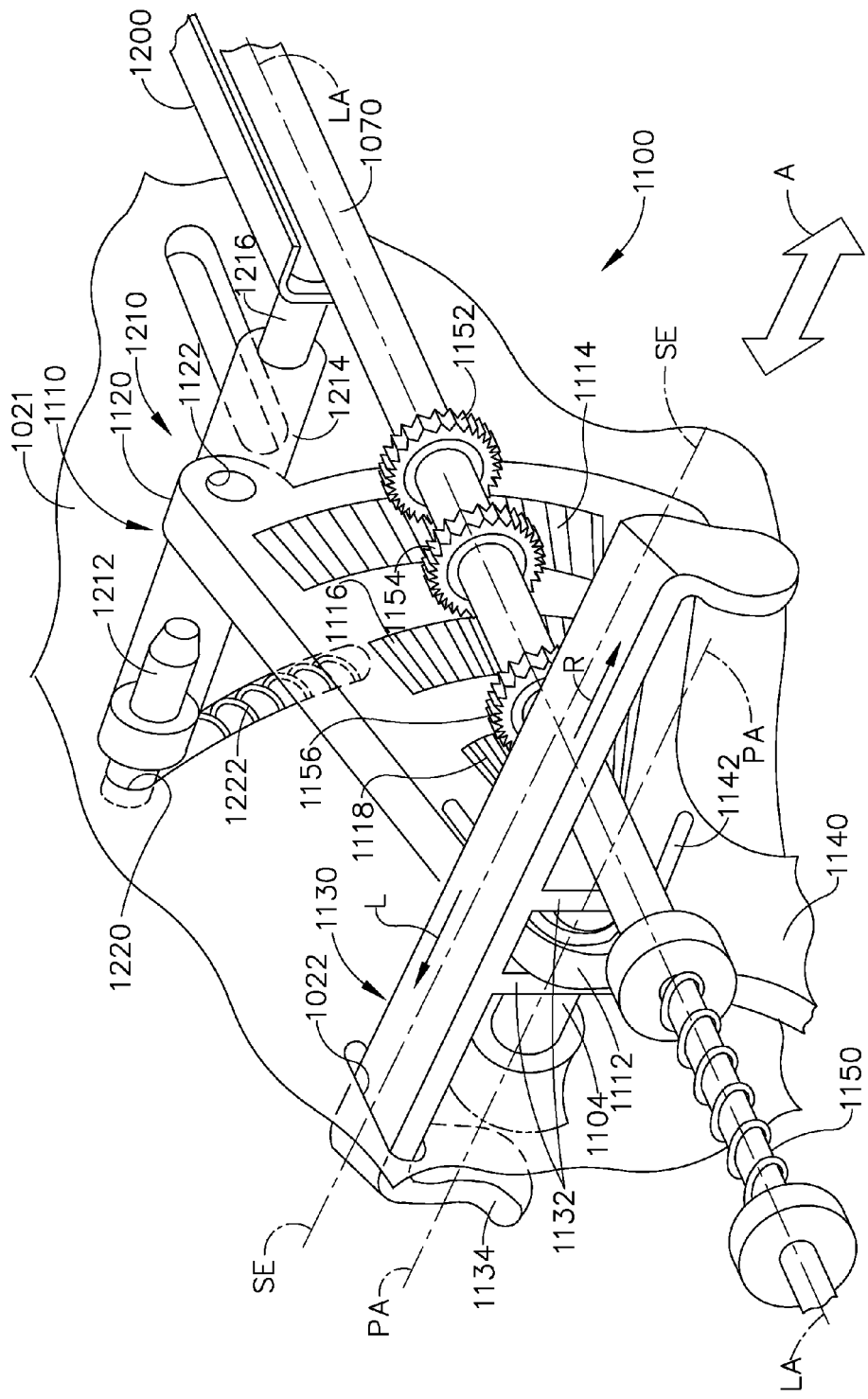
FIG. 20 is a partial perspective view of one embodiment of an actuation system of a modular surgical instrument.

Various embodiments of the modular surgical instrument 1010 include a unique and novel transmission or actuation system that facilitates the selective application of a variety of different axial and rotary motions to a particular surgical tool head attached thereto. Referring to FIGS. 19 and 20, one form of actuation system 1100 includes a gear plate 1110 that is pivotally supported in the handle assembly 1020 for selective pivotal travel about a pivot axis PA-PA that is substantially transverse to the instrument's longitudinal axis LA-LA. The gear plate 1110 may be pivotally supported within the handle assembly 1020 on a pivot shaft 104 that extends between the handle casing segments 1021. As will be discussed in further detail below, the gear plate 1110 is also laterally movable on the pivot shaft 1104 from a first rotary drive position to a second axial drive position by a first drive selector switch 1130 that is slidably supported between the handle case segments 1021. As can be seen in FIG. 20, the first drive selector switch 1130 is provided with two downwardly protruding clevis arms 1132 that are configured to receive a proximal end portion 1112 of the gear plate 1110 therebetween. The first drive selector switch 1130 extends through slots 1022 in the handle case members 1021 and have down turned end portions 1134 to enable the user to slide the first drive selector switch 1110 laterally back and forth (arrow "A" in FIG. 20) within the handle assembly 1020 along a selector axis SE-SE that is substantially transverse to the longitudinal axis LA-LA. An "actuator" in the form of a firing trigger 1140 is attached to, or otherwise integrally formed with, the gear plate 1110 such that the gear plate 1110 may be selectively pivoted about the pivot axis PA-PA by squeezing the firing trigger 1140 toward the handle assembly 1020. The term "actuator" may also encompass a portion of a robotic system configured to apply the requisite actuation motion to the gear plate 1110.

Figure 20A:
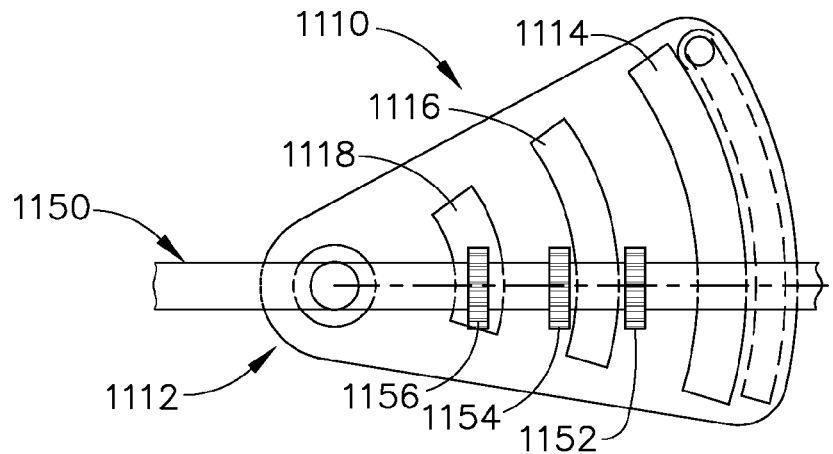
FIGS. 20A-20C are side views of a gear plate and rotary drive shaft.
Figure 20B:
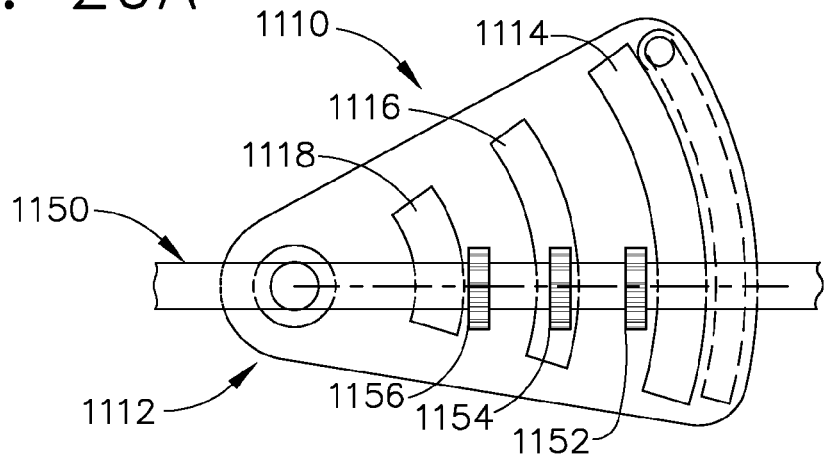
Figure 20C:
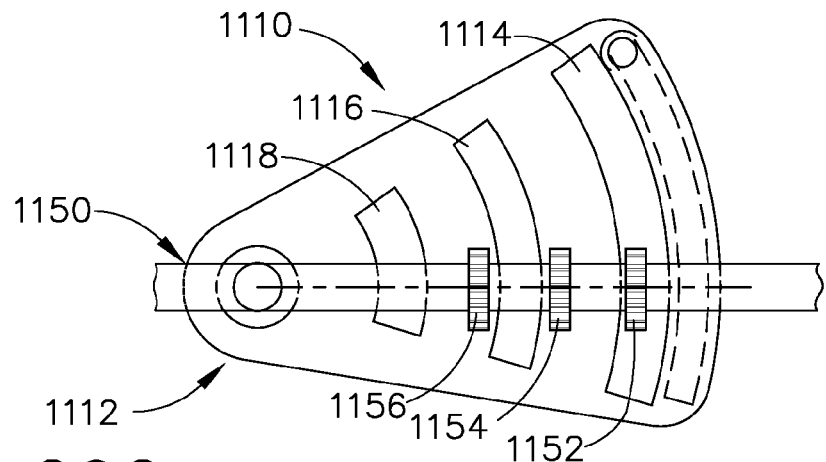

As can be further seen in FIG. 19, the gear plate 1110 is configured to operably interact with a rotary drive shaft 1150 that extends through the outer shaft casing 1070 of the elongated shaft assembly 1060 and is rotatably supported therein. In various embodiments, the gear plate 1110 has a first gear rack 1114, a second gear rack 1116, and a third gear rack 1118 formed thereon. See FIGS. 20A-20C. The rotary drive shaft 1150 has a first pinion gear 1152 that is adapted for selective meshing engagement with the first gear rack 1114 and a second pinion gear 1154 that is adapted for selective meshing engagement with the second gear rack 1116 and a third pinion gear 1156 that is adapted for selective meshing engagement with the third gear rack 1118. As will become further apparent as the present Detailed Description proceeds, each gear rack 1114, 1116, 1118 defines a discrete amount of rotary travel that may be applied to the rotary drive shaft 1150. For example, the first gear rack 1114, when in meshing engagement with the first pinion gear 1152, may facilitate an application of a first amount of rotary travel to the rotary drive shaft 1150 upon application of an actuation motion to the firing trigger 1140. For example, the first gear rack 1114 may facilitate a first amount of rotary travel of approximately 0.70" when the firing trigger 1140 is pivoted from a starting position to an ending position. The second gear rack 1116, when in meshing engagement with the second pinion gear 1154, facilitates a second range of rotary travel to the rotary drive shaft 1150. For example, the second gear rack 1116 may facilitate a second amount of rotary travel of approximately 1.41" when the firing trigger 1140 is pivoted from a starting position to an ending or fully depressed position. The third gear rack 1118, when in meshing engagement with the third pinion gear 1156, facilitates a third amount of rotary travel of approximately 2.11" when the firing trigger 1140 is pivoted from a starting position to an ending or fully depressed position. It will be understood, however, that other numbers and lengths of gear rack and pinion gear arrangements could conceivably be employed without departing from the spirit and scope of the present invention.

Also in various handle assembly embodiments, a torsion spring 1142 is employed to bias the firing trigger 1140 to the unactuated position shown in FIG. 18. Thus, in various embodiments, once the surgeon releases the firing trigger 1140, the spring 1142 returns the firing trigger 1140 to the unactuated position and, in doing so, applies a reverse rotary motion to the rotary drive shaft 1150. Various forms of known trigger safety arrangements such as those disclosed in U.S. Pat. No. 7,506,791, entitled "Surgical Stapling Instrument With Mechanical Mechanism For Limiting Maximum Tissue Compression", the disclosure of which is herein incorporated by reference in its entirety, may also be employed.

The rotary drive shaft 1150 further has a proximal end 1160 that is supported within the handle assembly for rotary and axial travel therein. In one embodiment, for example, the proximal end 1160 of the rotary drive shaft 1150 is configured to support a bearing assembly 1162 thereon that is constrained to move in axial tracks 1170 formed in the handle cases 1021. See FIG. 19. The bearing assembly 1162 facilitates rotation of the rotary drive shaft 1150 about the longitudinal axis LA-LA while also facilitating its axial travel within the handle assembly 1020 and the outer shaft casing 1070 of the shaft assembly 1060. As can be seen in FIG. 19, a compression spring 1164 serves to bias the rotary drive shaft 1150 in the distal direction "DD".

As can also be seen in FIGS. 19-24, the rotary drive shaft 1150 is hollow and has a distal end portion 1180 that is configured to operationally mate with various forms of surgical tool heads attached thereto. To facilitate axial positioning of the rotary drive shaft 1150 relative to the gear plate 1110 upon attachment of various surgical tool heads to the shaft assembly 1060, the distal end portion 1180 has an actuator flange 1182 formed thereon. Thus, when a particular surgical tool head is coupled to the shaft assembly 1060, its distal end contacts the actuation shaft 1182 to bias the rotary drive shaft 1150 in the proximal direction.

Figure 21:
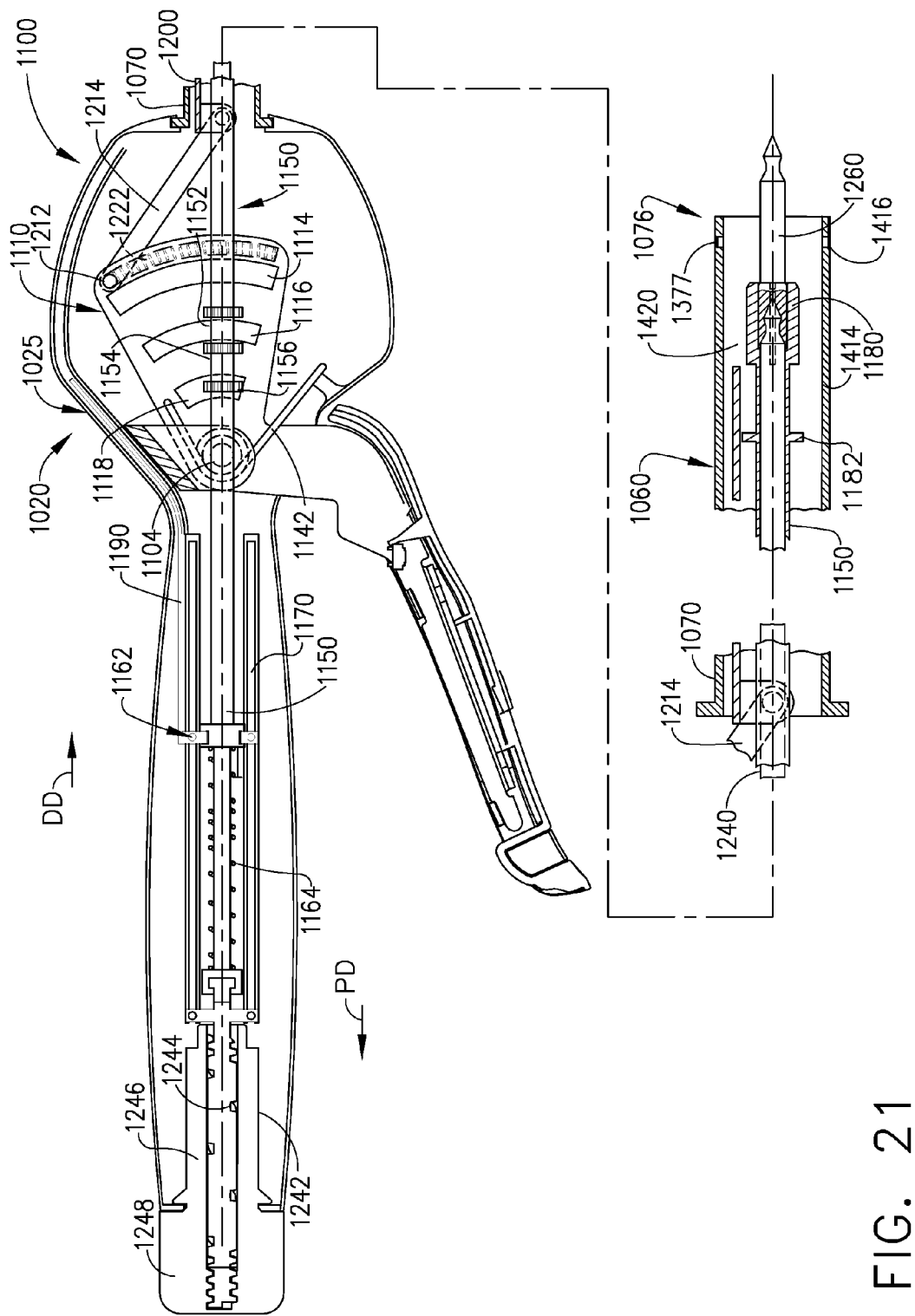
FIG. 21 is another cross-sectional view of the modular surgical instrument of FIG. 19.
Figure 22:
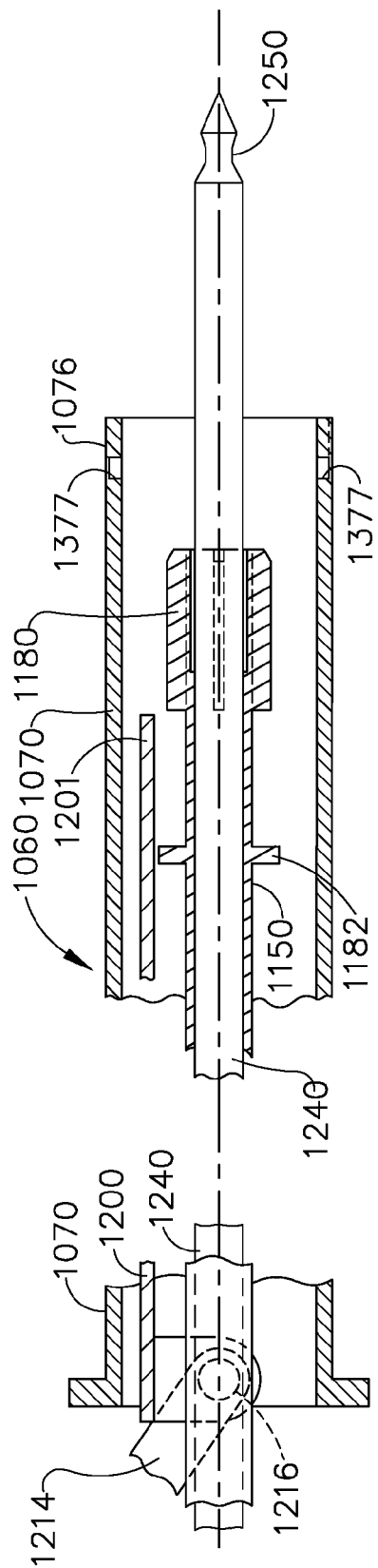
FIG. 22 is a cross-sectional view of a portion of the shaft assembly of the modular surgical instrument of FIG. 19.
Figure 23:
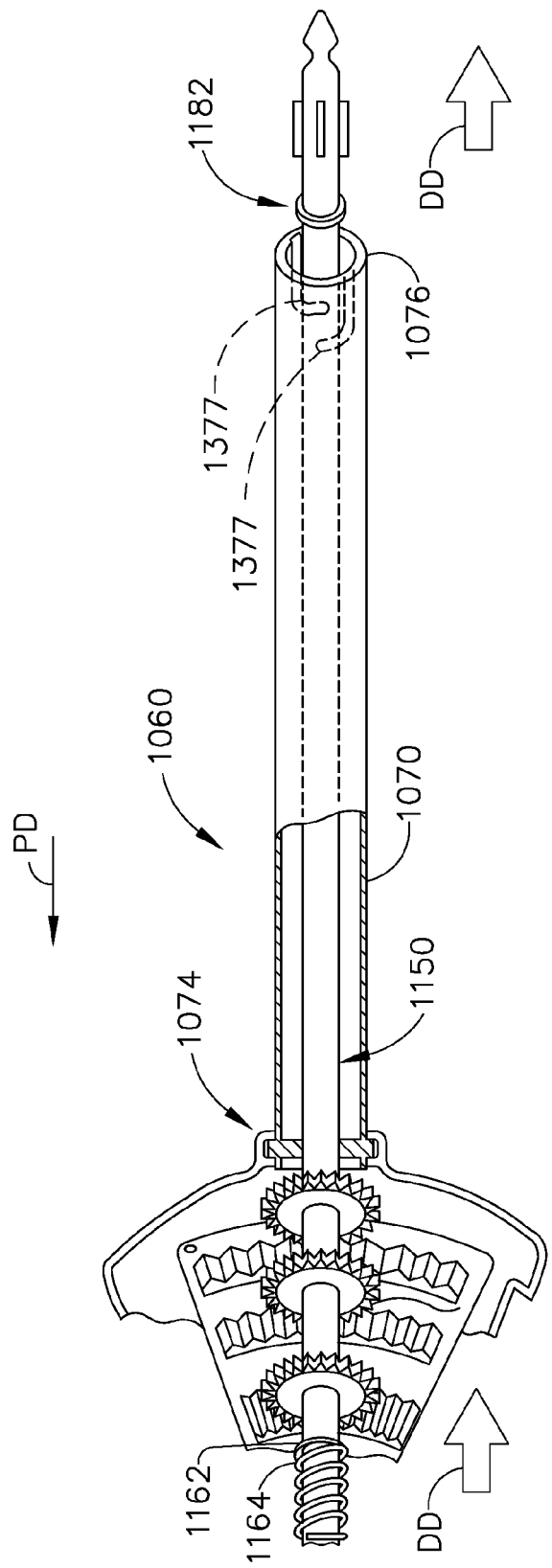
FIG. 23 is a partial cross-sectional view of the handle and shaft assembly of the modular surgical instrument of FIGS. 19 and 21.

Also in various embodiments, the handle assembly 1020 may have a window or opening 1025 therein (FIG. 19) that facilitates viewing by the surgeon of an indicator member 1190. In various embodiments, the indicator member 1190 may comprise a tape member that is flexible enough to axially travel back and forth within the handle assembly 1020 and be viewable through the window or opening 1025. The tape member 1190 is attached to the bearing assembly 1162 as can be seen in FIGS. 19 and 21 and has indication indicia thereon that corresponds to the gear rack 1114, 1116, 1118 that is engaged with its corresponding pinion gear 1152, 1154, 1156, respectively. For example, the indicator indicia may comprise a picture, drawing, diagram, model identification number, etc. of the particular surgical tool head that requires the corresponding amount of discrete rotary travel of the rotary drive shaft 1150 for actuation purposes.

The instrument 1010 further includes axial drive arrangements for selectively applying axial actuation motions to the various surgical tool heads attached to the shaft assembly 1060. As was discussed above, a first drive selector switch 1130 is configured to engage the proximal end portion 1112 of the gear plate 1110. Such arrangement permits the first drive selector switch 1130 to be used to laterally move the gear plate 1110 on the pivot shaft 1104 between a first rotary drive position wherein an application of an actuation motion to the firing trigger 1140 results in the application of a rotary drive motion to the rotary drive shaft 1150 and a second axial drive position wherein an application of an actuation motion to the firing trigger 1140 results in the application of an axial drive motion to an axial drive bar 1200. More specifically and with reference to FIGS. 19-21, the axial drive bar 1200 is coupled to an axial drive linkage 1210 that is configured to releasably interface with the gear plate 1110. As can be seen in FIG. 20, the gear plate 1110 has an engagement lug 1120 formed thereon that has a hole 1122 that is sized to receive a first engagement pin 1212 that protrudes from the axial drive linkage 1210. The axial drive bar 1200 is pinned to a linkage bar 1214 by a pin 1216 that extends through the linkage bar 1214 into a slot 1218 in the handle casing 1021. As can be most particularly seen in FIG. 20, the first engagement pin 1212 is also attached to the linkage bar 1214 and protrudes therethrough into a second slot 1220 in the handle case 1021. A compression spring 1222 is supported within the slot 1222 to bias the pin 1212 within the slot 1220 to the starting position shown in FIG. 20. The axial drive bar 1200 has a distal end 1201 that is configured to engage a corresponding portion of the particular surgical tool head that has been coupled to the modular surgical instrument 1010 to apply the requisite amount of axial drive motion thereto.

Thus, to actuate the axial drive bar 1200, the surgeon laterally moves the first drive selection switch 1130 in the "L" direction to bring the pin 1212 into the hole 1122 in the gear plate attached lug 1120. This action also moves the gear plate 1110 to the axial drive position wherein all of the gear racks 1114, 1116, 1118 are out of meshing engagement with their corresponding pinion gears 1152, 1154, 1156 on the rotary drive shaft 1150 and the gear plate 1110 is in driving engagement with the axial drive bar 1200. Thereafter, the surgeon may depress the firing trigger 1140 to drive the axial drive bar 1200 distally within the outer shaft casing 1070 of the shaft assembly 1060. When the surgeon releases the firing trigger 1140, the springs 1222 and 1142 bias the gear plate 1110, axial drive bar 1200 and firing trigger 1140 back to the starting position.

Various embodiments of the modular surgical instrument 1010 of the present invention include a tool acquisition shaft 1240 that axially extends through the rotary drive shaft 1150. In various embodiments the proximal end portion 1242 of the tool acquisition shaft 1240 has a series of helical threads 1244 thereon that is configured to rotatably interface with a closure nut portion 1246 interfacing with an adjustment knob 1248 located on the proximal end of the handle assembly 1020. Such adjustment knob and closure nut arrangements are known in the art and will not be described in further detail herein. See, e.g., U.S. Pat. No. 7,506,791, the disclosure of which has been herein incorporated by reference. Thus, rotation of the adjustment knob 1248 relative to the handle assembly 1020 will result in the axial movement of the tool acquisition shaft 1240 within the rotary drive shaft 1150.

As is apparent from the foregoing description, various forms of the modular surgical instrument 1010 are well-suited for actuating a variety of different forms of surgical tool heads that may be required, for example, during a single surgical operation—particularly those devices/tool heads that are used to perform different surgical procedures or actions within the colon. A variety of such surgical tool head arrangements are disclosed in the various U.S. Patent Applications identified above which were incorporated herein by reference in their respective entireties. Such surgical tool head embodiments employ a "bayonet-type" attachment configuration for attaching the surgical tool head to the shaft assembly 1060. For example, to attach a surgical tool head to the shaft assembly 1060, the user aligns pins that extend from attachment portion of the tool head with corresponding bayonet-type slots 1377 provided in the distal end 1076 of the outer shaft casing 1070. See FIG. 23. Once the pins are aligned with their respective slots 1377, the user inserts the attachment stem portion of the surgical tool head into the distal end 1076 of the outer shaft casing 1070 and, when seated therein, rotates the surgical tool head slightly to seat the pins into their respective bayonet slots 1377. In alternate embodiments, the pins may be provided on the outer shaft casing and the slots may be provided in the attachment stems.

Figure 24:
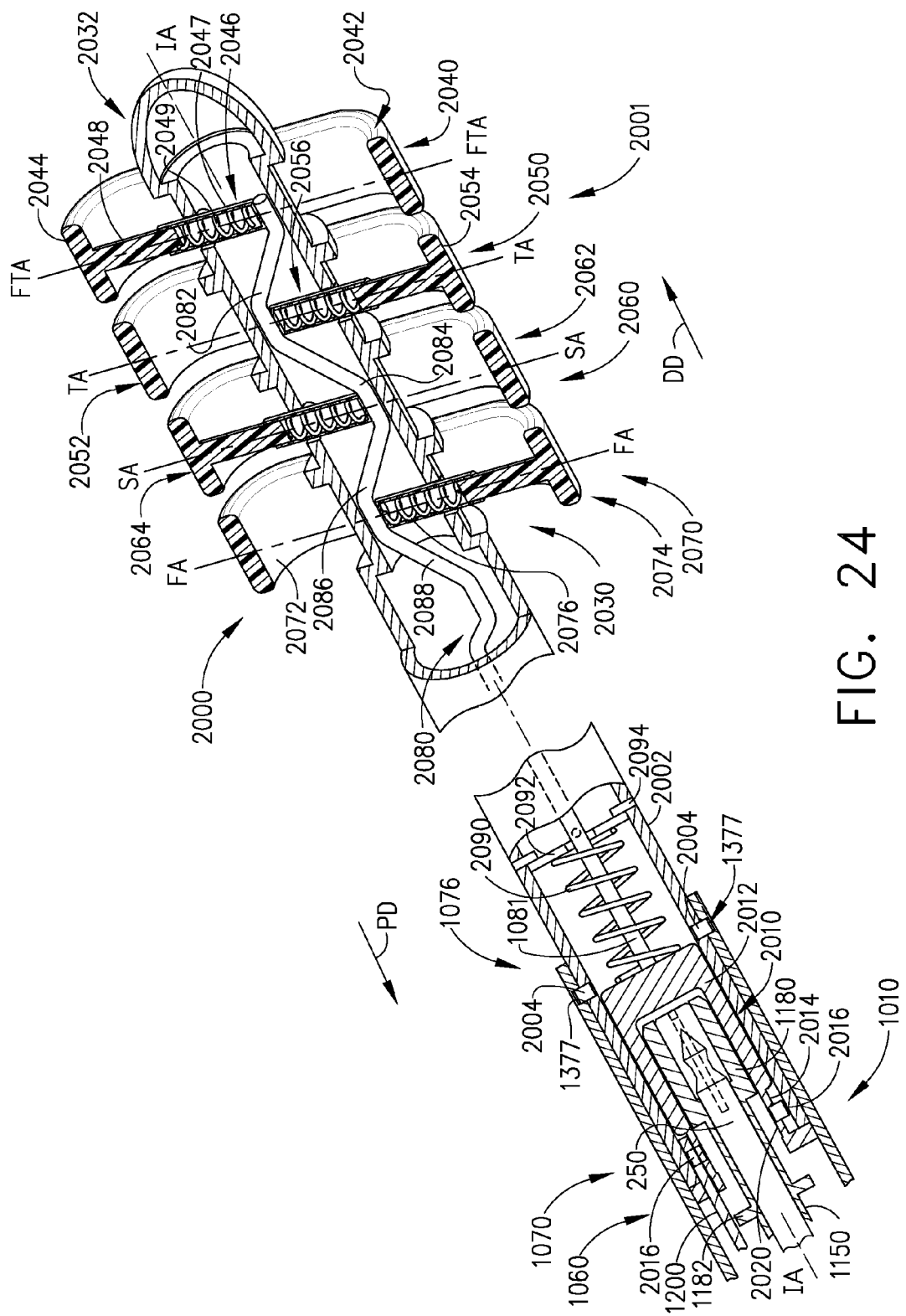
FIG. 24 is a partial cross-sectional view of a tissue manipulation device embodiment of the present invention attached to the shaft assembly of the modular surgical instrument of FIGS. 18-23.

FIG. 24 illustrates a surgical tool head in the form of a tissue manipulation device 2000 that is specifically configured for use in connection with at least one form of modular surgical instrument 1010. As can be seen in that Figure, the tissue manipulation device 2000 has an attachment stem portion 2002 that has a pair of attachment pins 2004 protruding therefrom. To attach the tissue manipulation device 2000 to the shaft assembly 1060, the user aligns pins 2004 with the corresponding bayonet-type slots 1377 provided in the distal end 1076 of the outer shaft casing 1070. Once the pins 2004 are aligned with their respective slots 1377, the user inserts the attachment stem portion 2002 into the distal end 1076 of the outer shaft casing 1070 and, when seated therein, rotates the tissue manipulation device 2000 slightly to seat the pins 2004 into their respective bayonet slots 1377.

As can be further seen in FIG. 24, the tissue manipulation device 2000 further includes an actuation adapter 2010 that is configured to operably interface with the axial drive shaft 1200. In at least one form, the actuation adapter 2010 includes an attachment cap 2012 that is sized to extend over the distal end portion 1180 of the rotary drive shaft 1150 as shown so as to be axially movable relative thereto. The proximal end 2014 of the attachment cap 2012 has a pair of diametrically opposed attachment pins 2016 protruding therefrom. Each of the attachment pins 2016 is configured to hooking engage the distal end of the axial drive shaft 1200 when the attachment stem portion 2002 is coupled to the shaft assembly 1060. A thrust washer 2018 is removably affixed to the distal end portion 2020 of the attachment stem 2002 to retain the movable attachment cap 2012 within the attachment stem 2002.

As can also be seen in FIG. 24, the attachment stem portion 2002 protrudes from a central shaft assembly 2030 that defines an insertion axis IA-IA. The distal end portion of the central shaft assembly 2030 terminates in a substantially hollow blunt end cap 2032. In at least one form, the tissue manipulation device 2000 further comprises a plurality of tissue manipulation arms 2040, 2050, 2060, 2070 that are operably supported on the central shaft assembly 2030. More specifically, a first tissue manipulation arm 2040 comprises a first body portion 2042 that has a relatively blunt first tissue manipulation end 2044. The first tissue manipulation arm 2040 is constrained to move laterally along a first axis FA-FA that is substantially transverse to the installation axis IA-IA between the insertion position shown in FIG. 24 and at least one deployed position as was discussed above.

Likewise, a second tissue manipulation arm 2050 comprises a second body portion 2052 that has a relatively blunt second tissue manipulation end 2054. The second tissue manipulation arm 2050 is constrained to move laterally along a second axis SA-SA that is substantially transverse to the installation axis IA-IA between a first insertion position shown in FIG. 24 and at least one deployed position. A third tissue manipulation arm 2060 comprises a third body portion 2062 that has a relatively blunt third tissue manipulation end 2064. The third tissue manipulation arm 2060 is constrained to move laterally along a third axis TA-TA that is substantially transverse to the installation axis IA-IA between a first insertion position shown in FIG. 24 and at least one deployed position. A fourth tissue manipulation arm 2070 comprises a fourth body portion 2072 that has a relatively blunt fourth tissue manipulation end 2074. The fourth tissue manipulation arm 2070 is constrained to move laterally along a fourth axis FTA-FTA that is substantially transverse to the installation axis IA-IA between a first insertion position shown in FIG. 24 and at least one deployed position.

Various embodiments of the tissue manipulation device 2000 further include an actuator rod 2080 for selectively applying deployment motions to the tissue manipulation arms 2040, 2050, 2060, 2070. As can be seen in FIG. 24, in at least one form, the actuator rod 2080 has a plurality of bends 2082, 2084, 2086, 2088 therein. The actuator rod 2080 is configured for selective axial travel within the central shaft assembly 2030 and the tissue manipulation arms 2040, 2050, 2060, 2070. The bends 2082, 2084, 2086, 2088 in actuator rod 2080 are configured to selectively engage spring biased detents located on the inside of or otherwise attached to the tissue manipulation arms 2040, 2050, 2060, 2070. More specifically, as can be seen in FIG. 24, the first tissue manipulation arm 2040 has a first spring loaded detent 2046 therein that comprises a piston head 2047 that is movably journaled on a pin 2048. A spring 2049 is provided to apply a biasing force to the piston head 2047. The second tissue manipulation arm 2050 has a second spring loaded detent 2056 therein that is substantially the same as the first spring loaded detent 2046. The third tissue manipulation arm 2060 has a third spring loaded detent 2066 therein that is substantially the same as the first spring loaded detent 2046. The fourth tissue manipulation arm 2070 has a fourth spring loaded detent 2076 therein that is substantially the same as the first spring loaded detent 2046. In at least one embodiment, an expandable sheath assembly is inserted over the tool head as was described above.

In at least one embodiment, a proximal end portion 1081 of the actuator rod 2080 is attached to the actuator cap 2012. An actuator spring 2090 is employed to bias the actuator cap 2012 in the proximal direction "PD" to retain the tissue manipulator 2000 in the insertion position (FIG. 24) prior to applying an actuation force thereto. The actuator spring 2090 extends between the actuator cap 2012 and a thrust washer 2092 that is retained in position by pins 2094 that are inserted into the central shaft portion 2030.

Once the tissue manipulation device 2000 has been attached to the shaft assembly 1060 of the modular surgical instrument 1010 as described above, it may be used by inserting the head portion 2001 of the device 2000 with the sheath thereover into the colon through the anus. Once the head assembly 2001 has been inserted to the desired position in the insertion or unexpanded orientation (FIG. 24), the surgeon applies and actuation force to the actuation rod 2080 to force it within the central shaft assembly 2030 in the distal direction "DD". This action is accomplished by moving the first drive selection switch 1130 in the "L" direction (FIG. 20) to bring the pin 1212 into the hole 1122 in the gear plate attached lug 1120. This action also moves the gear plate 1110 to the axial drive position wherein all of the gear racks 1114, 1116, 1118 are out of meshing engagement with their corresponding pinion gears 1152, 1154, 1156 on the rotary drive shaft 1150 and the gear plate 1110 is in driving engagement with the axial drive bar 1200. Thereafter, the surgeon depresses the firing trigger 1140 to drive the axial drive bar 1200 distally within the outer shaft casing 1070 of the shaft assembly 1060. Such action also moves the actuator cap 2012 and actuator rod 2080 distally. As the actuator rod 2080 is moved distally, the bend 2082 contacts detent 2046 and pushes the first tissue manipulation arm 2040 laterally along the first axis FA-FA. Likewise, the bend 2084 contacts the second detent 2056 and pushes the second tissue manipulation arm 2050 laterally along the second axis SA-SA. The bend 2086 contacts the third detent 2066 and biases the third tissue manipulation arm 2060 laterally along the third axis TA-TA. The bend 2088 contacts the fourth detent 2076 and biases the fourth tissue manipulation arm 2070 laterally along the fourth axis FTA-FTA. The distal most bend 2082 extends into the hollow cap 2032. When the surgeon releases the trigger 1140, the actuator rod 2080 will be pulled in the proximal direction, thereby causing the bends 2082, 2084, 2086, 2088 to move the tissue manipulation arms 2040, 2050, 2060, 2070, respectively to their insertion or un-deployed positions as shown in FIG. 24.

Further to the above, it will be understood that any one or more of the tissue manipulation devices disclosed herein, such as tissue manipulation devices 100, 200, 300, and/or or 500, for example, can comprise a modular end effector which can be assembled to a shaft assembly of a surgical instrument, such as shaft assembly 1060 of surgical instrument 1010. In various embodiments, referring generally to FIGS. 11-14, a surgical instrument can comprise a first actuator and a second actuator, wherein the first actuator can be operably coupled to the first actuation shaft 390 and the second actuator can be operably coupled to the second actuation shaft 400 when the end effector 300 is assembled to the shaft assembly of the surgical instrument. In at least one such embodiment, the first actuation shaft 390 can engage the first actuator and the second actuation shaft 400 can engage the second actuator as the end effector 300 is assembled to the shaft of the surgical instrument via a bayonet connection, for example.

The various tissue manipulation devices of the present invention provide the surgeon with considerable flexibility when performing surgical procedures on the colon. Such devices enable the surgeon to gain access to the veins and arteries on the sides of the rectum during mobilization and can also be effectively used to prevent the tissue from bunching up while avoiding over stretching. Once inserted, the device may be used to introduce some bend/articulation of portions of the colon. Use of the expandable sheath may serve to avoid inadvertent damage to the inside of the colon during manipulation. While several embodiments of the invention have been described, it should be apparent, however, that various modifications, alterations and adaptations to those embodiments may occur to persons skilled in the art with the attainment of some or all of the advantages of the invention. For example, according to various embodiments, a single component may be replaced by multiple components, and multiple components may be replaced by a single component, to perform a given function or functions. Accordingly, it is expressly intended that all such equivalents, variations and changes which fall within the spirit and scope of the present invention as defined in the claims be embraced thereby.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A rectal manipulation device, comprising:
a shaft assembly defining an insertion axis, wherein at least a portion of said shaft assembly is configured to be inserted into a patient's rectum; and
a plurality of tissue manipulation arms each having a tissue manipulation end, each said tissue manipulation arm operably supported by said shaft assembly, wherein at least some of said tissue manipulation arms are selectively movable from a first insertion position wherein all of said tissue manipulation ends are substantially aligned relative to each other and, upon application of an actuation motion thereto, said at least some of said tissue manipulation arms move to other deployed positions about said insertion axis such that said tissue manipulation ends of said plurality of tissue manipulation arms are not all substantially aligned relative to each other and wherein one of said at least some of said tissue manipulation arms is constrained to move along a corresponding transverse axis that is substantially transverse to said insertion axis from said first insertion position to one of said other deployed positions upon application of said actuation motion thereto and wherein another one of said at least some of said tissue manipulation arms is constrained to move along another corresponding transverse axis that is substantially transverse to said insertion axis and parallel to said corresponding transverse axis from said first insertion position to another one of said other deployed positions upon application of said actuation motion thereto.

2. The rectal manipulation device of claim 1 further comprising an expandable sheath extending over at least some of said plurality of tissue manipulation arms, said expandable sheath configured to retain said at least some of said plurality of tissue manipulation arms in said first insertion position and expand as said at least some of said plurality of tissue manipulation arms are moved to said other deployed positions.

3. The rectal manipulation device of claim 1 wherein, upon application of said actuation motion to said one of said at least some of said tissue manipulation arms, said one of said at least some of said tissue manipulation arms moves to said one of said other deployed positions wherein said tissue manipulation end thereof is located on one lateral side of said insertion axis and, upon application of said actuation motion to said another one of said at least some of said tissue manipulation arms causes said another one of said at least some of said tissue manipulation arms to move to said another said other deployed position wherein said tissue manipulation end thereof is located on another lateral side of said insertion axis.

4. The rectal manipulation device of claim 1 wherein said actuation motion is applied to said at least some of said tissue manipulation arms by a tension member operably engaging a deployment portion thereof such that, upon application of tension to said tension member, said at least some of said tissue manipulation arms are moved to at least some of said other deployed positions.

5. The rectal manipulation device of claim 4 wherein each said deployment portion of said at least some of said tissue manipulation arms is configured to return said at least some of said tissue manipulation arms from said at least some other deployed positions to said insertion position upon removal of said application of tension to said tension member.

6. The rectal manipulation device of claim 1 wherein said plurality of said tissue manipulation arms is equally spaced along a portion of said shaft assembly.

7. The rectal manipulation device of claim 1 wherein said at least some of said tissue manipulation arms that are selectively movable are configured to move axially along said insertion axis upon application of said actuation motion thereto.

8. A rectum manipulation device, comprising:
a shaft assembly defining an insertion axis;
a first tissue manipulation arm movably supported on said shaft assembly and is movable relative thereto along a first axis that is substantially transverse to said insertion axis;
a second tissue manipulation arm movably supported on said shaft assembly and is movable relative thereto along a second axis that is substantially transverse to said insertion axis;
a third tissue manipulation arm movably supported on said shaft assembly and is movable relative thereto along a third axis that is substantially transverse to said insertion axis;
a fourth tissue manipulation arm movably supported on said shaft assembly and is movable relative thereto along a fourth axis that is substantially transverse to said insertion axis; and
an actuation member comprising a tension member operably interfacing with each of said first, second, third, and fourth tissue manipulation arms such that, upon application of an actuation motion to said tension member, said tension member applies deployment motions to said first, second, third and fourth tissue manipulation arms.

9. The rectum manipulation device of claim 8 further comprising
a first biasing member biasing said first tissue manipulation arm to a first insertion position upon discontinuing said application of said deployment motion thereto;
a second biasing member biasing said second tissue manipulation arm to a second insertion position upon discontinuing said application of said deployment motion thereto;
a third biasing member biasing said third tissue manipulation arm to a third insertion position upon discontinuing said application of said deployment motion thereto; and
a fourth biasing member biasing said fourth tissue manipulation arm to a fourth insertion position upon discontinuing said application of said deployment motion thereto.

10. The rectum manipulation device of claim 8 wherein said actuation member is configured to operably engage corresponding portions of each of said first, second, third, and fourth tissue manipulation arms when said actuation motion is applied thereto in a first direction, said actuation member configured to disengage said corresponding portions of each of said first, second, third, and fourth tissue manipulation arms when said actuation motion is applied thereto in a second direction that is opposite to said first direction.

11. A rectal manipulation device, comprising:
a shaft assembly defining an insertion axis, wherein at least a portion of said shaft assembly is configured to be inserted into a patient's rectum; and
a plurality of tissue manipulation arms each having a tissue manipulation end, each said tissue manipulation arm operably supported by said shaft assembly, wherein at least some of said tissue manipulation arms are selectively movable from a first insertion position wherein all of said tissue manipulation ends are substantially aligned relative to each other and, upon application of an actuation motion thereto, said at least some of said tissue manipulation arms move to other deployed positions about said insertion axis such that said tissue manipulation ends of said plurality of tissue manipulation arms are not all substantially aligned relative to each other and wherein said actuation motion is applied to said at least some of said tissue manipulation arms by a tension member operably engaging a deployment portion thereof such that, upon application of tension to said tension member, said at least some of said tissue manipulation arms are moved to at least some of said other deployed positions.

12. The rectal manipulation device of claim 11 further comprising an expandable sheath extending over at least some of said plurality of tissue manipulation arms, said expandable sheath configured to retain said at least some of said plurality of tissue manipulation arms in said first insertion position and expand as said at least some of said plurality of tissue manipulation arms are moved to said other deployed positions.

13. The rectal manipulation device of claim 11 wherein, upon application of said actuation motion to one of said at least some of said tissue manipulation arms, said one of said at least some of said tissue manipulation arms moves to one of said other deployed positions wherein said tissue manipulation end thereof is located on one lateral side of said insertion axis and, upon application of said actuation motion to another one of said at least some of said tissue manipulation arms causes said another one of said at least some of said tissue manipulation arms to move to another said other deployed position wherein said tissue manipulation end thereof is located on another lateral side of said insertion axis.

14. The rectal manipulation device of claim 11 wherein one of said at least some of said tissue manipulation arms is constrained to move along a corresponding transverse axis that is substantially transverse to said insertion axis from said first insertion position to one of said other deployed positions upon application of said actuation motion thereto and wherein another one of said at least some of said tissue manipulation arms is constrained to move along another corresponding transverse axis that is substantially transverse to said insertion axis from said first insertion position to another one of said other deployed positions upon application of said actuation motion thereto.

15. The rectal manipulation device of claim 14 wherein said corresponding transverse axis is substantially parallel to said corresponding transverse axis.

16. The rectal manipulation device of claim 11 wherein each deployment portion of said at least some of said tissue manipulation arms is configured to return said at least some of said tissue manipulation arms from said at least some other deployed positions to said insertion position upon removal of said application of tension to said tension member.

17. The rectal manipulation device of claim 11 wherein said plurality of said tissue manipulation arms are equally spaced along a portion of said shaft assembly.

18. A rectal manipulation device, comprising:
a shaft assembly defining an insertion axis, wherein at least a portion of said shaft assembly is configured to be inserted into a patient's rectum; and
a plurality of tissue manipulation arms each having a tissue manipulation end, each said tissue manipulation arm operably supported by said shaft assembly, wherein at least some of said tissue manipulation arms are selectively movable from a first insertion position wherein all of said tissue manipulation ends are substantially aligned relative to each other and, upon application of an actuation motion thereto, said at least some of said tissue manipulation arms move to other deployed positions about said insertion axis such that said tissue manipulation ends of said plurality of tissue manipulation arms are not all substantially aligned relative to each other and wherein one of said at least some of said tissue manipulation arms is constrained to move along a corresponding transverse axis that is substantially transverse to said insertion axis from said first insertion position to one of said other deployed positions upon application of said actuation motion thereto and wherein another one of said at least some of said tissue manipulation arms is constrained to move along another corresponding transverse axis that is substantially transverse to said insertion axis and axially spaced from said corresponding transverse axis from said first insertion position to another one of said other deployed positions upon application of said actuation motion thereto.

19. The rectal manipulation device of claim 18 further comprising an expandable sheath extending over at least some of said plurality of tissue manipulation arms, said expandable sheath configured to retain said at least some of said plurality of tissue manipulation arms in said first insertion position and expand as said at least some of said plurality of tissue manipulation arms are moved to said other deployed positions.

20. The rectal manipulation device of claim 18 wherein, upon application of said actuation motion to said one of said at least some of said tissue manipulation arms, said one of said at least some of said tissue manipulation arms moves to one of said other deployed positions wherein said tissue manipulation end thereof is located on one lateral side of said insertion axis and, upon application of said actuation motion to another one of said at least some of said tissue manipulation arms causes said another one of said at least some of said tissue manipulation arms to move to another said other deployed position wherein said tissue manipulation end thereof is located on another lateral side of said insertion axis.

21. The rectal manipulation device of claim 18 wherein said one of said at least some of said tissue manipulation arms is constrained to move along a corresponding transverse axis that is substantially transverse to said insertion axis from said first insertion position to said one of said other deployed positions upon application of said actuation motion thereto and wherein said another one of said at least some of said tissue manipulation arms is constrained to move along another corresponding transverse axis that is substantially transverse to said insertion axis from said first insertion position to said another one of said other deployed positions upon application of said actuation motion thereto.

22. The rectal manipulation device of claim 21 wherein said corresponding transverse axis is substantially parallel to said another corresponding transverse axis.

23. The rectal manipulation device of claim 18 wherein said actuation motion is applied to said at least some of said tissue manipulation arms by a tension member operably engaging a deployment portion thereof such that, upon application of tension to said tension member, said at least some of said tissue manipulation arms are moved to at least some of said other deployed positions.

24. The rectal manipulation device of claim 23 wherein each said deployment portion of said at least some of said tissue manipulation arms is configured to return said at least some of said tissue manipulation arms from said at least some other deployed positions to said insertion position upon removal of said application of tension to said tension member.

25. A rectal manipulation device, comprising:
a shaft assembly defining an insertion axis, wherein at least a portion of said shaft assembly is configured to be inserted into a patient's rectum; and
a plurality of tissue manipulation arms each having a tissue manipulation end, each said tissue manipulation arm operably supported by said shaft assembly, wherein at least some of said tissue manipulation arms are selectively movable from a first insertion position wherein all of said tissue manipulation ends are substantially aligned relative to each other and, upon application of an actuation motion thereto, said at least some of said tissue manipulation arms move to other deployed positions about said insertion axis such that said tissue manipulation ends of said plurality of tissue manipulation arms are not all substantially aligned relative to each other and wherein one of said at least some of said tissue manipulation arms is constrained to move along a corresponding transverse plane that is substantially transverse to said insertion axis from said first insertion position to one of said other deployed positions upon application of said actuation motion thereto and wherein another one of said at least some of said tissue manipulation arms is constrained to move along another corresponding transverse plane that is substantially transverse to said insertion axis and parallel to said corresponding transverse plane from said first insertion position to another one of said other deployed positions upon application of said actuation motion thereto.

26. The rectal manipulation device of claim 25 further comprising an expandable sheath extending over at least some of said plurality of tissue manipulation arms, said expandable sheath configured to retain said at least some of said plurality of tissue manipulation arms in said first insertion position and expand as said at least some of said plurality of tissue manipulation arms are moved to said other deployed positions.

27. The rectal manipulation device of claim 25 wherein, upon application of said actuation motion to said one of said at least some of said tissue manipulation arms, said one of said at least some of said tissue manipulation arms moves to one of said other deployed positions wherein said tissue manipulation end thereof is located on one lateral side of said insertion axis and, upon application of said actuation motion to said another one of said at least some of said tissue manipulation arms causes said another one of said at least some of said tissue manipulation arms to move to another said other deployed position wherein said tissue manipulation end thereof is located on another lateral side of said insertion axis.

28. The rectal manipulation device of claim 25 wherein said actuation motion is applied to said at least some of said tissue manipulation arms by a tension member operably engaging a deployment portion thereof such that, upon application of tension to said tension member, said at least some of said tissue manipulation arms are moved to at least some of said other deployed positions.

\* \* \* \* \*